US008740762B2

(12) United States Patent
Hallahan et al.

(10) Patent No.: US 8,740,762 B2
(45) Date of Patent: Jun. 3, 2014

(54) SPECIFIC INHIBITION OF CPLA$_2$ ENHANCES THE EFFICACY OF RADIOTHERAPY

(75) Inventors: Dennis E. Hallahan, Nashville, TN (US); Eugenia M. Yazlovitskaya, Nolensville, TN (US)

(73) Assignee: Vanderbilt University, Nashville, TN (US)

(*) Notice: Subject to any disclaimer, the term of this patent is extended or adjusted under 35 U.S.C. 154(b) by 1509 days.

(21) Appl. No.: 12/098,796

(22) Filed: Apr. 7, 2008

(65) Prior Publication Data

US 2008/0262286 A1 Oct. 23, 2008

Related U.S. Application Data

(60) Provisional application No. 60/921,954, filed on Apr. 5, 2007.

(51) Int. Cl.
*A61N 5/00* (2006.01)

(52) U.S. Cl.
USPC .......... 600/3

(58) Field of Classification Search
USPC .......... 600/1-8; 128/897, 898
See application file for complete search history.

(56) References Cited

U.S. PATENT DOCUMENTS

2003/0032027 A1* 2/2003 Li et al. .......... 435/6
2003/0225011 A1* 12/2003 David et al. .......... 514/44

OTHER PUBLICATIONS

Cowan et al. (2006) J Appl Physiol 101:1127-35.
Geng et al. (2001) Cancer Res 61:2413-2419.
Gorski et al. (1999) Cancer Res 59:3374-3378.
Li et al. (2005) Am J Physiol Heart Circ Physiol 289:H2592-601.
Radisavljevic et al. (2000) J Biol Chem 275:20770-20774.
Tan & Hallahan (2003) Cancer Res 63:7663-7667.
Tan et al. (2006) Cancer Res 66:2320-2327.
Wang et al. (1999) Cancer Res 59:1464-1472.

* cited by examiner

*Primary Examiner* — Samuel Gilbert
(74) *Attorney, Agent, or Firm* — Jenkins, Wilson, Taylor & Hunt, P.A.

(57) ABSTRACT

A method for increasing the radiosensitivity of a target tissue in a subject is disclosed. In some embodiments, the methods includes administering a cytosolic phospholipase A2 (cPLA$_2$) antagonist to the subject, whereby the radiosensitivity of the target tissue is increased. Also disclosed are methods for suppressing tumor growth in a subject and methods for inhibiting tumor blood vessel growth.

34 Claims, 25 Drawing Sheets
(3 of 25 Drawing Sheet(s) Filed in Color)

SPECIFIC INHIBITION OF CPLA$_2$ ENHANCES THE EFFICACY OF RADIOTHERAPY

RELATED APPLICATIONS

The presently disclosed subject matter claims the benefit of U.S. Provisional Patent Application Ser. No. 60/921,954, filed Apr. 5, 2007, the disclosure of which is incorporated herein by reference in its entirety.

GOVERNMENT INTEREST

This presently disclosed subject matter was made with U.S. Government support under Grant Nos. R01-CA112385, R01-CA88076, R01-CA89674, R01-CA89888, and P50-CA90949, awarded by National Institutes of Health/National Cancer Institute of the United States of America. Thus, the U.S. Government has certain rights in the presently disclosed subject matter.

TECHNICAL FIELD

The presently disclosed subject matter generally relates to methods and compositions for enhancing the efficacy of radiotherapy. More particularly, the presently disclosed subject matter provides a method for enhancing the efficacy of anti-tumor radiotherapy by administering to a subject with a tumor a composition comprising an antagonist of a cytosolic phospholipase A2 (cPLA$_2$) biological activity.

BACKGROUND

Ionizing radiation is useful in the treatment of cancer and for ablation of pathologic tissues because of the cytotoxic effects which result from persistent DNA double strand breaks or activation of program cell death (Haimovitz-Friedman et al., 1994; Garcia-Barros et al., 2003; Brown & Attardi, 2005). Radiation causes rapidly proliferating cells, such as tumor and cancer cells, to undergo cell death by apoptosis, both in vivo and in vitro (Antonakopoulos et al., 1994; Li et al., 1994; Mesner et al., 1997).

Current radiation therapy is frequently unsuccessful at completely eradicating cancer cells from a patient, however. This is true for at least two reasons. One reason cancer can recur is that it is often not possible to deliver a sufficiently high dose of local radiation to kill tumor cells without concurrently creating an unacceptably high risk of damage to the surrounding normal tissue. Another reason is that tumors show widely varying susceptibilities to radiation-induced cell death. Ionizing radiation activates pro-survival response through phosphatidylinositol 3-kinase/Akt (PI3K/Akt) and mitogen-activated protein kinase (MAPK) signal transduction pathways (Dent et al., 2003; Tan & Hallahan, 2003; Tan et al., 2006; Yacoub et al., 2006). PI3K catalyzes the addition of a phosphate group to the inositol ring of phosphoinositides normally present in the plasma membrane of cells (Wymann & Pirola, 1998). The products of these reactions, including phosphatidyl-4,5-bisphosphate and phosphatidyl-3,4,5-trisphosphate, are potent second messengers of several RTK signals (Cantley, 2002). In vitro studies have indicated that PI3K and Akt are involved in growth factor-mediated survival of various cell types (Datta et al., 1999), including neuronal cells (Yao & Cooper, 1995; Dudek et al., 1997; Weiner & Chun, 1999), fibroblasts (Kauffmann-Zeh et al., 1997; Fang et al., 2000), and certain cells of hematopoietic origin (Katoh et al., 1995; Kelley et al., 1999; Somervaille et al., 2001).

The initial molecular events that trigger radiation-induced Akt signal transduction are presently unknown. The triggering events could involve hydroxyl interaction with some membrane lipids, signaling proteins or DNA (Kolesnick and Fuks 2003; Kufe and Weichselbaum 2003; Lammering et al. 2004; Truman et al. 2005).

Vascular endothelial growth factor (VEGF) is a potent angiogenic growth factor that normally acts directly on vascular endothelium to promote the survival of newly formed vessels (Alon et al., 1995; McMahon, 2000). VEGF has also been implicated in tumor proliferation (Bell et al., 1999), and several transformed cell lines express unusually high levels of VEGF (Kieser et al., 1994; Grugel et al., 1995; Graeven et al., 1999). In addition, elevated VEGF expression is clinically relevant as it is associated with worsened prognosis (Valter et al., 1999).

Elevated VEGF levels also correlate with radiation stress and radiotherapy resistance (Shintani et al., 2000). For example, VEGF expression is elevated in such radioresistant tumors as malignant glioma and melanoma (Liu et al., 1995). Interfering with VEGF signal transduction increases the in vitro radiosensitivity of glioblastoma and melanoma tumor models (Geng et al., 2001). These data suggest a role for VEGF in promoting cellular survival following radiotherapy. The mechanisms by which VEGF exerts this protective effect have not been elucidated, however.

Both in vitro and in vivo experiments have suggested that VEGF expression is induced when cells or tumors are exposed to ionizing radiation (Katoh et al., 1995; Gorski et al., 1999). For example, when growing Lewis lung carcinoma (LLC) cells are treated in vitro with different doses of irradiation, VEGF levels showed a dose-dependent increase within 24 hours of treatment (Gorski et al., 1999). Several other human tumor cell lines also showed an increase in VEGF expression after in vitro exposure to radiation, including Seg-1 (esophageal adenocarcinoma), SQ20B (a radioresistant squamous cell carcinoma line), U1 (melanoma), and T98 and U87 (glioblastoma; Gorski et al., 1999). Tumors produced in vivo by implanting LLC, Seg-1, or SQ20B cells into mice also showed enhanced VEGF expression after exposure to radiation (Gorski et al., 1999).

The induction of VEGF expression is associated with increased radioresistance of these cells and tumors. Neutralizing antibodies to VEGF, a soluble extracellular component of the Flk-1 receptor (one of three VEGF receptors so far identified), and a Flk-1-specific inhibitor are all able to eliminate this resistance phenotype both in vitro and in vivo, presumably by interfering with the interaction of VEGF with its receptor(s) (Gorski et al., 1999; Geng et al., 2001). Currently, however, effective strategies for enhancing the radiosensitivity of tumors in vivo by interfering with VEGF signal transduction are not available.

Recent evidence suggests that the cellular survival pathways involving VEGF and PI3K/Akt might overlap. For example, neovascular endothelial cells upregulate the expression of platelet-derived growth factor β receptors (βPDGFRs) during such processes as wound healing, inflammation, and glioma tumorigenesis (Wang et al., 1999). Treatment of these cells with PDGF increases the expression of VEGF, and this increase is dependent on PI3K (Wang et al., 1999). PI3K and Akt are also involved in the VEGF-induced up-regulation of intracellular adhesion molecule-1 (ICAM-1; Radisavljevic et al., 2000). Additionally, Akt has been shown to be involved in tumor-induced angiogenesis, an effect mediated through VEGF in conjunction with hypoxia-inducible factor-1α (HIF-1α; Gao et al., 2002). However, the involvement of the PI3K/Akt pathway in the generation of downstream signals for cellular survival induced by VEGF has not been established in vivo. And finally, prevention of radiation induced PI3K/Akt and MAPK signaling impacts upon the cytotoxic effects of this most commonly used form of cancer therapy (Schmidt-Ullrich et al., 2000; Geng et al., 2004; Tan & Hallahan, 2003; Tan et al., 2006; Yacoub et al., 2006).

Another obstacle to designing effective radiotherapy is that there is a poor correlation between cellular responses to ionizing radiation in vitro and in vivo. For example, glioblastoma multiforme (GBM) is insensitive to radiation treatment, and has a universally fatal clinical outcome in both children and adults (Walker et al., 1980; Wallner et al., 1989; Packer, 1999). In vitro studies, however, show that human GBM cell lines exhibit radiosensitivity that is similar to that seen in cell lines derived from more curable human tumors (Allam et al., 1993; Taghian et al., 1993). In accord with the clinical data, the use of in vivo animal models has shown that GBM tumors in vivo are much more radioresistant than the cell lines used to produce them are in vitro (Baumann et al., 1992; Allam et al., 1993; Taghian et al., 1993; Advani et al., 1998; Staba et al., 1998). Thus, the inability to predict the radiosensitivity of a tumor in vivo based upon in vitro experimentation continues to be a significant obstruction to the successful design of radiotherapy treatments of human cancers.

Tumor cells could show enhanced radiosensitivity in vitro compared to in vivo due to the absence of an angiogenic support network in vitro, the presence of which appears to contribute to a tumor's radioresistance in vivo. The response of tumor microvasculature to radiation is dependent upon the dose and time interval after treatment (Kallman et al., 1972; Song et al., 1972; Hilmas & Gillette, 1975; Johnson, 1976; Yamaura et al., 1976; Ting et al., 1991). Tumor blood flow decreases when high doses of radiation in the range of 20 Grays (Gy) to 45 Gy are used (Song et al., 1972). In contrast, blood flow increases when relatively low radiation doses, for example below 500 rads, are administered (Kallman et al., 1972; Hilmas & Gillette, 1975; Johnson, 1976; Yamaura et al., 1976; Gorski et al., 1999). In irradiated mouse sarcomas, for example, blood flow increased during the 3 to 7 days immediately following irradiation (Kallman et al., 1972). Thus, the microvasculature might serve to protect tumor cells from radiation-induced cell death.

Thus, there exists a long-felt need in the art for effective therapies for enhancing the efficacy of radiotherapy, particularly in the context of tumors that are resistant to radiotherapy. To address this need, the presently claimed subject matter provides methods for enhancing the radiosensitivity of cells in a target tissue via administration of an antagonist of a cytosolic phospholipase A2 biological activity.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for increasing the radiosensitivity of a target tissue in a subject. In some embodiments, the methods comprise administering a cytosolic phospholipase A2 ($cPLA_2$) antagonist, a vector encoding a cytosolic phospholipase A2 ($cPLA_2$) antagonist, or a combination thereof, to the subject, whereby the radiosensitivity of the target tissue is increased. In some embodiments, the target tissue is endothelial tissue. In some embodiments, the endothelial tissue is vascular endothelium. In some embodiments, the target tissue is a tumor. In some embodiments, the tumor comprises a radiation resistant tumor. In some embodiments, the target tissue comprises vasculature supplying blood flow to a tumor. In some embodiments, the subject is a mammal. In some embodiments, the administering a cytosolic phospholipase A2 ($cPLA_2$) antagonist comprises administering a minimally therapeutic dose of a $cPLA_2$ antagonist. In some embodiments, the administering comprises administering a composition comprising (a) a cytosolic phospholipase A2 ($cPLA_2$) antagonist, a vector encoding a cytosolic phospholipase A2 ($cPLA_2$) antagonist, or a combination thereof; and (b) a pharmaceutically acceptable carrier. In some embodiments, the cytosolic phospholipase A2 ($cPLA_2$) antagonist is selected from the group consisting of methyl arachidonyl fluorophosphonate (MAFP) and arachidonyl trifluoromethyl ketone ($AACOCF_3$). In some embodiments, the MAFP is administered in an amount ranging from about 0.01 to about 10 mg/kg. In some embodiments, the $AACOCF_3$ is administered in an amount ranging from 0.01 to about 50 mg/kg. In some embodiments. the cytosolic phospholipase A2 ($cPLA_2$) antagonist comprises a small interfering RNA (siRNA) targeted to a $cPLA_2$ gene product.

The presently disclosed subject matter also provides methods for suppressing tumor growth in a subject. In some embodiments, the methods comprise (a) administering a cytosolic phospholipase A2 ($cPLA_2$) antagonist, a vector encoding a cytosolic phospholipase A2 ($cPLA_2$) antagonist, or a combination thereof to a subject bearing a tumor to increase the radiosensitivity of the tumor; and (b) treating the tumor with ionizing radiation, whereby tumor growth is suppressed. In some embodiments, the subject is a mammal. In some embodiments, the administering a cytosolic phospholipase A2 ($cPLA_2$) antagonist comprises administering a minimally therapeutic dose of a $cPLA_2$ antagonist. In some embodiments, the administering a cytosolic phospholipase A2 ($cPLA_2$) antagonist comprises administering a composition comprising (a) a cytosolic phospholipase A2 ($cPLA_2$) antagonist, a vector encoding a cytosolic phospholipase A2 ($cPLA_2$) antagonist, or a combination thereof; and (b) a pharmaceutically acceptable carrier. In some embodiments, the cytosolic phospholipase A2 ($cPLA_2$) antagonist is selected from the group consisting of methyl arachidonyl fluorophosphonate (MAFP) and arachidonyl trifluoromethyl ketone ($AACOCF_3$). In some embodiments, the MAFP is administered in an amount ranging from 0.01 to about 10 mg/kg. In some embodiments, the $AACOCF_3$ is administered in an amount ranging from 0.01 to about 50 mg/kg. In some embodiments, the cytosolic phospholipase A2 ($cPLA_2$) antagonist is a small interfering RNA (siRNA) targeted to a $cPLA_2$ gene product. In some embodiments, the tumor comprises a radiation resistant tumor. In some embodiments, the treating the tumor with ionizing radiation comprises treating the tumor with a subtherapeutic dose of ionizing radiation.

The presently disclosed subject matter also provides methods for inhibiting tumor blood vessel growth. In some embodiments, the methods comprise (a) administering a cytosolic phospholipase A2 ($cPLA_2$) antagonist, a vector encoding a cytosolic phospholipase A2 ($cPLA_2$) antagonist, or a combination thereof to a subject bearing a tumor to increase the radiosensitivity of tumor blood vessels; and (b)

treating the tumor with ionizing radiation, whereby tumor blood vessel growth is inhibited. In some embodiments, the administering a cytosolic phospholipase A2 ($cPLA_2$) antagonist comprises administering a minimally therapeutic dose of a $cPLA_2$ antagonist. In some embodiments, the administering a cytosolic phospholipase A2 ($cPLA_2$) antagonist comprises administering a composition comprising (a) a cytosolic phospholipase A2 ($cPLA_2$) antagonist, a vector encoding a cytosolic phospholipase A2 ($cPLA_2$) antagonist, or a combination thereof; and (b) a pharmaceutically acceptable carrier. In some embodiments, the cytosolic phospholipase A2 ($cPLA_2$) antagonist is selected from the group consisting of methyl arachidonyl fluorophosphonate (MAFP) and arachidonyl trifluoromethyl ketone ($AACOCF_3$). In some embodiments, the MAFP is administered in an amount raging from 0.01 to about 10 mg/kg. In some embodiments, the $AACOCF_3$ is administered in an amount raging from 0.01 to about 50 mg/kg. In some embodiments, the cytosolic phospholipase A2 ($cPLA_2$) antagonist is a small interfering RNA (siRNA) targeted to a $cPLA_2$ gene product. In some embodiments, the subject is a mammal. In some embodiments, the tumor comprises a radiation resistant tumor. In some embodiments, the treating the tumor with ionizing radiation comprises treating the tumor with a subtherapeutic dose of ionizing radiation. In some embodiments, the presently disclosed methods further comprise reducing the vascular length density of the tumor blood vessels.

The presently disclosed subject matter also provides for the use of an antagonist of a cytosolic phospholipase A2 biological activity for enhancing the radiosensitivity of cells in a target tissue.

The presently disclosed subject matter also provides for the use of an antagonist of a cytosolic phospholipase A2 biological activity for the preparation of a medicament for enhancing the radiosensitivity of cells in a target tissue.

It is an object of the presently disclosed subject matter to provide methods for enhancing the efficacy of radiotherapy.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

The patent or application file contains at least one drawing executed in color. Copies of this patent or patent application publication with color drawing(s) will be provided by the United States Patent and Trademark Office upon request and payment of the necessary fee.

FIGS. 1A and 1B present results of HUVEC treated with 3 Gy and lysed 2-30 minutes after beginning of irradiation. FIG. 1A depicts Western blot analysis with phospho-specific antibodies to AktThr308/Ser473 or ERK1/2Thr202/Tyr204, total Akt or ERK1/2, and actin. FIG. 1B is a graph showing the enzymatic activity of PLA2 and SEM from three experiments.

FIGS. 1C and 1D present results of HUVEC treated with 3 Gy or in combination with $PLA_2$ inhibitors (1 μM arachidonyl trifluoromethyl ketone ($AACOCF_3$); 1 μM methyl arachidonyl fluorophosphonate, cytosolic $cPLA_2$ inhibitor (MAFP); 1 μM $PACOCF_3$; and 100 nM $sPLA_2I$), which were added 30 minutes before irradiation. Cells were lysed at 5 minutes (FIG. 1C) or 3 minutes (FIG. 1D) after beginning of irradiation. FIG. 1C depicts Western blot for phospho-Akt, phospho-ERK1/2, total Akt or ERK1/2, and actin. FIG. 1D is a graph showing the enzymatic activity of PLA2 and SEM from three experiments. *: $P<0.05$.

FIG. 1E depicts Western blot for $MEFcPLA_2\alpha^{+/+}$ and $MEFcPLA_2\alpha^{-/-}$ treated with 3 Gy and lysed 2-30 minutes after beginning irradiation. Shown is the Western blot for phospho-Akt, phospho-ERK1/2, total Akt or ERK1/2, and actin.

FIG. 2A depicts an autoradiograph of a TLC plate of extracted and standard lipids. FIG. 2B is a bar graph showing quantification of the average LPC production for each treatment with SEM of three experiments. *: P<0.05M. FIGS. 2C and 2D present a series of Western blots showing that LPC species and ionizing radiation lead to similar Akt and ERK1/2 activation in HUVEC. HUVEC were treated with 10 μM LPC. Cells were lysed either 5 minutes (FIG. 2C) or 10 minutes (FIG. 2D) later and subjected to Western blot analysis with phospho-specific antibodies to ERK1/2 (Thr202/Tyr204) or Akt (Thr308/Ser473), total ERK1/2 or Akt, and actin.

FIG. 3A is a graph of surviving fraction over time of HUVEC plated on Fibronectin-lined plates and irradiated. $cPLA_2$ inhibitors were added 30 minutes before irradiation. Two weeks after treatment, colonies were counted and normalized to plating efficiency. Shown are the surviving fractions and SEM from three experiments. *: $P<0.05$.

FIG. 3B is a series of Western blots utilizing anti-cyclin B1 and actin antibodies of HUVEC treated with EtOH or $cPLA_2$ inhibitors for 30 minutes, irradiated with 3 Gy, and lysed after 24 or 48 hours.

For FIGS. 3C-3E, HUVEC were grown on slides, treated with $cPLA_2$ inhibitors for 30 minutes, irradiated with 3 Gy, and fixed 24, 48, or 72 hours later. Fixed cells were stained with antibody to tubulin conjugated with FITC and DAPI. FIG. 3C depicts microscopic photographs of DAPI-stained cells 24 hours after treatment. FIG. 3D depicts microscopic photographs showing morphologies of a giant multinucleated cell and a cell of normal size. In FIG. 3E, multinucleated and giant cells were counted in multiple randomly selected fields. Shown is a bar graph of the counted cells for each treatment (average fold-increase over control with SEM from four experiments. *: $P<0.05$).

In FIGS. 4A and 4B, HUVEC were treated with EtOH or $cPLA_2$ inhibitors for 30 minutes and irradiated with 3 Gy. Cells were collected after 24, 48, 72, and 96 hours, stained with Annexin V-FITC and PI and analyzed by flow cytometry.

FIG. 4A depicts representative diagrams of the flow cytometry analysis of stained cells after 96 hours of treatment. FIG. 4B is a series of bar graphs showing the average fold increase in apoptotic cells in each treatment normalized to control cells ±SEM from four experiments. *: P<0.05.

In FIG. 4C, HUVEC were grown on slides, treated with $cPLA_2$ inhibitors for 30 minutes, irradiated with 3 Gy, fixed 24, 48, or 72 hours later, and stained with DAPI. Cells with chromatin condensation and nuclear fragmentation were counted in multiple randomly selected fields. FIG. 4C is a series of bar graphs showing the counted cells for each treatment (average fold-increase over control ±SEM from four experiments. *: P<0.05).

FIG. 8A is a bar graph showing the results of endothelial cell migration assays. Fresh complete HUVEC media was added to the bottom chamber of 6 well plates with 8.0 micron inserts, while HUVEC suspension was added to the top chamber. Both chambers were treated with EtOH or $cPLA_2$ inhibitors (1 μM $AACOCF_3$ and 1 μM MAFP) for 30 minutes and irradiated with 3 Gy. 24 hours later, cells in the insert chambers were stained with DAPI and counted (5 HPF per sample). The bar graph shows the mean and standard error of the mean (SEM) from six experiments for total number of migrated cells per HPF. *: P<0.05.

FIGS. 8B and 8C depict the results of endothelial cell gash closure assays. HUVEC were grown to 70-80% confluency. Four parallel wounds were created on each plate using a 200 ml pipette tip, and cells were treated with EtOH or $cPLA_2$ inhibitors (1 μM $AACOCF_3$ and 1 μM MAFP) for 30 minutes and irradiated with 3 Gy. 24 hours later, cells were stained with 1% methylene blue and counted. Shown are micrographs of stained cells (FIG. 8B) and a bar graph of the corresponding average percentage of migrated cells with SEM from six experiments (FIG. 8C). *: P<0.05.

FIGS. 8D and 8E depict the results of capillary tubule formation assays. HUVEC were cultured onto MATRIGEL™ for 30 minutes, treated with EtOH or $cPLA_2$ inhibitors (1 μM $AACOCF_3$ and 1 μM MAFP) for 30 minutes, and irradiated with 3 Gy. Tubules were counted under microscopy 24 hours later (5 high power fields (HPF) per sample). Shown are representative micrographs of capillary tubule formation (FIG. 8D) and total number of formed tubules per HPF in the bar graph with SEM from six experiments (FIG. 8E). *: P<0.05.

FIGS. 9A-9D depict the results of in vivo experiments in which LLC tumors were implanted into hind limb C57BL/6 mice. When tumors reached 2 mm, the mice received intraperitoneal injections of 70% EtOH or $cPLA_2$ inhibitor $AACOCF_3$ (10 mg/kg) followed by irradiation with 3 Gy for 5 consecutive days. After final treatment, the tumor vascularity was analyzed using Power Doppler sonography (FIGS. 9A and 9B) or staining of tumor histological sections with anti-vWF antibody (FIGS. 9C and 9D). Shown are representative sonograms (FIG. 9A) and a bar graph of the Vascular Index (VI, %I FIG. 9B). Also shown are micrographs of stained tumor sections (FIG. 9C) and a bar graph of the average number of vessels per HPF (6 HPF per sample; FIG. 9D).

FIGS. 9E and 9F are bar graphs showing fold change in tumor size in mice with LLC tumors and treated intraperitoneally (IP) with 70% EtOH or $cPLA_2$ inhibitors (FIG. 9E, 10 mg/kg $AACOCF_3$ or FIG. 9F, 2.0 mg/kg MAFP). Tumors were irradiated with 3 Gy 30 minutes after IP administration. Treatment was repeated daily for 5 consecutive days. Sizes of the tumors were measured using Power Doppler sonography on day 6 after tumor inoculation (first day of treatment) and on day 14 (FIG. 9E) or 17 (FIG. 9F). Shown are bar graphs of average fold-change in tumor size. All graphs are with SEM from at least three animals per group. *: P<0.05.

DETAILED DESCRIPTION

I. Definitions

Figure 1A:
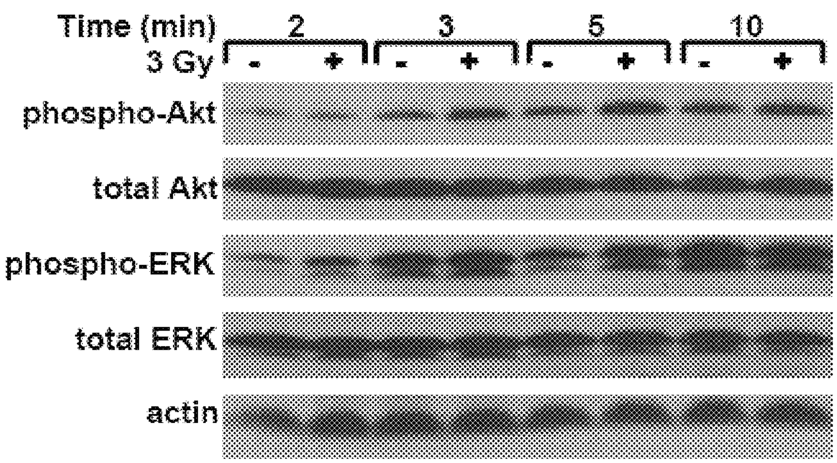
FIGS. 1A-1E present a series of Western blots and graphs demonstrating that cytosolic phospholipase A2 ($cPLA_2$) is required for radiation-induced ERK1/2 and Akt phosphorylation in irradiated cells.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" mean "one or more" when used in this application, including the claims. Thus, the phrase "a cell" refers to one or more cells, and can thus also refer to a tissue or an organ.

The term "about", as used herein when referring to a measurable value such as an amount of weight, time, dose (e.g. radiation dose), etc. is meant to encompass in some embodiments variations of ±20% or ±10%, in some embodiments ±5%, in some embodiments ±1%, in some embodiments ±0.1%, and in some embodiments ±0.01% from the specified amount, as such variations are appropriate to perform the disclosed methods.

The terms "nucleic acid molecule" and "nucleic acid" each refer to deoxyribonucleotides or ribonucleotides and polymers thereof in single-stranded, double-stranded, or triplexed form. Unless specifically limited, the term encompasses nucleic acids containing known analogues of natural nucleotides that have similar properties as the reference natural nucleic acid. The terms "nucleic acid molecule" and "nucleic acid" can also be used in place of "gene", "cDNA", or "mRNA". Nucleic acids of the presently claimed subject matter can be cloned, synthesized, recombinantly altered, mutagenized, or combinations thereof. Standard recombinant DNA and molecular cloning techniques used to isolate nucleic acids are known in the art. Site-specific mutagenesis to create base pair changes, deletions, or small insertions is also known in the art as exemplified by publications. See e.g., Sambrook & Russell, 2001; Silhavy et al., 1984; Glover & Hames, 1995; and Ausubel, 1995.

The term "substantially identical", as used herein to describe a degree of similarity between nucleotide sequences, refers to two or more sequences that have in some embodiments at least about least 60%, in another embodiment at least about 70%, in another embodiment at least about 80%, in another embodiment about 90% to about 99%, in another embodiment about 95% to about 99%, and in some embodiments about 99% nucleotide identity, when compared and aligned for maximum correspondence, as measured using a sequence comparison algorithm or by visual inspection. In some embodiments, the substantial identity exists in nucleotide sequences of at least about 100 residues, in some embodiments in nucleotide sequences of at least about 150 residues, and in some embodiments in nucleotide sequences comprising a full length coding sequence.

In some embodiments, substantially identical sequences can comprise polymorphic sequences. The term "polymorphic" refers to the occurrence of two or more genetically determined alternative sequences or alleles in a population. An allelic difference can be as small as one base pair. In some embodiments, substantially identical sequences can comprise mutagenized sequences, including sequences comprising silent mutations. A mutation can comprise a single base change.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

In some embodiments, a nucleotide sequence employed for hybridization studies or assays includes probe sequences that are complementary to or mimic at least an about 14 to 40 nucleotide sequence of a nucleic acid molecule of the presently claimed subject matter. In some embodiments, probes comprise 14 to 20 nucleotides, or even longerwhere desired, such as 30, 40, 50, 60, 100, 200, 300, or 500 nucleotides or up to the full length of any one of the sequences of the presently claimed subject matter. Such probes can be readily prepared by, for example, chemical synthesis of the fragment, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent hybridization and wash conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook & Russell, 2001 for a description of SSC buffer. Often, a high stringency wash is preceded by a low stringency wash to remove background probe signal. An example of medium stringency wash conditions for a duplex of more than about 100 nucleotides is 15 minutes in 1×SSC at 45° C. An example of low stringency wash for a duplex of more than about 100 nucleotides is 15 minutes in 4× to 6×SSC at 40° C. For short probes (e.g., about 10 to 50 nucleotides), stringent conditions typically involve salt concentrations of less than about 1 M $Na^+$ ion, typically about 0.01 to 1 M $Na^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are additional examples of hybridization and wash conditions that can be used to identify nucleotide sequences that are substantially identical to reference nucleotide sequences of the presently claimed subject matter: a probe nucleotide sequence in one example hybridizes to a target nucleotide sequence in 7% sodium dodecyl sulfate (SDS), 0.5M $NaPO_4$, 1 mM EDTA at 50° C. followed by washing in 2×SSC, 0.1% SDS at 50° C.; in another example, a probe and target sequence hybridize in 7% sodium dodecyl sulfate (SDS), 0.5M $NaPO_4$, 1 mM EDTA at 50° C. followed by washing in 1×SSC, 0.1% SDS at 50° C.; in another example, a probe and target sequence hybridize in 7% sodium dodecyl sulfate (SDS), 0.5M $NaPO_4$, 1 mM EDTA at 50° C. followed by washing in 0.5×SSC, 0.1% SDS at 50° C.; in another example, a probe and target sequence hybridize in 7% sodium dodecyl sulfate (SDS), 0.5M $NaPO_4$, 1 mM EDTA at50° C. followed by washing in 0.1×SSC, 0.1% SDS at 50° C.; in another example, a probe and target sequence hybridize in 7% sodium dodecyl sulfate (SDS), 0.5M $NaPO_4$, 1 mM EDTA at 50° C. followed by washing in 0.1×SSC, 0.1% SDS at 65° C.

A further indication that two nucleic acid sequences are substantially identical is that the proteins encoded by the nucleic acids are substantially identical, share an overall three-dimensional structure, or are biologically functional equivalents. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term “conservatively substituted variants” refers to nucleic acid sequences having degenerate codon substitutions wherein the third position of one or more selected (or all) codons is substituted with mixed-base and/or deoxyinosine residues (Ohtsuka et al., 1985; Batzer et al., 1991; Rossolini et al., 1994).

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. See e.g., Kyte & Doolittle, 1982. It is known that certain amino acids can be substituted for other amino acids having a similar hydropathic index or score and still retain a similar biological activity. In making changes based upon the hydropathic index, one example involves the substitution of amino acids whose hydropathic indices are within ±2 of the original value, another example involves those that are within ±1 of the original value, and yet another example involves those within ±0.5 of the original value.

It is also understood in the art that the substitution of like amino acids can be made effectively based on hydrophilicity. U.S. Pat. No. 4,554,101 describes that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, one example involves the substitution of amino acids whose hydrophilicity values are within ±2 of the original value, another example involves those that are within ±1 of the original value, and still another example involves those within ±0.5 of the original value.

The term “subsequence” refers to a sequence of nucleic acids that comprises a part of a longer nucleic acid sequence. An exemplary subsequence is a probe, described herein above, or a primer. The term “primer” as used herein refers to a contiguous sequence comprising in one example about 8 or more deoxyribonucleotides or ribonucleotides, in another example 10-20 nucleotides, and in still another example 20-30 nucleotides of a selected nucleic acid molecule. The primers of the presently claimed subject matter encompass oligonucleotides of sufficient length and appropriate sequence so as to provide initiation of polymerization on a nucleic acid molecule of the presently claimed subject matter.

The term “complementary sequences”, as used herein, indicates two nucleotide sequences that comprise antiparallel nucleotide sequences capable of pairing with one another upon formation of hydrogen bonds between base pairs. As used herein, the term “complementary sequences” means nucleotide sequences which are substantially complementary, as can be assessed by the same nucleotide comparison set forth above, or is defined as being capable of hybridizing to the nucleic acid segment in question under relatively stringent conditions such as those described herein. An example of a complementary nucleic acid segment is an antisense oligonucleotide.

The term “gene” refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term “operatively linked”, as used herein, refers to a functional combination between a promoter region and a nucleotide sequence such that the transcription of the nucleotide sequence is controlled and regulated by the promoter region. Techniques for operatively linking a promoter region to a nucleotide sequence are known in the art.

The term “heterologous”, as used herein to refer to a promoter or any other nucleic acid, refers to a sequence that originates from a source foreign to an intended host cell or, if from the same source, is modified from its original form. Thus, a heterologous nucleic acid in a host cell includes a gene that is endogenous to the particular host cell but has been modified, for example by mutagenesis or by isolation from native cis-regulatory sequences. The term “heterologous nucleic acid” also includes non-naturally occurring multiple copies of a native nucleotide sequence. The term “heterologous nucleic acid” also encompasses a nucleic acid that is incorporated into a host cell's nucleic acids, however at a position wherein such nucleic acids are not ordinarily found. A representative heterologous nucleic acid comprises a recombinant nucleic acid, as described further herein below.

The term “recombinant” generally refers to an isolated nucleic acid that is replicable in a non-native environment. Thus, a recombinant nucleic acid can comprise a non-replicable nucleic acid in combination with additional nucleic acids, for example vector nucleic acids, which enable its replication in a host cell.

The term “vector” is used herein to refer to a nucleic acid molecule having nucleotide sequences that enable its replication in a host cell. A vector can also include nucleotide sequences to permit ligation of nucleotide sequences within the vector, wherein such nucleotide sequences are also replicated in a host cell. Representative vectors include plasmids, cosmids, and viral vectors. A vector can also mediate recombinant production of a soluble peptide or polypeptide of the presently disclosed subject matter.

The term “construct”, as used herein to describe an expression construct, refers to a vector further comprising a nucleotide sequence operatively inserted with the vector, such that the nucleotide sequence is expressed.

The terms “recombinantly expressed” or “recombinantly produced” are used interchangeably to generally refer to the process by which a polypeptide encoded by a recombinant nucleic acid is produced.

The term “heterologous expression system” refers to a host cell comprising a heterologous nucleic acid and the polypeptide encoded by the heterologous nucleic acid. For example, a heterologous expression system can comprise a host cell transfected with a construct comprising a recombinant nucleic acid, or a cell line produced by introduction of heterologous nucleic acids into a host cell genome.

II. Radiosensitivity

In some embodiments, a novel method for increasing the radiosensitivity of a target tissue in a subject via administration of a cytosolic phospholipase A2 ($cPLA_2$) antagonist is provided. The method comprises administering a $cPLA_2$ antagonist to the subject, whereby the radiosensitivity of a target tissue is increased. The presently described subject matter also provides a method for suppressing tumor growth in a subject. The method comprises: (a) administering a cytosolic phospholipase A2 ($cPLA_2$) antagonist to a subject bearing a tumor to increase the radiosensitivity of the tumor; and (b) treating the tumor with ionizing radiation, whereby tumor growth is suppressed. The presently claimed subject matter also provides a method for inhibiting tumor blood vessel growth. The method comprises: (a) administering a cytosolic phospholipase A2 ($cPLA_2$) antagonist to a subject bearing a tumor to increase the radiosensitivity of tumor blood vessels; and (b) treating the tumor with ionizing radiation, whereby tumor blood vessel growth is inhibited.

The term “radiosensitivity” as used herein to describe a target tissue refers to a quality of susceptibility to treatment using ionizing radiation. This susceptibility can result from direct effects of the radiation on the cells of the target tissue themselves. For example, radiation can cause the cells of the target tissue to undergo apoptosis as a result of either DNA damage or another cell autonomous mechanism. Alternatively, radiosensitivity can result from indirect effects, such as effects on the microenvironment of the cells of the target tissue, for example, on the blood vessels supplying nutrients and oxygen to the target tissue. Thus, radiotherapy can be used to suppress the growth of a radiosensitive target tissue.

Radiosensitivity can be quantified by determining a minimal amount of ionizing radiation that can be used to delay target tissue growth. Thus, the term “radiosensitivity” refers to a quantitative range of radiation susceptibility.

The term “target tissue” refers to any cell or group of cells present in a subject. This term includes single cells and populations of cells. The term includes but is not limited to cell populations comprising glands and organs such as skin, liver, heart, kidney, brain, pancreas, lung, stomach, and reproductive organs. It also includes but is not limited to mixed cell populations such as bone marrow. Further, it includes but is not limited to such abnormal cells as neoplastic or tumor cells, whether individually or as a part of solid or metastatic tumors. The term “target tissue” as used herein additionally refers to an intended site for accumulation of a $cPLA_2$ antagonist following administration to a subject. For example, the methods of the presently claimed subject matter employ a target tissue comprising a tumor and/or the vasculature providing oxygen to a tumor.

The term “suppressing tumor growth” refers to an increase in a duration of time required for a tumor to grow a specified amount. For example, treatment can extend the time required for a tumor to increase in volume 3-fold relative to an initial day of measurement (day 0) or the time required to grow to a volume of 1 $cm^3$.

The terms “radiation resistant tumor” and “radioresistant tumor” each generally refer to a tumor that is substantially unresponsive to radiotherapy when compared to other tumors. Representative radiation resistant tumor models include glioblastoma multiforme and melanoma.

The term “increase” as used herein to refer to a change in radiosensitivity of a tumor refers to change that renders a tumor more susceptible to destruction by ionizing radiation. Alternatively stated, an increase in radiosensitivity refers to a decrease in the minimal amount of ionizing radiation that effectively suppresses tumor growth. An increase in radiosensitivity can also comprise suppressed tumor growth or inhibited tumor blood vessel growth when a cytosolic phospholipase A2 ($cPLA_2$) antagonist is administered with radiation as compared to a same dose of radiation alone. In one example, an increase in radiosensitivity refers to an increase of at least about 2-fold, in another example to an increase of at least about 5-fold, and in still another example an increase of at least 10-fold. In some embodiments of the presently claimed subject matter, an increase in radiosensitivity comprises a transformation of a radioresistant tumor to a radiosensitive tumor.

The methods of the presently claimed subject matter are useful for increasing the radiosensitivity of a target tissue, for suppressing tumor growth, and/or for inhibiting tumor blood vessel growth in any subject. Thus, the term “subject” as used herein includes any vertebrate species, for example, warm-blooded vertebrates such as mammals and birds. More particularly, the methods of the presently claimed subject matter are provided for the treatment of tumors in mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants and livestock (such as cattle, oxen, sheep, giraffes, deer, goats, bison, and camels), and horses. Also provided is the treatment of birds, including those kinds of birds that are endangered or kept in zoos, as well as fowl, and more particularly domesticated fowl or poultry, such as turkeys, chickens, ducks, geese, guinea fowl, and the like, as they are also of economic importance to humans.

The term “tumor” as used herein encompasses both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi’s sarcoma); brain, nerves, eyes, and meninges (e.g., astrocytomas, gliomas, glioblastomas, retinoblastomas, neuromas, neuroblastomas, Schwannomas and meningiomas). The term “tumor” also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin’s and non-Hodgkin’s lymphomas.

The term “tumor” also encompasses radioresistant tumors, including radioresistant variants of the any of the tumor listed above.

III. Cytosolic Phospholipase A2 ($cPLA_2$) Antagonists

The presently claimed subject matter provides methods for increasing the radiosensitivity of a target tissue via administration of a cytosolic phospholipase A2 ($cPLA_2$) antagonist. Any suitable cytosolic phospholipase A2 ($cPLA_2$) antagonist can be used in accordance with the methods of the presently claimed subject matter, wherein the antagonist has a capacity to increase the radiosensitivity of a target tissue. In some embodiments, a cytosolic phospholipase A2 ($cPLA_2$) antagonist also shows anti-angiogenic activity or angiostatic activity.

The term “$cPLA_2$ antagonist” as used herein refers to a molecule or other chemical entity having a capacity for specifically binding to $cPLA_2$ to thereby inhibit a $cPLA_2$ biological activity. $cPLA_2$ antagonists include but are not limited to small molecule inhibitors, neutralizing antibodies, and nucleic acid-based antagonists (e.g., siRNAs directed against a $cPLA_2$ gene product).

The term “$cPLA_2$” refers to a cytosolic phospholipase A2 (Gene Symbol PLA2G4A), which is a cytoplasmic enzyme that catalyzes the hydrolysis of membrane phospholipids to release fatty acid (e.g., arachidonic acid), which is subsequently metabolized into eicosanoids. $cPLA_2$ nucleotide and amino acid sequences from several species have been determined, a non-limiting subset of which are set forth in Table 1.

TABLE 1

$cPLA_2$ GENBANK ® Sequences

| Organism | Nucleic Acid Accession No. | Amino Acid Accession No. |
|---|---|---|
| *Homo sapiens* | NM_024420 (IVA) | NP_077734 (IVA) |
| | NM_003706 (IVC) | NP_003697 (IVC) |
| *Pongo pygmaeus* | CR859848 | CAH92005 |
| *Mus musculus* | NM_008869 IVA) | NP_032895 (IVA) |
| *Rattus norvegicus* | NM_133551 (IVA) | NP_598235 (IVA) |
| | NM_005090 (IVB) | NP_005081 (IVB) |
| *Bos Taurus* | NP_001069332 | NM_001075864 |
| *Canis familiaris* | XM_537170 | XP_537170 |
| *Danio rerio* | NM_131295 | NP_571370 |
| *Equus caballus* | NM_001081843 | NP_001075312 |
| *Gallus gallus* | NM_205423 | NP_990754 |
| *Oryctolagus cuniculus* | NM_001082072 | NP_001075541 |
| *Xenopus laevis* | BC056041 | AAH56041 |

The term “binding” refers to an affinity between two molecules, for example, an inhibitor and a target molecule. As used herein, “specific binding” means a preferential binding of one molecule for another in a mixture of molecules. The binding of an inhibitor to a target molecule can be considered specific if the binding affinity is about $1\times10^4$ $M^{-1}$ to about $1\times10^6$ $M^{-1}$ or greater.

III.A. Small Molecules

The term “small molecule” as used herein refers to a compound, for example an organic compound, with a molecular weight of in one example less than about 1,000 daltons, in another example less than about 750 daltons, in another example less than about 600 daltons, and in still another example less than about 500 daltons. A small molecule also in one example has a computed log octanol—water partition coefficient in the range of about −4 to about +14, and in another example in the range of about −2 to about +7.5.

Arachidonyl trifluoromethyl ketone ($AACOCF_3$; available from United States Biological Inc., Swampscott, Mass., United States of America) and methyl arachidonyl fluorophosphonate (MAFP; available from Cayman Chemical Company, Ann Arbor, Mich., United States of America) are small molecule antagonists of $cPLA_2$ (Riendeau et al., 1994; Lio et al., 1996). Additional small molecule inhibitors of $cPLA_2$ are disclosed in U.S. Pat. Nos. 6,500,853; 6,635,771; 6,797,708; and 6,924,391.

III.B. $cPLA_2$ Antibodies

The presently claimed subject matter further provides a $cPLA_2$ antagonist comprising an antibody that specifically binds $cPLA_2$. Optionally, a $cPLA_2$ antagonist can further comprise a carrier for sustained bioavailability of the antibody at a tumor. The disclosure herein reveals that a prolonged or sustained release of $cPLA_2$ antagonist is optionally employed to enhance the therapeutic effect of combined $cPLA_2$ antagonism and radiation.

The term “antibody” indicates an immunoglobulin protein, or functional portion thereof, including a polyclonal antibody, a monoclonal antibody, a chimeric antibody, a hybrid antibody, a single chain antibody (e.g., a single chain antibody represented in a phage library), a mutagenized antibody, a humanized antibody, and antibody fragments that comprise an antigen binding site (e.g., Fab and Fv antibody fragments). In some embodiments, an antibody of the presently claimed subject matter is a monoclonal antibody.

Techniques for preparing and characterizing antibodies are known in the art. See e.g., Harlow & Lane, 1988 and U.S. Pat. Nos. 4,196,265; 4,946,778; 5,091,513; 5,132,405; 5,260,203; 5,677,427; 5,892,019; 5,985,279; 6,054,561. Single chain antibodies can be identified by screening a phage antibody library, for example as described by U.S. Pat. Nos. 6,174,708; 6,057,098; 5,922,254; 5,840,479; 5,780,225; 5,702,892; and 5,667,988.

An antibody of the presently claimed subject matter can further be mutagenized or otherwise modified to improve antigen binding and/or antibody stability. For example, to prevent undesirable disulfide bond formation, a nucleotide sequence encoding the variable domain of an antibody or antibody fragment can be modified to eliminate at least one of each pair of codons that encode cysteines for disulfide bond formation. Recombinant expression of the modified nucleotide sequence, for example in a prokaryotic expression system, results in an antibody having improved stability. See U.S. Pat. No. 5,854,027.

III.C. Aptamers

In some embodiments, a $cPLA_2$ antagonist comprises an aptamer that specifically binds to a $cPLA_2$ polypeptide. As used herein, “aptamer” refers in general to either an oligonucleotide of a single defined sequence or a mixture of said oligonucleotides, wherein the mixture retains the properties of binding specifically to the target molecule. Thus, as used herein “aptamer” denotes both singular and plural sequences of oligonucleotides, as defined hereinabove. The term “aptamer” is meant to refer to a single- or double-stranded nucleic acid which is capable of binding to a protein or other molecule, and thereby disturbing the protein’s or other molecule’s function.

In general, aptamers comprise in some embodiments about 10 to about 100 nucleotides, in some embodiments about 15 to about 40 nucleotides, in some embodiments about 20 to about 40 nucleotides, in that oligonucleotides of a length that falls within these ranges are readily prepared by conventional techniques. Optionally, aptamers can further comprise in some embodiments a minimum of approximately 6 nucleotides, in some embodiments 10, and in some embodiments 14 or 15 nucleotides, that are necessary to effect specific binding. The only apparent limitations on the binding specificity of the target/loligonucleotide couples of the presently disclosed subject matter concern sufficient sequence to be distinctive in the binding oligonucleotide and sufficient binding capacity of the target substance to obtain the necessary interaction. Aptamers of binding regions containing sequences shorter than 10, e.g., 6-mers, are feasible if the appropriate interaction can be obtained in the context of the environment in which the target is placed. Thus, if there is little interference by other materials, less specificity and less strength of binding can be required.

Aptamers and how to isolate aptamers that bind to specific targets are disclosed in U.S. Patent Application Publication No. 20030175703 and U.S. Pat. Nos. 5,270,163; 5,567,588; 5,683,867; 6,706,482; 6,855,496; and 7,176,295, the disclosure of each of which is hereby incorporated by reference in its entirety.

III.D. RNAi-based $cPLA_2$ Antagonists

In some embodiments, the presently disclosed subject matter takes advantage of the ability of short, double stranded RNA molecules to cause the down regulation of cellular genes, a process referred to as RNA interference (RNAi). As used herein, "RNA interference" and "RNAi" refer to a process of sequence-specific post-transcriptional gene silencing mediated by a small interfering RNA (siRNA). See generally Fire et al., 1998; U.S. Pat. No. 6,506,559. The process of post-transcriptional gene silencing is thought to be an evolutionarily conserved cellular defense mechanism that has evolved to prevent the expression of foreign genes (Fire, 1999).

The presence of dsRNA in cells triggers various responses, one of which is RNAi. RNAi appears to be different from the interferon response to dsRNA, which results from dsRNA-mediated activation of an RNA-dependent protein kinase (PKR) and 2',5'-oligoadenylate synthetase, resulting in non-specific cleavage of mRNA by ribonuclease L.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA; Bernstein et al., 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., 2001 b).

RNAi has been described in several cell type and organisms. Fire et al., 1998 described RNAi in *C. elegans*. Wianny & Zernicka-Goetz, 1999 disclose RNAi mediated by dsRNA in mouse embryos. Hammond et al., 2000 were able to induce RNAi in *Drosophila* cells by transfecting dsRNA into these cells. Elbashir et al. 2001a discloses the presence of RNAi in cultured mammalian cells including human embryonic kidney and HeLa cells by the introduction of duplexes of synthetic 21 nucleotide RNAs.

Experiments using *Drosophila* embryonic lysates revealed certain aspects of siRNA length, structure, chemical composition, and sequence that are involved in RNAi activity. See Elbashir et al., 2001c. In the disclosed assay, 21 nucleotide siRNA duplexes were most active when they contain 3'-overhangs of two nucleotides. Also, the position of the cleavage site in the target RNA was shown to be defined by the 5'-end of the siRNA guide sequence rather than the 3'-end (Elbashir et al., 2001 b).

Other studies have indicated that a 5'-phosphate on the target-complementary strand of a siRNA duplex is required for siRNA activity and that ATP is utilized to maintain the 5-phosphate moiety on the siRNA (Nykanen et al., 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359,180).

Other references disclosing the use of dsRNA and RNAi include PCT International Publication Nos. WO 01/75164 (in vitro RNAi system using cells from *Drosophila* and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi).

In some embodiments, the $cPLA_2$ antagonist comprises an siRNA construct targeted to or against a $cPLA_2$ gene product (e.g., a subsequence of an RNA molecule transcribed from a $cPLA_2$ gene).

As used herein, the phrase "target RNA" refers to an RNA molecule (for example, an mRNA molecule encoding a $cPLA_2$ gene product) that is a target for downregulation. Similarly, the phrase "target site" refers to a sequence within a target RNA that is "targeted" for cleavage mediated by an siRNA construct that contains sequences within its antisense strand that are complementary to the target site. Also similarly, the phrase "target cell" refers to a cell that expresses a target RNA and into which an siRNA is intended to be introduced. A target cell is in some embodiments a cell in a subject. For example, a target cell can comprise a tumor cell and/or a cell in tumor vasculature that expresses a $cPLA_2$ gene. Non-limiting examples of sequences encoding target RNA molecules of the presently disclosed subject matter are presented in Table 1.

As used herein, the phrase "detectable level of cleavage" refers to a degree of cleavage of target RNA (and formation of cleaved product RNAs) that is sufficient to allow detection of cleavage products above the background of RNAs produced by random degradation of the target RNA. Production of siRNA-mediated cleavage products from at least 1-5% of the target RNA is sufficient to allow detection above background for most detection methods.

The terms "small interfering RNA", "short interfering RNA", and "siRNA" are used interchangeably and refer to any nucleic acid molecule capable of mediating RNA interference (RNAi) or gene silencing. See e.g., Bass, 2001; Elbashir et al., 2001a; and PCT International Publication Nos. WO 00/44895, WO 01/36646, WO 99/32619, WO 00/01846, WO 01/29058, WO 99/07409, and WO 00/44914. In some embodiments, the siRNA comprises a double stranded polynucleotide molecule comprising complementary sense and antisense regions, wherein the antisense region comprises a sequence complementary to a region of a target nucleic acid molecule (for example, an mRNA encoding a $cPLA_2$ polypeptide). In some embodiments, the siRNA comprises a single stranded polynucleotide having self-complementary sense and antisense regions, wherein the antisense region comprises a sequence complementary to a region of a target nucleic acid molecule. In some embodiments, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

Figure 7:
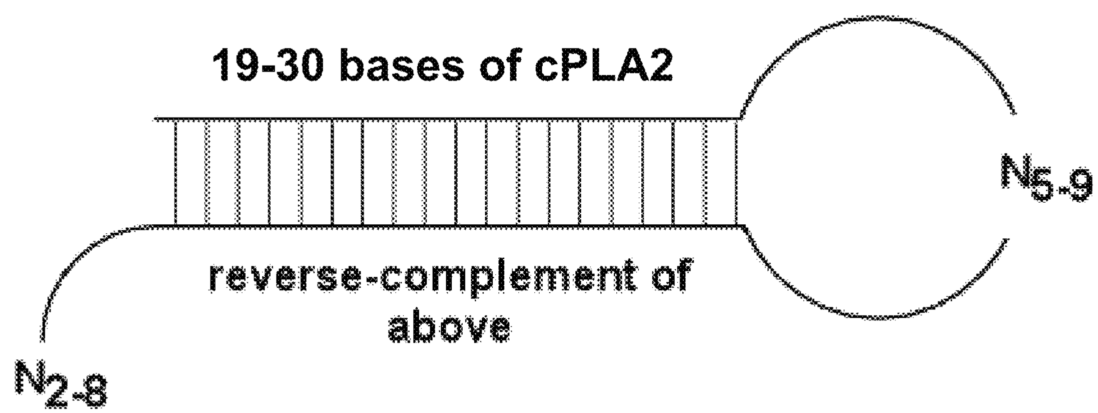
FIG. 7 depicts a general structure for an siRNA molecule of the presently disclosed subject matter. For the double-stranded molecule shown in FIG. 7, N can be any nucleotide, provided that in the loop structure identified as $N_{5-9}$, all 5-9 nucleotides remain in a single-stranded conformation. Similarly, $N_{2-8}$ can be any sequence of 2-8 nucleotides or modified nucleotides, provided that the nucleotides remain in a single-stranded conformation in the siRNA molecule.

The siRNA molecules of the presently disclosed subject matter include, but are not limited to an siRNA molecule of the general structure depicted in FIG. 7. For the double-stranded molecule shown in FIG. 7, N can be any nucleotide, provided that in the loop structure identified as $N_{5-9}$, all 5-9 nucleotides remain in a single-stranded conformation. Similarly, $N_{2-8}$ can be any sequence of 2-8 nucleotides or modified nucleotides, provided that the nucleotides remain in a single-stranded conformation in the siRNA molecule. The duplex represented in FIG. 7 as "19-30 bases of $cPLA_2$" can be formed using any contiguous 19-30 base sequence of one of the $cPLA_2$ gene products disclosed herein (for example, in Table 1). In constructing an siRNA molecule of the presently disclosed subject matter, this 19-30 base sequence is followed (in a 5' to 3' direction) by 5-9 random nucleotides ($N_{5-9}$ above), the reverse-complement of the 19-30 base sequence, and finally 2-8 random nucleotides ($N_{2-8}$ above).

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell can also affect gene expression as defined herein.

As used herein, the term "modulate" refers to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" or "suppress", but the use of the word "modulate" is not limited to this definition.

As used herein, the terms "inhibit", "suppress", "down regulate", and grammatical variants thereof are used interchangeably and refer to an activity whereby gene expression or a level of an RNA encoding one or more gene products is reduced below that observed in the absence of a nucleic acid molecule of the presently disclosed subject matter. In some embodiments, inhibition with an siRNA molecule results in a decrease in the steady state level of a target RNA. In some embodiments, inhibition with a siRNA molecule results in an expression level of a target gene that is below that level observed in the presence of an inactive or attenuated molecule that is unable to mediate an RNAi response. In some embodiments, inhibition of gene expression with an siRNA molecule of the presently disclosed subject matter is greater in the presence of the siRNA molecule than in its absence. In some embodiments, inhibition of gene expression is associated with an enhanced rate of degradation of the mRNA encoded by the gene (for example, by RNAi mediated by an siRNA).

As used herein, the terms "gene" and "target gene" refer to a nucleic acid that encodes an RNA, for example, nucleic acid sequences including, but not limited to, structural genes encoding a $cPLA_2$ polypeptide. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence. In some embodiments, a gene is a $cPLA_2$ gene. Representative $cPLA_2$ genes correspond to the sequences set forth in Table 1, although this list is not intended to be exhaustive.

As is understood in the art, a gene comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed (e.g., RNAi activity. For example, the degree of complementarity between the sense and antisense strands of the siRNA construct can be the same or different from the degree of complementarity between the antisense strand of the siRNA and the target nucleic acid sequence. Complementarity to the target sequence of less than 100% in the antisense strand of the siRNA duplex, including point mutations, is not well tolerated when these changes are located between the 3'-end and the middle of the antisense siRNA, whereas mutations near the 5'-end of the antisense siRNA strand can exhibit a small degree of RNAi activity (Elbashir et al., 2001c). Determination of binding free energies for nucleic acid molecules is well known in the art. See e.g., Freier et al., 1986; Turner et al., 1987.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence.

The siRNA molecules of the presently disclosed subject matter can be added directly to a cell, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation into biopolymers. The siRNA molecule of the presently disclosed subject matter can be encoded by a recombinant vector (for example, a viral vector).

As used herein, the term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of the siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

As used herein, the phrase "double stranded RNA" refers to an RNA molecule at least a part of which is in Watson-Crick base pairing forming a duplex. As such, the term is to be understood to encompass an RNA molecule that is either fully or only partially double stranded. Exemplary double stranded RNAs include, but are not limited to molecules comprising at least two distinct RNA strands that are either partially or fully duplexed by intermolecular hybridization. Additionally, the term is intended to include a single RNA molecule that by intramolecular hybridization can form a double stranded region (for example, a hairpin). Thus, as used herein the phrases "intermolecular hybridization" and "intramolecular hybridization" refer to double stranded molecules for which the nucleotides involved in the duplex formation are present on different molecules or the same molecule, respectively.

As used herein, the phrase "double stranded region" refers to any region of a nucleic acid molecule that is in a double stranded conformation via hydrogen bonding between the nucleotides including, but not limited to hydrogen bonding between cytosine and guanosine, adenosine and thymidine, adenosine and uracil, and any other nucleic acid duplex as would be understood by one of ordinary skill in the art. The length of the double stranded region can vary from about 15 consecutive basepairs to several thousand basepairs. In some embodiments, the double stranded region is at least 15 basepairs, in some embodiments between 15 and 50 basepairs, and in some embodiments between 15 and 30 basepairs. In some embodiments, the length of the double stranded region is selected from the group consisting of 19, 20, 21, 22, 23, 24, 25, 26, 27, 28, 29, and 30 basepairs. In some embodiments, the double stranded region comprises a first strand comprising a ribonucleotide sequence that corresponds to a coding strand of the $cPLA_2$ gene and a second strand comprising a ribonucleotide sequence that is complementary to the first strand, and wherein the first strand and the second strand hybridize to each other to form the double-stranded molecule. As used herein, the terms "corresponds to", "corresponding to", and grammatical variants thereof refer to a nucleotide sequence that is 100% identical to at least 19 contiguous nucleotides of a nucleic acid sequence of a $cPLA_2$ gene. Thus, a first nucleic acid sequence that "corresponds to" a coding strand of a $cPLA_2$ gene is a nucleic acid sequence that is 100% identical to at least 19 contiguous nucleotides of a $cPLA_2$ gene, including, but note limited to 5' untranslated sequences, exon sequences, intron sequences, and 3' untranslated sequences.

In a representative embodiment, the length of the double stranded region is 19 basepairs. As describe hereinabove, the formation of the double stranded region results from the hybridization of complementary RNA strands (for example, a sense strand and an antisense strand), either via an intermolecular hybridization (i.e. involving 2 or more distinct RNA molecules) or via an intramolecular hybridization, the latter of which can occur when a single RNA molecule contains self-complementary regions that are capable of hybridizing to each other on the same RNA molecule. These self-complementary regions are typically separated by a short stretch of nucleotides (for example, about 5-10 nucleotides) such that the intramolecular hybridization event forms what is referred to in the art as a "hairpin".

The nucleic acid molecules of the presently disclosed subject matter individually, or in combination or in conjunction with other drugs, can be used to treat diseases or conditions discussed herein. For example, to treat a particular disease or condition, the siRNA molecules can be administered to a subject or can be administered to other appropriate cells evident to those skilled in the art, individually or in combination with one or more drugs under conditions suitable for the treatment.

The term "nucleic acid molecule" refers to deoxyribonucleotides or ribonucleotides and polymers thereof in either single- or double-stranded form. Unless specifically limited, the term encompasses nucleic acids containing known analogues of natural nucleotides that have similar properties as the reference natural nucleic acid. Unless otherwise indicated, a particular nucleotide sequence also implicitly encompasses complementary sequences, subsequences, elongated sequences, as well as the sequence explicitly indicated. The terms "nucleic acid molecule" or "nucleotide sequence" can also be used in place of "gene", "DNA", "cDNA", "RNA", or "mRNA". Nucleic acids can be derived from any source, including any organism.

An exemplary nucleotide sequence employed in the methods disclosed herein comprises sequences that are complementary to each other, the complementary regions being capable of forming a duplex of in some embodiments at least about 15 to 50 basepairs. One strand of the duplex comprises a nucleic acid sequence of at least 15 contiguous bases having a nucleic acid sequence of a nucleic acid molecule of the presently disclosed subject matter (for example, those nucleic acid sequences that correspond to the GENBANK® Accession Nos. set forth in Table 1). In some embodiments, one strand of the duplex comprises a nucleic acid sequence comprising 15 to 18 nucleotides, or even longer where desired, such as 19, 20, 21, 22, 23, 24, 25, 26, 27, 28, 29, or 30 nucleotides or up to the full length of any of those nucleic acid sequences that correspond to the GENBANK® Accession Nos. set forth in Table 1, or any other $cPLA_2$ transcription product. Such fragments can be readily prepared by, for example, directly synthesizing the fragment by chemical synthesis, by application of nucleic acid amplification technology, or by introducing selected sequences into recombinant vectors for recombinant production. The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The term "subsequence" refers to a sequence of nucleic acids that comprises a part of a longer nucleic acid sequence. An exemplary subsequence is a sequence that comprises part of a duplexed region of an siRNA, one strand of which is complementary to the sequence of an mRNA.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The terms "operatively linked" and "operably linked", as used herein, refer to a promoter region that is connected to a nucleotide sequence in such a way that the transcription of that nucleotide sequence is controlled and regulated by that promoter region. Similarly, a nucleotide sequence is said to be under the "transcriptional control" of a promoter to which it is operably linked. Techniques for operatively linking a promoter region to a nucleotide sequence are known in the art.

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

The term "expression vector" as used herein refers to a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

The term "promoter" or "promoter region" each refers to a nucleotide sequence within a gene that is positioned 5' to a coding sequence of a same gene and functions to direct transcription of the coding sequence. The promoter region comprises a transcriptional start site, and can additionally include one or more transcriptional regulatory elements. In some embodiments, a method of the presently disclosed subject matter employs a hypoxia inducible promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the CMV minimal promoter, the HSV-tk minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operably linked gene. For example, cell-type-specific or tissue-specific transcriptional regulatory elements can be added to minimal promoters to create recombinant promoters that direct transcription of an operably linked nucleotide sequence in a cell-type-specific or tissue-specific manner Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the β-actin promoter (see e.g., Williams et al., 1993), and other constitutive promoters known to those of skill in the art. "Tissue-specific" or "cell-type-specific" promoters, on the other hand, direct transcription in some tissues and cell types but are inactive in others. Exemplary tissue-specific promoters include the PSA promoter (Yu et al., 1999; Lee et al., 2000), the probasin promoter (Greenberg et al., 1994; Yu et al., 1999), and the MUC1 promoter (Kurihara et al., 2000) as discussed above, as well as other tissue-specific and cell-type specific promoters known to those of skill in the art.

When used in the context of a promoter, the term "linked" as used herein refers to a physical proximity of promoter elements such that they function together to direct transcription of an operably linked nucleotide sequence The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

In some embodiments, a promoter that is operably linked to a nucleotide sequence encoding a modulator of $cPLA_2$ is a promoter that is expressed in a cell that expresses $cPLA_2$. An exemplary promoter would be a $cPLA_2$ promoter itself, in some embodiments the promoter of the $cPLA_2$ gene from the same species in which the compositions and methods of the presently disclosed subject matter are to be deployed. For example, a human $cPLA_2$ gene product corresponds to GENBANK® Accession No. NM_024420. This sequence is present on human chromosome 1, and the genomic sequence that corresponds to the first nucleotide of NM_024420 is found on the plus strand GENBANK® Accession No. NT_004487.18 at position 37,288,386. One of ordinary skill in the art could thus, with routine experimentation, isolate a fragment of human chromosome 1 in the vicinity of position 37,288,386 of GENBANK®Accession No. NT_004487.18 that corresponds to the $cPLA_2$ promoter. Once isolated, the promoter fragment can be operably linked to a nucleotide sequence encoding a modulator of $cPLA_2$, thereby increasing the likelihood that the modulator of $cPLA_2$ and $cPLA_2$ would be co-expressed in a cell type of interest.

Alternatively or in addition, a promoter that includes one or more hypoxia response elements (HREs) can be operably linked to a nucleotide sequence encoding a modulator of $cPLA_2$ in order to express the modulator of $cPLA_2$ in hypoxic cells (e.g., in hypoxic regions of a tumor). A representative promoter that contains HRE sequences is the vascular endothelial growth factor (VEGF) promoter. Other HRE-containing promoters are disclosed in U.S. Pat. No. 7,067,649. Additionally, Semenza & Wang, 1992; Blanchard et al., 1992; Firth et al., 1995; and Ebert & Bunn, 1998 teach sequences of HREs, which can be concatamerized and included with one or more minimal promoter elements to produce a synthetic hypoxia-responsive promoter.

The presently disclosed subject matter includes in some embodiments vectors encoding $cPLA_2$ modulators (e.g., siRNAs targeted to $cPLA_2$, antibodies or fragments or derivatives thereof that bind to $cPLA_2$, etc.). The term "vector", as used herein refers to a DNA molecule having sequences that enable the transfer of those sequences to a compatible host cell. A vector also includes nucleotide sequences to permit ligation of nucleotide sequences within the vector, wherein such nucleotide sequences are also replicated in a compatible host cell. A vector can also mediate recombinant production of a therapeutic polypeptide, as described further herein below. In some embodiments, a vector is an adenovirus vector or an adeno-associated virus vector.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Exemplary, non-limiting methods are described by Silhavy et al., 1984; Ausubel et al., 1992; Ausubel, 1995; Glover & Hames, 1995; and Sambrook & Russell, 2001). Site-specific mutagenesis to create base pair changes, deletions, or small insertions is also known in the art as exemplified by publications (see e.g., Adelman et al., 1983; Sambrook & Russell, 2001).

In one aspect, the presently disclosed subject matter provides an siRNA molecule that has been synthesized outside of a target cell prior to introduction of the siRNA into the target cell. In this embodiment, the synthesis can be performed either mechanically (i.e., using an RNA synthesis machine) or using recombinant techniques.

Mechanical synthesis of nucleic acids greater than 100 nucleotides in length is difficult using automated methods, and the cost of such molecules tends to be prohibitive. As used herein, small nucleic acid motifs ("small" referring to nucleic acid motifs in some embodiments no more than 100 nucleotides in length, in some embodiments no more than 80 nucleotides in length, and in some embodiments no more than 50 nucleotides in length; e.g., individual siRNA oligonucleotide sequences or siRNA sequences synthesized in tandem) can be used for exogenous delivery. The simple structure of these molecules increases the ability of the nucleic acid to invade targeted regions of protein and/or RNA structure. Exemplary molecules of the presently disclosed subject matter are chemically synthesized, and others can similarly be synthesized.

Oligonucleotides (e.g., certain modified oligonucleotides or portions of oligonucleotides lacking ribonucleotides) are synthesized using protocols known in the art. See e.g., Caruthers et al., 1992; PCT International Publication No. WO 99/54459; Wincott et al., 1995; Wincott & Usman, 1997; Brennan et al., 1998; and U.S. Pat. No. 6,001,311, each of which is incorporated herein by reference. The synthesis of oligonucleotides makes use of common nucleic acid protecting and coupling groups, such as dimethoxytrityl at the 5'-end and phosphoramidites at the 3'-end. In a non-limiting example, small-scale syntheses can be conducted on a Applied Biosystems 3400 DNA Synthesizer (Applied Biosystems Inc., Foster City, Calif., United States of America) using a 0.2 μmol scale protocol with a 2.5 minute coupling step for 2'-O-methylated nucleotides and a 45 second coupling step for 2'-deoxy nucleotides or 2'-deoxy-2'-fluoro nucleotides. Alternatively, syntheses at the 0.2 μmol scale can be performed on a 96-well plate synthesizer. A 33-fold excess (60 μL of 0.11 M; 6.6 μmol) of 2'-O-methyl phosphoramidite and a 105-fold excess of S-ethyl tetrazole (60 μL of 0.25 M; 15 μmol) can be used in each coupling cycle of 2'-O-methyl residues relative to polymer-bound 5'-hydroxyl. A 22-fold excess (40 μL of 0.11 M; 4.4 μmol) of deoxy phosphoramidite and a 70-fold excess of S-ethyl tetrazole (40 μL of 0.25 M; 10 μmol) can be used in each coupling cycle of deoxy residues relative to polymer-bound 5'-hydroxyl. Average coupling yields on the Applied Biosystems 3400 DNA Synthesizer, determined by colorimetric quantitation of the trityl fractions, are typically 97.5-99%. Other oligonucleotide synthesis reagents for the Applied Biosystems 3400 DNA Synthesizer include the following: detritylation solution is 3% TCA in methylene chloride (Applied Biosystems, Inc.); capping is performed with 16% N-methyl imidazole in THF (Applied Biosystems, Inc.) and 10% acetic anhydride/10% 2,6-lutidine in THF (Applied Biosystems, Inc.); and oxidation solution is 16.9 mM $I_2$, 49 mM pyridine, 9% water in tetrahydrofuran (THF; PerSeptive Biosystmes, Hamburg, Germany). Synthesis Grade acetonitrile (Honeywell BURDICK & JACKSON™, Morritown, N.J., United States of America) is used directly from the reagent bottle. S-Ethyltetrazole solution (0.25 M in acetonitrile) is made up from the solid obtained from American International Chemical, Inc. Alternately, for the introduction of phosphorothioate internucleotide linkages, Beaucage reagent ($^3$H-1,2-benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:$H_2O$ (3:1:1), vortexed, and the supernatant is added to the first supernatant. The combined supernatants, containing the oligoribonucleotide, are dried to a white powder.

In some embodiments, the method of synthesis used for RNA including certain siRNA molecules of the presently disclosed subject matter follows the procedure as described in Usman et al., 1987; Scaringe et al., 1990; Wincott et al., 1995; Wincott & Usman, 1997; and makes use of common nucleic acid protecting and coupling groups, such as dimethoxytrityl at the 5'-end, and phosphoramidites at the 3'-end. In a non-limiting example, small-scale syntheses are conducted on an Applied Biosystems 3400 DNA Synthesizer using a 0.2 μmol scale protocol with a 7.5 minute coupling step for alkylsilyl protected nucleotides and a 2.5 minute coupling step for 2'-O-methylated nucleotides. Alternatively, syntheses at the 0.2 μmol scale can be done on a 96-well plate synthesizer. A 33-fold excess (60 μL of 0.11 M; 6.6 μmol) of 2'-O-methyl phosphoramidite and a 75-fold excess of S-ethyl tetrazole (60 μL of 0.25 M; 15 μmol) can be used in each coupling cycle of 2'-O-methyl residues relative to polymer-bound 5'-hydroxyl. A 66-fold excess (120 μL of 0.11 M;l 13.2 μmol) of alkylsilyl (ribo) protected phosphoramidite and a 150-fold excess of S-ethyl tetrazole (120 μL of 0.25 M; 30 μmol) can be used in each coupling cycle of ribo residues relative to polymer-bound 5'-hydroxyl. Average coupling yields on the Applied Biosystems 3400 DNA Synthesizer, determined by colorimetric quantitation of the trityl fractions, are typically 97.5-99%. Other oligonucleotide synthesis reagents for the Applied Biosystems 3400 DNA Synthesizer include the following: detritylation solution is 3% TCA in methylene chloride (Applied Biosystems, Inc.); capping is performed with 16% N-methyl imidazole in THF (Applied Biosystems, Inc.) and 10% acetic anhydride/10% 2,6-lutidine in THF (Applied Biosystems, Inc.); oxidation solution is 16.9 mM $I_2$, 49 mM pyridine, 9% water in tetrahydrofuran (THF; PerSeptive Biosystmes, Hamburg, Germany). Synthesis Grade acetonitrile (Honeywell BURDICK & JACKSON™, Morritown, N.J., United States of America) is used directly from the reagent bottle. S-Ethyltetrazole solution (0.25 M in acetonitrile) is made up from the solid obtained from American International Chemical, Inc. (Natick, Mass., United States of America). Alternately, for the introduction of phosphorothioate linkages, Beaucage reagent ($^3$H-1,2-Benzodithiol-3-one 1,1-dioxide 0.05 M in acetonitrile) is used.

Deprotection of the RNA can be performed, for example, using either a two-pot or one-pot protocol. For the two-pot protocol, the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O (3:1:1), vortexed, and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA.3HF to provide a 1.4 M HF concentration) and heated to 65° C. After 1.5 hours, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine:DMSO (1:1; 0.8 mL) at 65° C. for 15 minutes. The vial is brought to room temperature, TEA.3HF (0.1 mL) is added, and the vial is heated at 65° C. for 15 minutes. The sample is cooled at −20° C., and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% trifluoroacetic acid (TFA) for 13 min. The cartridge is then washed again with water, salt exchanged with 1 M NaCl, and washed with water again. The oligonucleotide is then eluted with 30% acetonitrile.

The average stepwise coupling yields are typically greater than 98% (Wincott et al., 1995). Those of ordinary skill in the art will recognize that the scale of synthesis can be adapted to be larger or smaller than the example described above including but not limited to 96-well format: all that is important is the ratio of chemicals used in the reaction.

Alternatively, the nucleic acid molecules of the presently disclosed subject matter can be synthesized separately and joined together post-synthetically, for example, by ligation (PCT International Publication No. WO 93/23569; Shabarova et al., 1991; Bellon et al., 1997), or by hybridization following synthesis and/or deprotection.

The siRNA molecules of the presently disclosed subject matter can also be synthesized via a tandem synthesis methodology as described in Example 2 herein, wherein both siRNA strands are synthesized as a single contiguous oligonucleotide fragment or a strand separated by a linker which, in some embodiments, is subsequently cleaved to provide separate siRNA fragments or strands that hybridize and permit purification of the siRNA duplex. The linker can be a polynucleotide linker or a non-nucleotide linker. The tandem synthesis of siRNA as described herein can be readily adapted to both multiwell and multiplate synthesis platforms such as 96 well or similarly larger multi-well platforms. The tandem synthesis of siRNA as described herein can also be readily adapted to large-scale synthesis platforms employing batch reactors, synthesis columns and the like.

A siRNA molecule can also be assembled from two distinct nucleic acid strands or fragments wherein one fragment includes the sense region and the second fragment includes the antisense region of the RNA molecule.

In some embodiments, recombinant techniques can be used to synthesize an siRNA, which can thereafter be purified from the source and transferred to a target cell. There are many techniques that are known in the art for the synthesis RNA molecules in recombinant cells, and any such technique can be used in the practice of the presently disclosed subject matter. One such general strategy for synthesizing an RNA molecule includes cloning a DNA sequence downstream of an RNA polymerase promoter and introducing the recombinant molecule into a cell in which the promoter is competent to direct transcription of the cloned sequence. This can be accomplished using a plasmid constructed for this purpose.

Alternatively, the RNA can be synthesized in the target cell using an expression vector, for example an expression plasmid. Such plasmids include, but are not limited to the PSILENCER™ series of plasmids (Ambion, Inc., Austin, Tex., United States of America), and the plasmid disclosed by Miyagishi & Taira, 2002.

The pSILENCER™ series of plasmids contain a cloning site downstream of a mammalian RNA polymerase III promoter. A nucleic acid encoding a hairpin with a 19 base pair duplex region can be cloned into the cloning site of one of these plasmids. When the recombinant plasmid is introduced into a mammalian cell, the RNA polymerase III promoter directs transcription of the hairpin RNA molecule, which thereafter forms the hairpin characterized by the 19 base pair duplex. This hairpin is apparently recognized by the Dicer nuclease, which cleaves the hairpin to form a functional siRNA.

Miyagishi & Taira, 2002 discloses another strategy for producing siRNA molecules. This reference discloses a plasmid that has two RNA polymerase III promoters. To produce an siRNA, the same 19 base pair nucleic acid molecule is cloned downstream of each promoter, but in opposite orientations. Thus, the plasmid produces distinct sense and antisense RNA strands, which then undergo intermolecular hybridization to produce an siRNA. In this case, the promoter is the U6 promoter. An RNA transcribed from a U6 promoter has a stretch of about four uridines at its 3' end. Thus, the use of this plasmid results in the production of two RNA strands, each of which contains a 19 base region that is capable of hybridizing to a 19 base region in the other, with a short 3' overhang.

Chemically synthesizing nucleic acid molecules incorporating various modifications (e.g. to base, sugar, and/or phosphate moieties) can reduce the degradation of the nucleic acid molecules by ribonucleases present in biological fluids, and can thus can increase the potency of therapeutic nucleic acid molecules (see e.g., PCT International Publication Nos. WO 92/07065, WO 93/15187, and WO 91/03162; U.S. Pat. Nos. 5,334,711 and 6,300,074; Perrault et al., 1990; Pieken et al., 1991; Usman & Cedergren, 1992; and Burgin et al., 1996; all of which are incorporated by reference herein). Each of the above references describe various chemical modifications that can be made to the base, phosphate, and/or sugar moieties of the nucleic acid molecules described herein. Modifications can be employed to enhance the efficacy of the disclosed nucleic acid molecules in cells.

There are several examples in the art describing sugar, base, and phosphate modifications that can be introduced into nucleic acid molecules with significant enhancement in their nuclease stability and efficacy. For example, oligonucleotides can be modified to enhance their stability and/or enhance biological activity by modification with nuclease resistant groups, for example, 2'-amino, 2'-C-allyl, 2'-flouro, 2'-O-methyl, 2'-O-allyl, 2'-H, nucleotide base modifications (reviewed in Usman & Cedergren, 1992; Usman et al., 1994; Burgin et al., 1996). Sugar modification of nucleic acid molecules have been extensively described in the art (see PCT International Publication Nos. WO 92/07065, WO 93/15187, WO 98/13526, and WO 97/26270; U.S. Pat. Nos. 5,334,711; 5,716,824; and 5,627,053; Perrault et al., 1990; Pieken et al., 1991; Usman & Cedergren, 1992; Beigelman et al., 1995; Karpeisky et al., 1998; Earnshaw & Gait, 1998; Verma & Eckstein, 1998; Burlina et al., 1997; all of which are incorporated by reference herein). Such publications describe general methods and strategies to determine the location of incorporation of sugar, base, and/or phosphate modifications and the like into nucleic acid molecules without modulating catalysis. In view of such teachings, similar modifications can be used as described herein to modify the siRNA nucleic acid molecules of the presently disclosed subject matter so long as the ability of the siRNAs to promote RNAi in a cell is not significantly inhibited.

While chemical modification of oligonucleotide internucleotide linkages with phosphorothioate and/or 5'-methylphosphonate linkages improves stability, excessive modifications can cause toxicity or decreased activity. Therefore, when designing nucleic acid molecules, the number of these internucleotide linkages should be minimized. Reducing the concentration of these linkages should lower toxicity, resulting in increased efficacy and higher specificity of these molecules.

The term “universal base” as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see, for example, Loakes, 2001).

Small interfering RNA (siRNA) molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA (Wincott et al., 1995; Caruthers et al., 1992) have expanded the ability to modify nucleic acid molecules by introducing nucleotide modifications to enhance their nuclease stability, as described above. siRNA constructs can be purified by gel electrophoresis using general methods or can be purified by high pressure liquid chromatography (HPLC; see Wincott et al., 1995) and re-suspended in water.

In some embodiments, the presently disclosed subject matter features conjugates and/or complexes of siRNA molecules. Such conjugates and/or complexes can be used to facilitate delivery of siRNA molecules into a biological system, such as a cell. The conjugates and complexes provided by the presently disclosed subject matter can impart therapeutic activity by transferring therapeutic compounds across cellular membranes, altering the pharmacokinetics of, and/or modulating the localization of nucleic acid molecules of the presently disclosed subject matter. The presently disclosed subject matter encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers, and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the presently disclosed subject matter into a number of cell types originating from different tissues, in the presence or absence of serum (see U.S. Pat. No. 5,854,038). Conjugates of the molecules described herein can be attached to biologically active molecules via linkers that are biodegradable, such as biodegradable nucleic acid linker molecules.

The term “biodegradable linker” as used herein, refers to a nucleic acid or non-nucleic acid linker molecule that is designed as a biodegradable linker to connect one molecule to another molecule, for example, a biologically active molecule to a siRNA molecule of the presently disclosed subject matter or the sense and antisense strands of a siRNA molecule of the presently disclosed subject matter. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active siRNA molecules either alone or in combination with other molecules provided by the presently disclosed subject matter include therapeutically active molecules such as antibodies, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siRNA, dsRNA, allozymes, aptamers, decoys, and analogs thereof. Biologically active molecules of the presently disclosed subject matter also include molecules capable of modulating the pharmacokinetics and/or pharmacodynamics of other biologically active molecules, for example, lipids and polymers such as polyamines, polyamides, polyethylene glycol, and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

Nucleic acid molecules (e.g., siRNA molecules) delivered exogenously are intended to be stable within cells until the level of the target RNA has been reduced sufficiently. The nucleic acid molecules are resistant to nucleases in order to function as effective intracellular therapeutic agents. Improvements in the chemical synthesis of nucleic acid molecules described in the presently disclosed subject matter and in the art have expanded the ability to modify nucleic acid molecules by introducing nucleotide modifications to enhance their nuclease stability as described above.

In some embodiments, siRNA molecules having chemical modifications that maintain or enhance enzymatic activity of proteins involved in RNAi are provided. Such nucleic acids are also generally more resistant to nucleases than unmodified nucleic acids. Thus, in vitro and/or in vivo activity should not be significantly lowered.

Use of the nucleic acid-based molecules of the presently disclosed subject matter will lead to better treatment of the disease progression by affording the possibility of combination therapies (e.g., multiple siRNA molecules targeted to different genes; nucleic acid molecules coupled with known small molecule modulators; or intermittent treatment with combinations of molecules, including different motifs and/or other chemical or biological molecules). The treatment of subjects with siRNA molecules can also include combinations of different types of nucleic acid molecules, such as enzymatic nucleic acid molecules (ribozymes), allozymes, antisense, 2,5-A oligoadenylate, decoys, aptamers etc.

In another aspect a siRNA molecule of the presently disclosed subject matter comprises one or more 5' and/or 3'-cap structures, for example on only the sense siRNA strand, antisense siRNA strand, or both siRNA strands.

As used herein, the phrase "cap structure" is meant to refer to chemical modifications that have been incorporated at either terminus of the oligonucleotide (see e.g., U.S. Pat. No. 5,998,203, incorporated by reference herein). These terminal modifications protect the nucleic acid molecule from exonuclease degradation, and can help in delivery and/or localization within a cell. The cap can be present at the 5'-terminus (5'-cap) or at the 3'-terminal (3'-cap), or can be present on both termini. In non-limiting examples: the 5'-cap is selected from the group comprising inverted abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In some embodiments, the 3'-cap is selected from a group comprising 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (see generally Beaucage & Iyer, 1993; incorporated by reference herein).

As used herein, the term "non-nucleotide" refers to any group or compound which can be incorporated into a nucleic acid chain in the place of one or more nucleotide units, including either sugar and/or phosphate substitutions, and allows the remaining bases to exhibit their enzymatic activity. The group or compound is typically abasic, in that it does not typically contain a commonly recognized nucleotide base, such as adenine (A), guanine (G), cytosine (C), thymine (T), or uracil (U), and therefore lacks a base at the 1'-position.

As used herein, the term "alkyl" group refers to a saturated aliphatic hydrocarbon, including straight-chain, branched-chain, and cyclic alkyl groups. In some embodiments, the alkyl group has 1 to 12 carbons. In some embodiments, it is a lower alkyl of from 1 to 7 carbons, and in some embodiments it is a lower alkyl of from 1 to 4 carbons. The alkyl group can be substituted or unsubstituted. When substituted the substituted group(s) is in alternative embodiments, hydroxyl, cyano, alkoxy, =O, =S, $NO_2$ or $N(CH_3)_2$, amino, or SH.

The term "alkyl" also includes alkenyl groups that are unsaturated hydrocarbon groups containing at least one carbon-carbon double bond, including straight-chain, branched-chain, and cyclic groups. In some embodiments, the alkenyl group has 1 to 12 carbons. In some embodiments, it is a lower alkenyl of from 1 to 7 carbons, and in some embodiments it is a lower alkenyl of from 1 to 4 carbons. The alkenyl group can be substituted or unsubstituted. When substituted the substituted group(s) is in alternative embodiments, hydroxyl, cyano, alkoxy, =O, =S, $NO_2$, halogen, $N(CH_3)_2$, amino, or SH.

The term "alkyl" also includes alkynyl groups that have an unsaturated hydrocarbon group containing at least one carbon-carbon triple bond, including straight-chain, branched-chain, and cyclic groups. In some embodiments, the alkynyl group has 1 to 12 carbons. In some embodiments, it is a lower alkynyl of from 1 to 7 carbons, and in some embodiments it is a lower alkynyl of from 1 to 4 carbons. The alkynyl group can be substituted or unsubstituted. When substituted the substituted group(s) is in alternative embodiments, hydroxyl, cyano, alkoxy, =O, =S, $NO_2$ or $N(CH_3)_2$, amino or SH.

Such alkyl groups can also include aryl, alkylaryl, carbocyclic aryl, heterocyclic aryl, amide, and ester groups. An "aryl" group refers to an aromatic group that has at least one ring having a conjugated pi electron system and includes carbocyclic aryl, heterocyclic aryl, and biaryl groups, all of which can be optionally substituted. Exemplary substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to a —C(O)—NH—R, where R is either alkyl, aryl, alkylaryl, or hydrogen. An "ester" refers to an C(O)—OR', where R is either alkyl, aryl, alkylaryl, or hydrogen.

The term "nucleotide" is used herein as recognized in the art to include natural bases (standard), and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides, and other; see e.g., Usman et al., 1996; PCT International Publication Nos. WO 92/07065 and WO 93/15187, all incorporated by reference herein). There are several examples of modified nucleic acid bases known in the art as summarized by Limbach et al., 1994. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine), 6-azapyrimidines and 6-alkylpyrimidines (e.g. 6-methyluridine), propyne, and others (Burgin et al., 1996; Uhlman & Peyman, 1990). By "modified bases" in this aspect is meant nucleotide bases other than adenine, guanine, cytosine, and uracil at 1' position or their equivalents.

In some embodiments, the presently disclosed subject matter features modified siRNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker & Leumann, 1995 and De Mesmaeker et al., 1994.

As used herein, the term "abasic" refers to sugar moieties lacking a commonly recognized nucleoside base (e.g., A, C, G, T, or U) or having other chemical groups in place of the commonly recognized base at the 1' position. See e.g., U.S. Pat. No. 5,998,203.

As used herein, the phrase "unmodified nucleoside" refers to one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate.

In connection with 2'-modified nucleotides as described for the presently disclosed subject matter, by "amino" is meant 2'-$NH_2$ or 2'-O—$NH_2$, which can be modified or unmodified. Such modified groups are described, for example, in U.S. Pat. Nos. 5,672,695 and 6,248,878, which are both incorporated by reference in their entireties.

Various modifications to nucleic acid siRNA structure can be made to enhance the utility of these molecules. Such modifications will enhance shelf-life, half-life in vitro, stability, and/or ease of introduction of such oligonucleotides to the target site (for example, to enhance penetration of cellular membranes, and confer the ability to recognize and bind to targeted cells).

Exemplary siRNAs targeted to $cPLA_2$ gene products have been disclosed in Li et al., 2005 and Cowan et al., 2006).

III.E. Sustained Bioavailability

The term "sustained bioavailability" is used herein to describe a composition comprising a $cPLA_2$ antagonist and a carrier, whereby the bioavailability of a $cPLA_2$ antagonist at a tumor site is sufficient to achieve radiosensitization of a tumor. The term "sustained bioavailability" also refers to a bioavailability sufficient to inhibit blood vessel growth within the tumor. The term "sustained bioavailability" encompasses factors including but not limited to sustained release of a $cPLA_2$ antagonist from a carrier, metabolic stability of a $cPLA_2$ antagonist, systemic transport of a composition comprising a $cPLA_2$ antagonist, and effective dose of a $cPLA_2$ antagonist.

As disclosed herein, an immediate response of tumor blood vessels to radiation is a decrease in tumor blood flow. This response can diminish administration of an anti-tumor composition (e.g., a $cPLA_2$ antagonist). Recognizing this response, the disclosure of the presently claimed subject matter provides that sustained bioavailability of a $cPLA_2$ antagonist, for example by selection of a carrier and administration regimen that achieve sustained bioavailability, can improve anti-tumor activity. One example of carrier comprises a gene therapy vector encoding a $cPLA_2$ antagonist (e.g., a neutralizing antibody or fragment or derivative thereof or an siRNA targeted to a $cPLA_2$ gene product).

A method comprising a carrier or administration approach for sustained bioavailability can also improve therapies directed toward modulation of other components of the $cPLA_2$ signaling pathway. Thus, the presently claimed subject matter further provides an improved method for inhibiting tumor growth, the method comprising administration of a gene therapy vector encoding an inhibitor of $cPLA_2$ signaling, whereby bioavailability of the inhibitor at a tumor is sustained, and whereby tumor growth delay is improved.

IV. Therapeutic Compositions

In accordance with the methods of the presently claimed subject matter, a composition that is administered to increase the radiosensitivity of a target tissue in a subject comprises: (a) a $cPLA_2$ antagonist; and (b) a pharmaceutically acceptable carrier. Any suitable carrier that facilitates drug preparation and/or administration can be used.

IV.A. Carriers

The carrier can be a viral vector or a non-viral vector. Suitable viral vectors include adenoviruses, adeno-associated viruses (AAVs), retroviruses, pseudotyped retroviruses, herpes viruses, vaccinia viruses, Semiliki forest virus, and baculoviruses. In some embodiments of the presently claimed subject matter, the carrier comprises an adenoviral gene therapy construct that encodes a $cPLA_2$ antagonist.

Suitable non-viral vectors that can be used to deliver a $cPLA_2$ antagonist include but are not limited to a plasmid, a nanosphere (Manome et al., 1994; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651, 991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997) and U.S. Pat. Nos. 4,551,482, 5,714,166, 5,510,103, 5,490,840, and 5,855,900), and a polysome (U.S. Pat. No. 5,922,545).

Where appropriate, two or more types of carriers can be used together. For example, a plasmid vector can be used in conjunction with liposomes. Currently, some embodiments of the presently claimed subject matter envisions the use of an adenovirus.

In some embodiments, a composition of the presently claimed subject matter comprises a $cPLA_2$ antagonist and a carrier to effect sustained bioavailability of the $cPLA_2$ antagonist following administration to a tumor-bearing subject. The term "sustained bioavailability" is used herein to refer to a bioavailability of a $cPLA_2$ antagonist sufficient to achieve radiosensitization of a tumor. The term "sustained bioavailability" also refers to a bioavailability of a $cPLA_2$ antagonist sufficient to inhibit blood vessel growth within a tumor. The term "sustained bioavailability" encompasses factors including but not limited to prolonged release of a $cPLA_2$ antagonist from a carrier, systemic transport of a composition comprising a $cPLA_2$ antagonist, and effective dose of a $cPLA_2$ antagonist.

Representative compositions for sustained bioavailability of a $cPLA_2$ antagonist can include but are not limited to polymer matrices, including swelling and biodegradable polymer matrices, (U.S. Pat. Nos. 6,335,035; 6,312,713; 6,296,842; 6,287,587; 6,267,981; 6,262,127; and 6,221,958), polymer-coated microparticles (U.S. Pat. Nos. 6,120,787 and 6,090,925) a polyol:oil suspension (U.S. Pat. No. 6,245,740), porous particles (U.S. Pat. No. 6,238,705), latex/wax coated granules (U.S. Pat. No. 6,238,704), chitosan microcapsules, and microsphere emulsions (U.S. Pat. No. 6,190,700).

An exemplary embodiment for sustained bioavailability of a $cPLA_2$ antagonist comprises a gene therapy construct comprising a gene therapy vector, for example a gene therapy vector described herein below.

Viral Gene Therapy Vectors. In some embodiments, viral vectors of the presently claimed subject matter are disabled; e.g. replication-deficient. That is, they lack one or more functional genes required for their replication, which prevents their uncontrolled replication in vivo and avoids undesirable side effects of viral infection. In some embodiments, all of the viral genome is removed except for the minimum genomic elements required to package the viral genome incorporating the therapeutic gene into the viral coat or capsid. For example, it is desirable to delete all the viral genome except: (a) the Long Terminal Repeats (LTRs) or Inverted Terminal Repeats (ITRs); and (b) a packaging signal. In the case of adenoviruses, deletions are typically made in the E1 region and optionally in one or more of the E2, E3, and/or E4 regions. Other viral vectors can be similarly deleted of genes required for replication. Deletion of sequences can be achieved by recombinant approaches, for example, involving digestion with appropriate restriction enzymes, followed by religation. Replication-competent self-limiting or self-destructing viral vectors can also be used.

Nucleic acid constructs of the presently claimed subject matter can be incorporated into viral genomes by any suitable approach known in the art. Typically, such incorporation is performed by ligating the construct into an appropriate restriction site in the genome of the virus. Viral genomes can then be packaged into viral coats or capsids using any suitable procedure. In particular, any suitable packaging cell line can be used to generate viral vectors of the presently claimed subject matter. These packaging lines complement the replication-deficient viral genomes of the presently claimed subject matter, as they include, for example by incorporation into their genomes, the genes that have been deleted from the replication-deficient genome. Thus, the use of packaging lines allows viral vectors of the presently claimed subject matter to be generated in culture.

Suitable packaging lines for retroviruses include derivatives of PA317 cells, ψ-2 cells, CRE cells, CRIP cells, E-86-GP cells, and 293GP cells. Line 293 cells can be used with adenoviruses and adeno-associated viruses.

Plasmid Gene Therapy Vectors. Certain of the $cPLA_2$ antagonists of the presently disclosed subject matter can also be encoded by a plasmid. Advantages of a plasmid carrier include low toxicity and easy large-scale production. A polymer-coated plasmid can be delivered using electroporation as described by Fewell et al., 2001. Alternatively, a plasmid can be combined with an additional carrier, for example a cationic polyamine, a dendrimer, or a lipid, that facilitates delivery (Baher et al., 1999; Maruyama-Tabata et al., 2000; Tam et al., 2000).

Liposomes. A $cPLA_2$ antagonist of the presently claimed subject matter can also be delivered using a liposome. For example, a nucleic acid molecule encoding a $cPLA_2$ antagonist can be encapsulated in a liposome. Liposomes can be prepared by any of a variety of techniques that are known in the art. See e.g., Dracopoli et al., 1997; Lasic & Martin, 1995; Janoff, 1999; Gregoriadis, 1993; Betageri et al., 1993; and U.S. Pat. Nos. 4,235,871; 4,551,482; 6,197,333; and 6,132, 766. Temperature-sensitive liposomes can also be used, for example THERMOSOMES™, as disclosed in U.S. Pat. No. 6,200,598. Entrapment of a $cPLA_2$ antagonist within liposomes of the presently claimed subject matter can be carried out using any conventional method in the art. In preparing liposome compositions, stabilizers such as antioxidants and other additives can be used.

Other lipid carriers can also be used in accordance with the claimed presently claimed subject matter, such as lipid microparticles, micelles, lipid suspensions, and lipid emulsions. See e.g., Labat-Moleur et al., 1996; and U.S. Pat. Nos. 5,011, 634; 6,056,938; 6,217,886; 5,948,767; and 6,210,707.

IV.B. Targeting Ligands

As desired, a composition of the presently claimed subject matter can include one or more ligands having affinity for a specific cellular marker to thereby enhance delivery of a $cPLA_2$ antagonist to a tumor in vivo. Ligands include antibodies, cell surface markers, peptides, and the like, which act to home the $cPLA_2$ antagonist to a tumor, including the tumor vasculature.

The terms "targeting" and "homing", as used herein to describe the in vivo activity of a ligand following administration to a subject, each refer to the preferential movement and/or accumulation of a ligand in a target tissue (e.g., a tumor) as compared with a control tissue.

The term "control tissue" as used herein refers to a site suspected to substantially lack binding and/or accumulation of an administered ligand. For example, in some embodiments, a non-cancerous tissue can be a control tissue.

The terms "selective targeting" of "selective homing" as used herein each refer to a preferential localization of a ligand that results in some embodiments in an amount of ligand in a target tissue that is about 2-fold greater than an amount of ligand in a control tissue, in another embodiment in an amount that is about 5-fold or greater, and in still another embodiment in an amount that is about 10-fold or greater. The terms "selective targeting" and "selective homing" also refer to binding or accumulation of a ligand in a target tissue concomitant with an absence of targeting to a control tissue, or the absence of targeting to all control tissues.

The terms "targeting ligand" and "targeting molecule" as used herein each refer to a ligand that displays targeting activity. In some embodiments, a targeting ligand displays selective targeting. Representative targeting ligands include peptides and antibodies.

The term "peptide" encompasses any of a variety of forms of peptide derivatives that include amides, conjugates with proteins, cyclized peptides, polymerized peptides, conservatively substituted variants, analogs, fragments, peptoids, chemically modified peptides, and peptide mimetics. Representative peptide ligands that show tumor-binding activity include, for example, those described in U.S. Pat. Nos. 6,180,084 and 6,296,832.

The term "antibody" indicates an immunoglobulin protein, or functional portion thereof, including a polyclonal antibody, a monoclonal antibody, a chimeric antibody, a hybrid antibody, a single chain antibody (e.g., a single chain antibody represented in a phage library), a mutagenized antibody, a humanized antibody, and antibody fragments that comprise an antigen binding site (e.g., Fab and Fv antibody fragments). Representative antibody ligands that can be used in accordance with the methods of the presently claimed subject matter include antibodies that bind the tumor-specific antigens Her2/neu (v-erb-b2 avian erythroblastic leukemia viral oncogene homologue-2; Kirpotin et al., 1997; Becerril et al., 1999) and antibodies that bind to CEA (carcinoembryonic antigen; Ito et al., 1991). See also U.S. Pat. Nos. 5,111,867; 5,632,991; 5,849,877; 5,948,647; 6,054,561 and PCT International Publication No. WO 98/10795.

In an effort to identify ligands that are capable of targeting to multiple tumor types, targeting ligands have been developed that bind to target molecules present on tumor vasculature (Baillie et al., 1995; Pasqualini & Ruoslahti, 1996; Arap et al., 1998; Burg et al., 1999; Ellerby et al., 1999).

A targeting ligand can also comprise a ligand that specifically binds to a radiation induced target molecule. Ionizing radiation induces proteins in tumor vascular endothelium through transcriptional induction and/or posttranslational modification of cell adhesion molecules such as integrins (Hallahan et al., 1995; Hallahan et al., 1996; Hallahan et al., 1998; Hallahan &Virudachalam, 1999). For example, radiation induces activation of the integrin $\alpha_{2b}\beta_3$, also called the fibrinogen receptor, on platelets. The induced molecules can serve as binding sites for targeting ligands. A representative peptide ligand that binds to irradiated tumors comprises Biapcitide (ACUTECT® available from Diatide, Inc. of Londonberry, N.H., United States of America), which specifically binds to glycoprotein (GP) IIb/IIIa receptors on activated platelets (Hawiger et al., 1989; Hawiger & Timmons, 1992; Hallahan et al., 2001).

Antibodies, peptides, or other ligands can be coupled to drugs (e.g., a $cPLA_2$ antagonist) or drug carriers using methods known in the art, including but not limited to carbodiimide conjugation, esterification, sodium periodate oxidation followed by reductive alkylation, and glutaraldehyde crosslinking. See e.g., Bauminger & Wilchek, 1980; Dracopoli et al., 1997; Goldman et al., 1997; Kirpotin et al., 1997; Neri et al., 1997; Park et al., 1997; Pasqualini et al., 1997; U.S. Pat. No. 6,071,890; and European Patent No. 0 439 095. Alternatively, pseudotyping of a retrovirus can be used to target a virus towards a particular cell (Marin et al., 1997).

A composition of the presently claimed subject matter comprises in some embodiments a $cPLA_2$ antagonist and a pharmaceutically acceptable carrier. Suitable formulations include aqueous and non-aqueous sterile injection solutions, which can contain anti-oxidants, buffers, bacteriostats, bactericidal antibiotics, and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Examples of useful ingredients are sodium dodecyl sulfate (SDS), for example in the range of 0.1 to 10 mg/ml, in another example about 2.0 mg/ml; and/or mannitol or another sugar, for example in the range of 10 to 100 mg/ml, in another example about 30 mg/ml; phosphate buffered saline (PBS), and any other formulation agents conventional in the art.

The therapeutic regimens and pharmaceutical compositions of the presently claimed subject matter can be used with additional adjuvants or biological response modifiers including, but not limited to, the cytokines interferon alpha (IFN-$\alpha$), interferon gamma (IFN-$\gamma$), interleukin 2 (IL2), interleukin 4 (IL4), interleukin 6 (IL6), tumor necrosis factor (TNF), or other cytokine affecting immune cells.

V. Therapeutic Methods

The disclosed $cPLA_2$ antagonists are useful as radiosensitizing agents. Thus, in some embodiments the presently claimed subject matter provides a method for suppressing tumor growth comprising: (a) administering a $cPLA_2$ antagonist to a subject bearing a tumor to increase the radiosensitivity of the tumor; and (b) treating the tumor with ionizing radiation, whereby tumor growth is delayed. Also provided is a method for inhibiting tumor blood vessel growth via administration of a $cPLA_2$ antagonist.

While applicants do not intend to be bound by any particular theory of operation, a $cPLA_2$ antagonist is believed to effectively suppress tumor growth by blocking reperfusion of an irradiated tumor. Specifically, a $cPLA_2$ antagonist can block processes that require $cPLA_2$, including the mediation of growth factor signals that result in endothelial cell infiltration and budding of tumor blood vessels. Similarly, a $cPLA_2$ antagonist is believed to effectively inhibit the growth of tumor blood vessels by blocking the ability of growth factors to mediate blood vessel growth.

V.A. Administration of a $cPLA_2$ Antagonist

Suitable methods for administration of a composition of the presently claimed subject matter include but are not limited to intravascular, subcutaneous, intramuscular, intraperitoneal, or intratumoral administration. For delivery of compositions to pulmonary pathways, compositions can be administered as an aerosol or coarse spray. A delivery method is selected based on considerations such as the type of $cPLA_2$ antagonist, the type of carrier or vector, toxicity of the $cPLA_2$ antagonist, therapeutic efficacy of the $cPLA_2$ antagonist, and the condition of the tumor to be treated. In some embodiments of the presently claimed subject matter, intravascular administration is employed.

In some embodiments, an effective amount of a composition of the presently claimed subject matter is administered to a subject. An "effective amount" is an amount of a composition comprising a $cPLA_2$ antagonist sufficient to produce a measurable anti-tumor response (e.g., increase of radiation sensitivity, an anti-angiogenic response, a cytotoxic response, and/or tumor regression). Actual dosage levels of active ingredients in a therapeutic composition of the presently claimed subject matter can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. Determination and adjustment of a therapeutically effective dose, as well as evaluation of when and how to make such adjustments, are known to those of ordinary skill in the art of medicine.

In some embodiments of the presently claimed subject matter, a minimally therapeutic dose of a $cPLA_2$ antagonist is administered. The term "minimally therapeutic dose" refers to the smallest dose, or smallest range of doses, determined to be a therapeutically effective amount as defined herein above.

V.B. Radiation Treatment

For treatment of a radiosensitized target tissue, the target tissue is irradiated concurrent with, or subsequent to, administration of a composition comprising a $cPLA_2$ antagonist. In accordance with the methods of the presently claimed subject matter, the target tissue can be irradiated daily for 2 weeks to 7 weeks (for a total of 10 treatments to 35 treatments). Alternatively, target tissues can be irradiated with brachytherapy utilizing high dose rate or low dose rate brachytherapy internal emitters.

Subtherapeutic or therapeutic doses of radiation can be used for treatment of a radiosensitized target tissue as disclosed herein. In some embodiments, a subtherapeutic or minimally therapeutic dose (when administered alone) of ionizing radiation is used. For example, the dose of radiation can comprise at least about 2 Gy ionizing radiation, in another example about 2 Gy to about 6 Gy ionizing radiation, and in yet another example about 2 Gy to about 3 Gy ionizing radiation. When radiosurgery is used, representative doses of radiation include about 10 Gy to about 20 Gy administered as a single dose during radiosurgery or about 7 Gy administered daily for 3 days (about 21 Gy total). When high dose rate brachytherapy is used, a representative radiation dose comprises about 7 Gy daily for 3 days (about 21 Gy total). For low dose rate brachytherapy, radiation doses typically comprise about 12 Gy administered twice over the course of 1 month. $^{125}I$ seeds can be implanted into a target tissue and can be used to deliver very high doses of about 110 Gy to about 140 Gy in a single administration.

Radiation can be localized to a target tissue using conformal irradiation, brachytherapy, stereotactic irradiation, or intensity modulated radiation therapy (IMRT). The threshold dose for treatment can thereby be exceeded in the target tissue but avoided in surrounding normal tissues. For treatment of a subject having two or more target tissues, local irradiation enables differential drug administration and/or radiotherapy at each of the two or more target tissues. Alternatively, whole body irradiation can be used, as permitted by the low doses of radiation required following radiosensitization of the target tissue.

Radiation can also comprise administration of internal emitters, for example $^{131}I$ for treatment of thyroid cancer, NETASTRON™ and QUADRAGEN® pharmaceutical compositions (Cytogen Corp. of Princeton, N.J., United States of America) for treatment of bone metastases, and $^{32}P$ for treatment of ovarian cancer. Other internal emitters include $^{125}I$, iridium, and cesium. Internal emitters can be encapsulated for administration or can be loaded into a brachytherapy device. Radiotherapy methods suitable for use in the practice of the presently disclosed subject matter can be found in Leibel & Phillips, 1998, among other sources.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Phosphorylation of ERK1/2 in Response to Irradiation

Figure 1B:
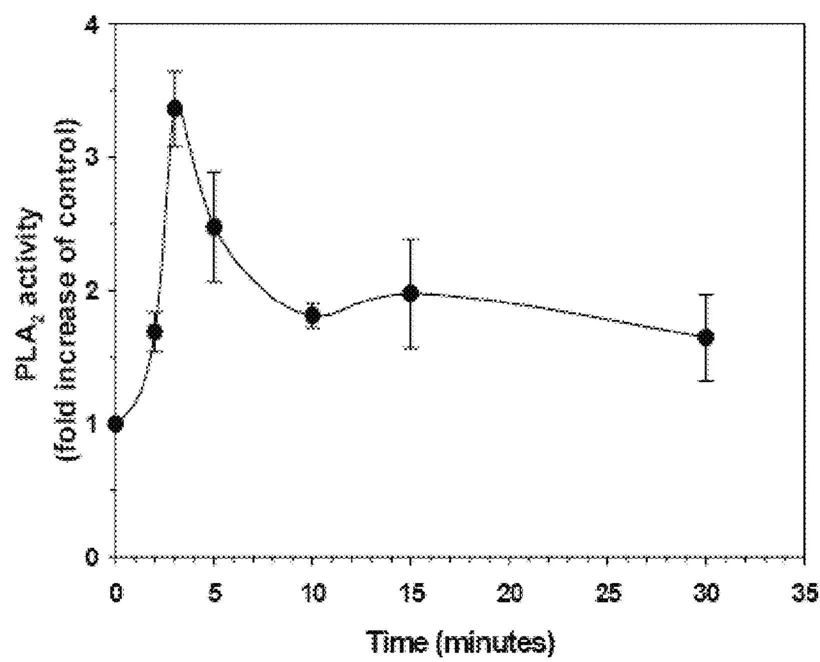

To determine whether $cPLA_2$ and down-stream signaling events are involved in inherent resistance of vascular endothelium to ionizing radiation, primary cultured human umbilical vascular endothelial cells (HUVEC) were studied. It was previously shown that low dose irradiation activates Akt by increasing phosphorylation at Ser473 (human Akt; e.g., GENBANK® Accession No. NP_005154) within minutes of exposure to low dose ionizing radiation (Tan & Hallahan 2003; Tan et al., 2006). Disclosed herein are the results of studying the extracellular signal regulated kinase 1/2 (ERK1/2), a member of the pro-survival MAP kinase signaling pathway, which is phosphorylated at Thr202/Tyr204 (human amino acid positions as shown in GENBANK® Accession Nos. P27361 (ERK1) and P28482 (ERK2), respectively) in response to treatment with 3 Gy (see FIG. 1A). This phosphorylation was transient. It was first observed within 2 minutes of irradiation, reached a maximum at 5 minutes, and returned to the basal level at 10 minutes (see FIG. 1A). Total cellular phospholipase A2 was activated during a similar time course (see FIG. 1B). The maximal activation of PLA2 occurred 3 minutes after irradiation, which precedes the peak phosphorylation of ERK1/2 (5 minutes) and Akt (10 minutes; see FIGS. 1A and 1B).

Example 2

Treatment of HUVEC with Specific PLA2 Inhibitors

Figure 1C:
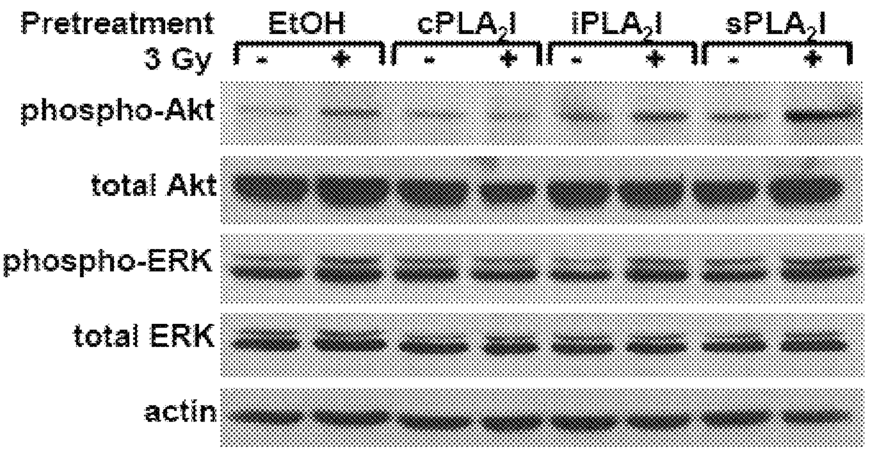
Figure 1D:
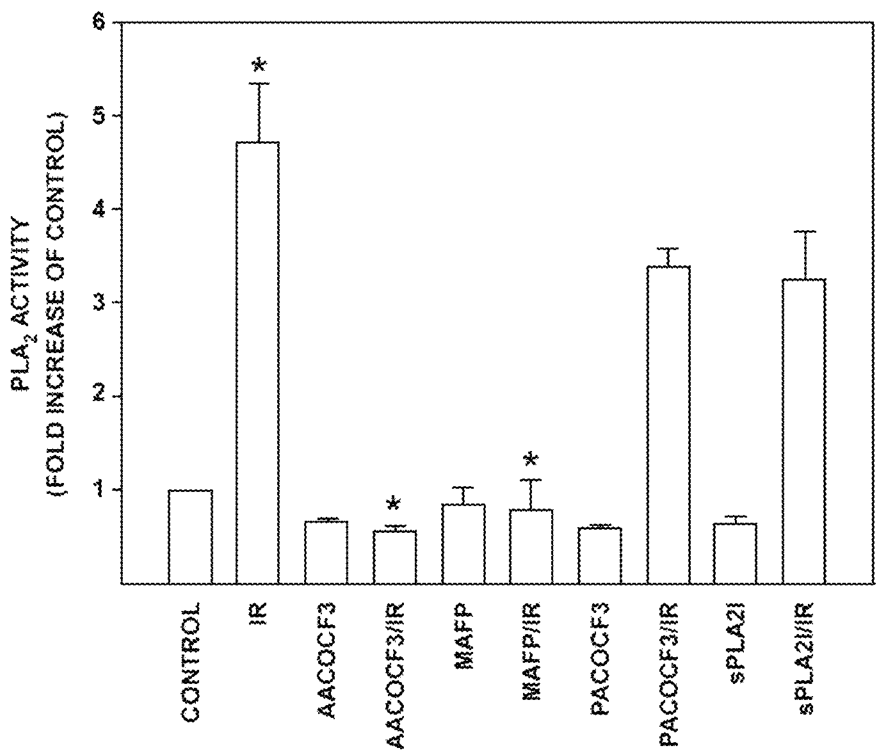

To determine which subtype of the PLA2 family is activated by 3 Gy, HUVEC were treated with specific inhibitors of $cPLA_2$, sPLA2, or iPLA2 for 30 minutes prior to exposure to 3 Gy. Cells were harvested 3 minutes after the beginning of irradiation. In HUVEC pretreated with inhibitors of $cPLA_2$ (1 μM $AACOCF_3$ or 1 μM MAFP), radiation-induced activation of PLA2 was completely abrogated (see FIG. 1C). In comparison, pretreatment of cells with inhibitors of sPLA2 (100 nM sPLA2-IIA inhibitor I) or iPLA2 (1 μM $PACOCF_3$) showed less than a 20% attenuation in PLA2 activation (see FIG. 1D). These data suggested that the major PLA2 subtype activated by low dose of ionizing radiation was the cytosolic isoform, $cPLA_2$.

To determine whether $cPLA_2$ participates in radiation-induced phosphorylation of ERK1/2 and Akt, HUVEC were pretreated with the inhibitors for $cPLA_2$, sPLA2 or iPLA2, irradiated, lysed 5 minutes later, and subjected to Western blot analysis. Inhibitors of $cPLA_2$, but not the inhibitors of sPLA2 or iPLA2, markedly decreased radiation-induced activation of Akt and ERK1/2, suggesting that $cPLA_2$ contributed to the radiation-induced activation of these kinases (see FIG. 1C).

Example 3

Experiments with Embryonic Fibroblasts from cPLA-deficient Mice

Figure 1E:
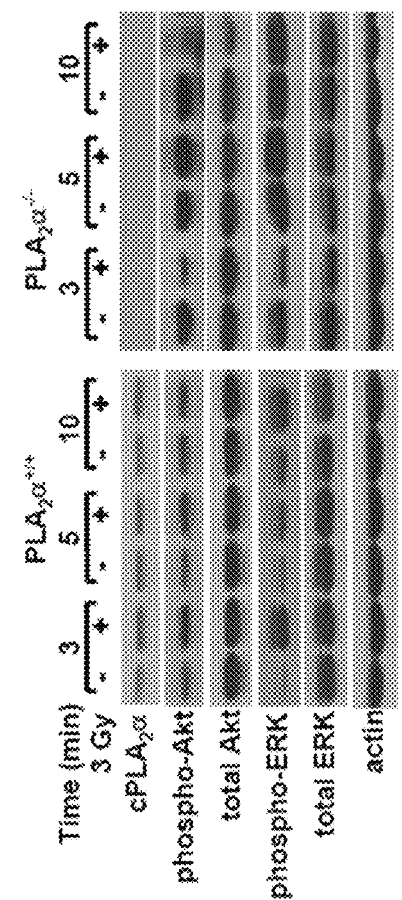

To verify the role of $cPLA_2$, phosphorylation of ERK1/2 and Akt was studied in irradiated MEF from $cPLA_2^{-/-}$ and wild type ($cPLA_2^{+/+}$) mice (Bonventre, 1999). Irradiation of $MEFcPLA_2^{+/+}$ with 3 Gy caused increased phosphorylation of ERK1/2 and Akt in a time course that was similar to that observed in HUVEC (compare FIG. 1E with FIG. 1A). However, in $MEFcPLA_2^{-/-}$, phosphorylation of both ERK1/2 and Akt decreased at 3 minutes after the start of irradiation and returned to the basal level at 5 and 10 minutes (see FIG. 1E). This genetic model supported the regulatory role of $cPLA_2$ in radiation-induced activation of pro-survival kinases Akt and ERK1/2.

Example 4

Examination of Changes in LPC Production Post-Irradiation

Figure 2A:
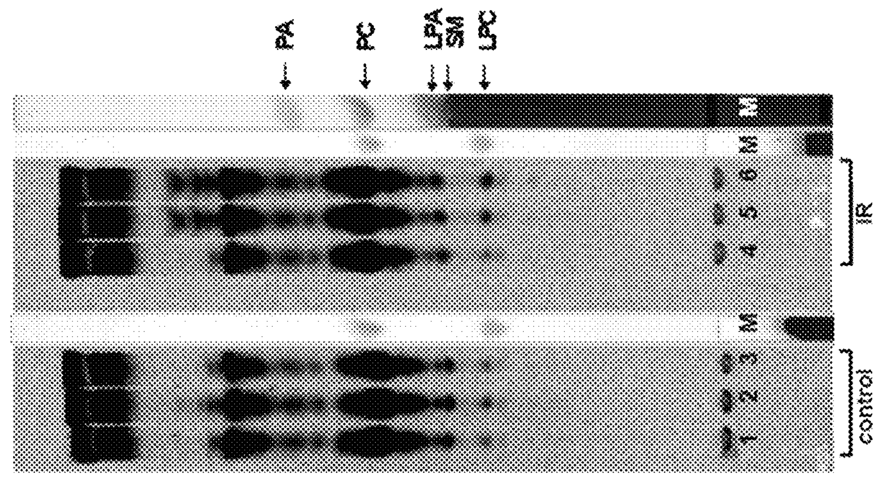
FIGS. 2A-2D present a radiograph of a thin layer chromatography (TLC) plate, a series of Western blots, and a bar graph demonstrating that radiation induces an increase in LPC production that leads to activation of ERK1/2 and Akt. HUVEC were labeled with $^3$H-palmitic acid for 90 minutes and irradiated with 3 Gy. Total cellular phospholipids were extracted 3 minutes after beginning of irradiation.
Figure 2B:
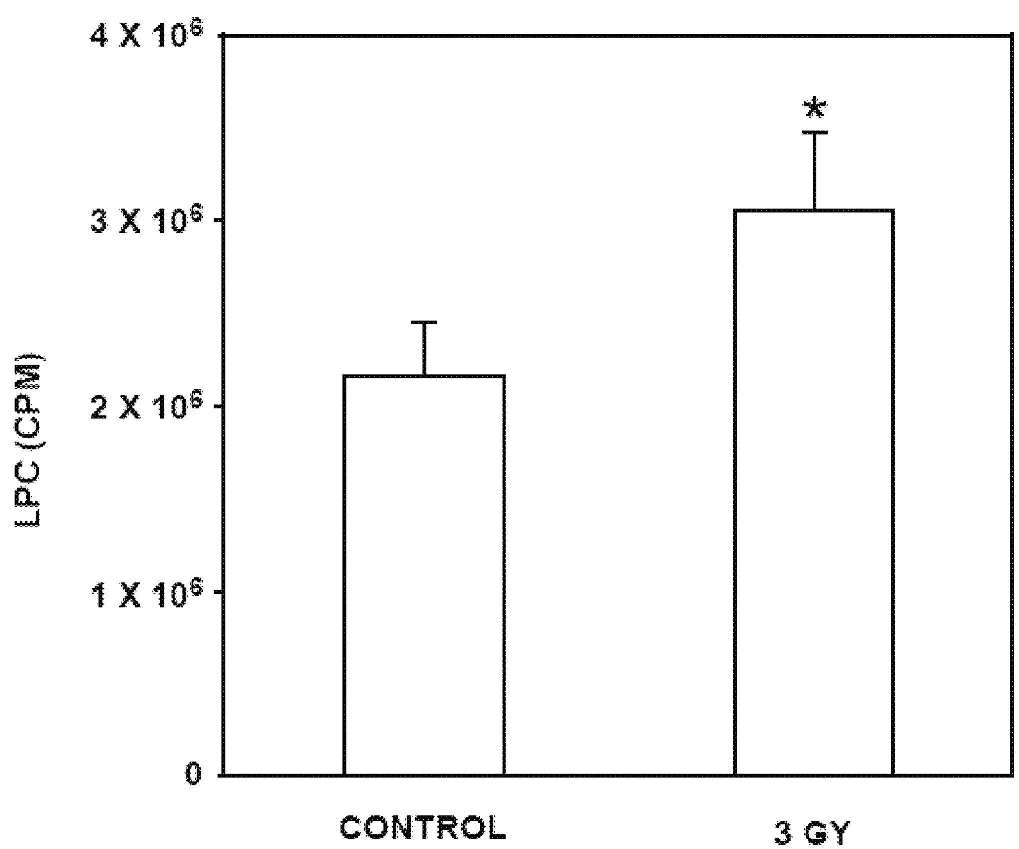

Since the most abundant phospholipid in the mammalian cell membrane is phosphatidylcholine, radiation-induced activation of $cPLA_2$ could lead to the increased production of LPC. To determine whether 3 Gy of radiation induces changes in LPC production, HUVEC were labeled with $^3$H-palmitic acid and followed by treatment with 3 Gy. TLC of extracted total lipids from the irradiated HUVEC revealed a statistically significant increase in LPC production of 1.5-fold as compared to untreated cells (see FIGS. 2A and 2B).

To determine whether this increase in LPC is involved in radiation-induced signal transduction, the HUVEC response to ionizing radiation was compared to the response triggered by exogenous LPC. Cellular survival and proliferation in response to LPC treatment are dependent on LPC concentration (Prokazova et al., 1998). Up to 25 μM of LPC have been reported to increase proliferation of HUVEC (Schaefer et al., 2004; Fujita et al., 2006), while higher concentrations promote cell death (Tsutsumi et al., 2006).

Figure 2C:
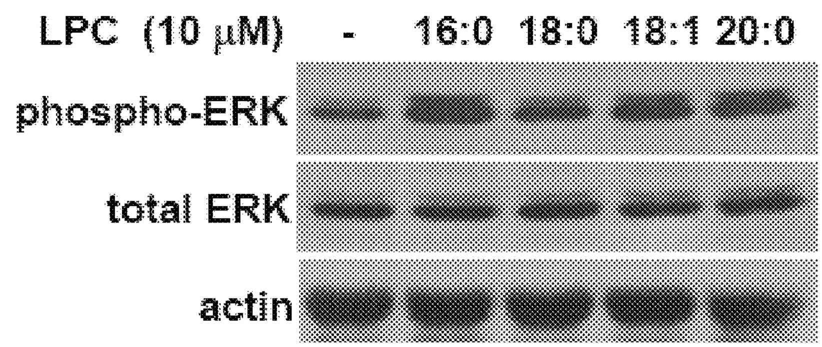
Figure 2D:
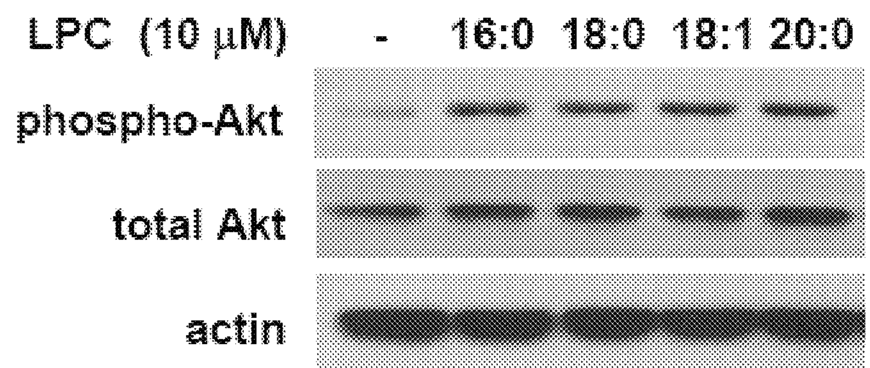
Figure 5:
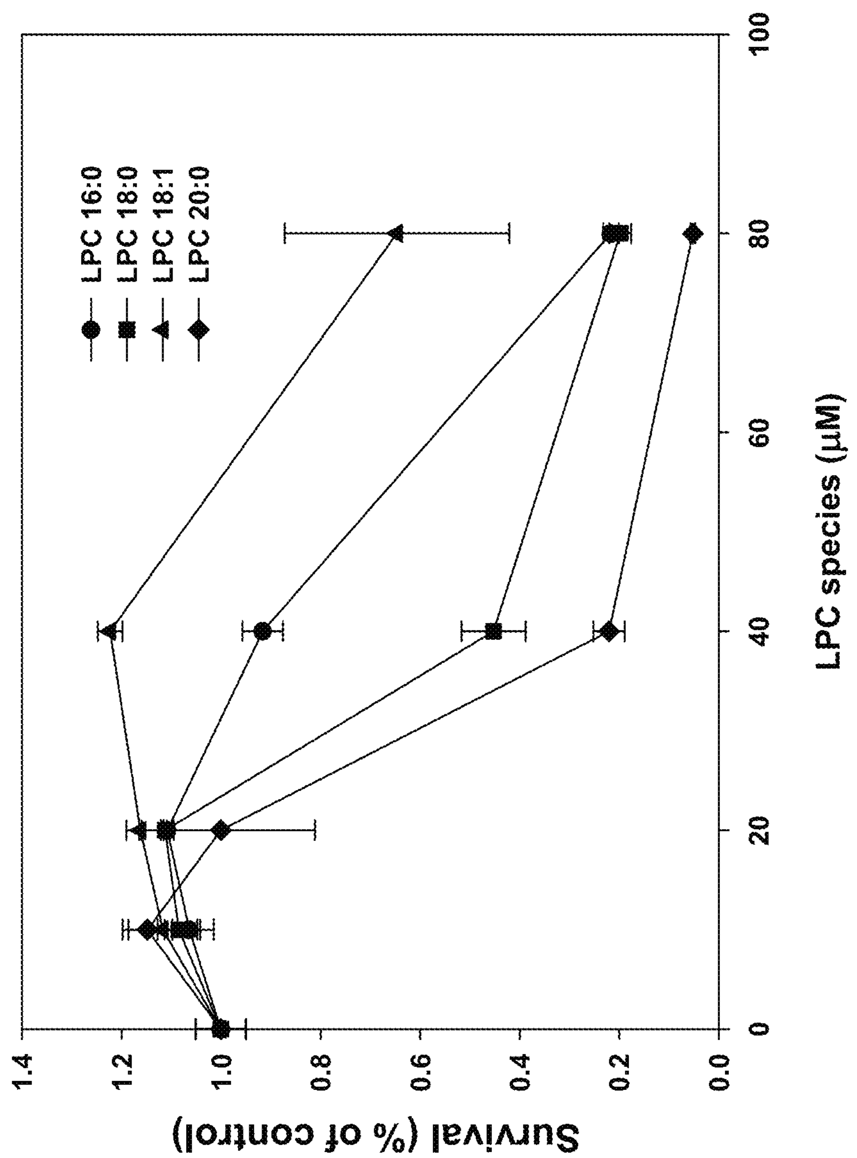
FIG. 5 are viability curves 24 hours after treatment with average percent of survival and SEM from three experiments demonstrating that different LPC species (up to 20 mM) do not affect HUVEC viability.

10 and 20 μM of four different LPC species exogenously added to HUVEC led to a slight increase in cell proliferation (up to 20%, see FIG. 5), Following this observations, a concentration of 10 μM was employed to study the effect of LPC on the activation of pro-survival pathways. Ten μM of various LPC species added to HUVEC resulted in ERK1/2 and Akt phosphorylation with the maximum phosphorylation occurring at 5 minutes for ERK1/2 (see FIG. 2C) and 10 minutes for Akt (see FIG. 2D). These time points correlated with the time course of radiation-induced activation of ERK1/2 and Akt (see FIG. 1A).

Similarly, Fujita and coworkers (Fujita et al., 2006), have shown that 20 μM LPC activated the same pro-survival kinases leading to increased cell proliferation. Their study also demonstrated LPC-dependent transactivation of FLK-1 (VEGFR2) followed by activation of cSrc. Interestingly, radiation-induced Akt phosphorylation is inhibited by specific inhibitors of VEGFR2, PI3K/Akt and cSrc (see Geng et al., 2001; Edwards et al., 2002; Geng et al., 2004; Cuneo et al., 2006; Tan et al., 2006). Taken together with data from $cPLA_2^{-/-}$ cells, these results suggested that $cPLA_2$-mediated signaling was required for radiation-induced activation of Akt and ERK1/2 pro-survival pathway.

Example 5

Cell Survival Assays

Figure 3A:
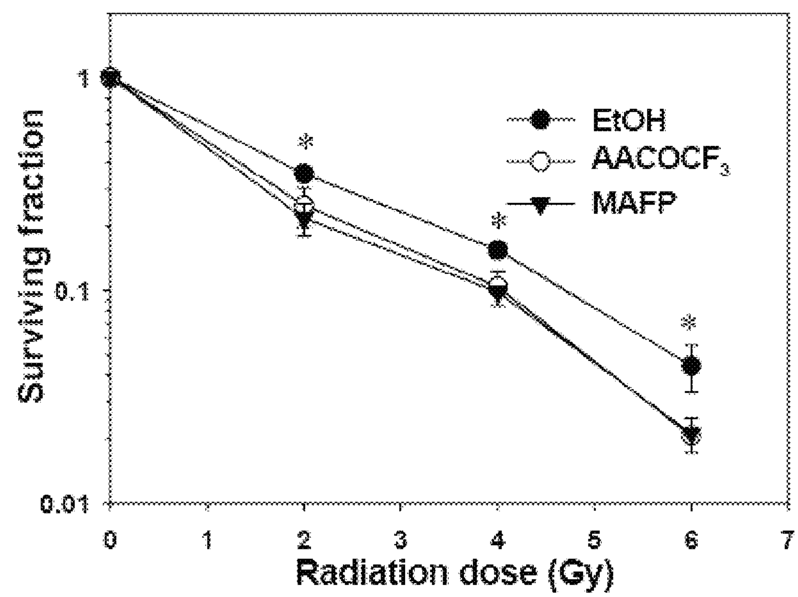
FIGS. 3A-3E present a graph, a series of Western blots, a bar graphs, and a series of photomicrographs demonstrating that inhibition of $cPLA_2$ increases the number of multinucleated giant cells and cyclin B1.
Figure 6A:
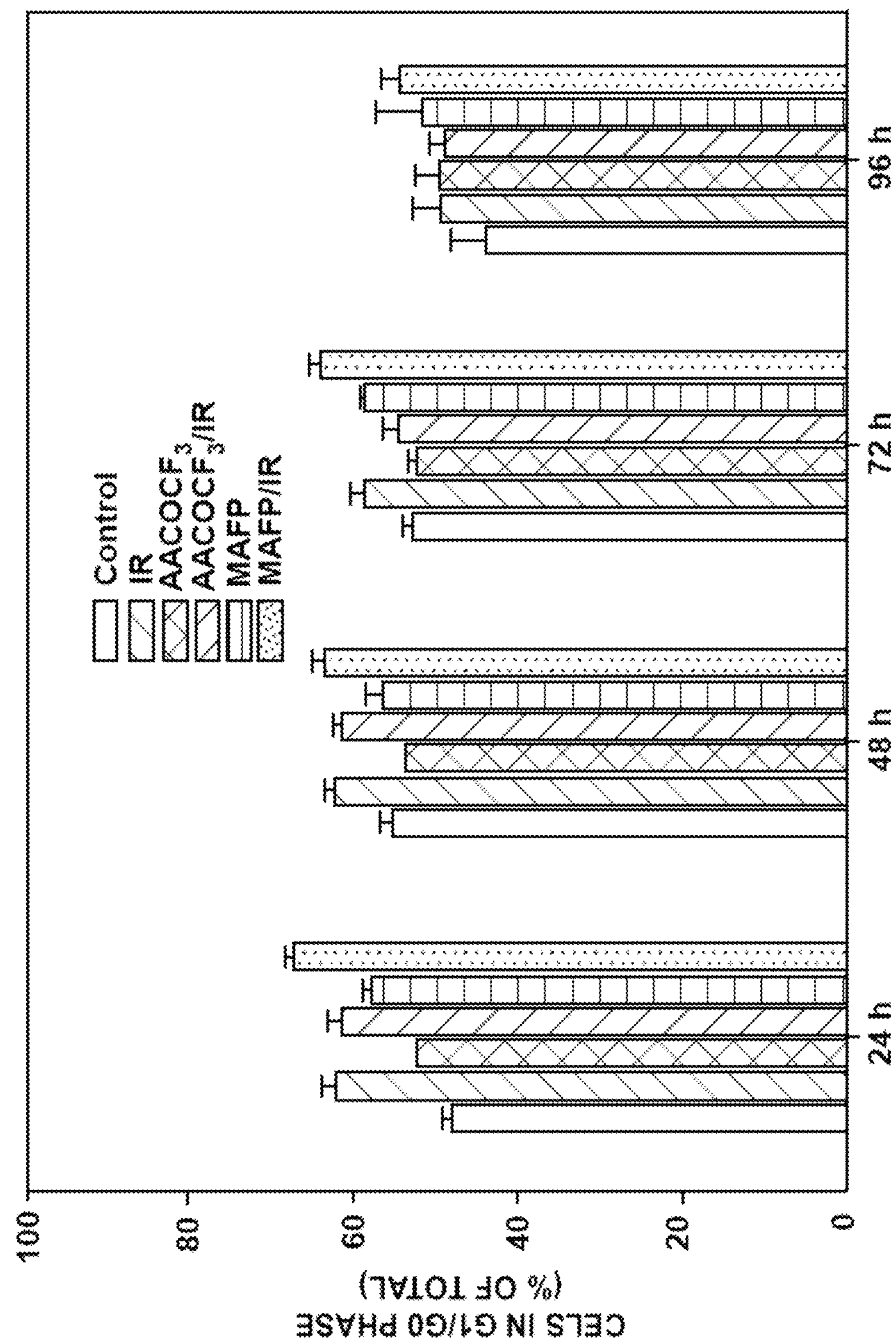
FIGS. 6A and 6B are a series of bar graphs of the average percent of cells in G1/G0 phase (FIG. 6A) and in S phase (FIG. 6B) with SEM from five experiments showing that inhibition of $cPLA_2$ does not affect cell cycle in irradiated HUVEC. Cells were treated with ethanol (EtOH) or $cPLA_2$ inhibitors for 30 minutes, irradiated with 3 Gy, collected 24, 48, 72, or 96 hours later, stained with propidium iodide (PI), and analyzed by flow cytometry.
Figure 6B:
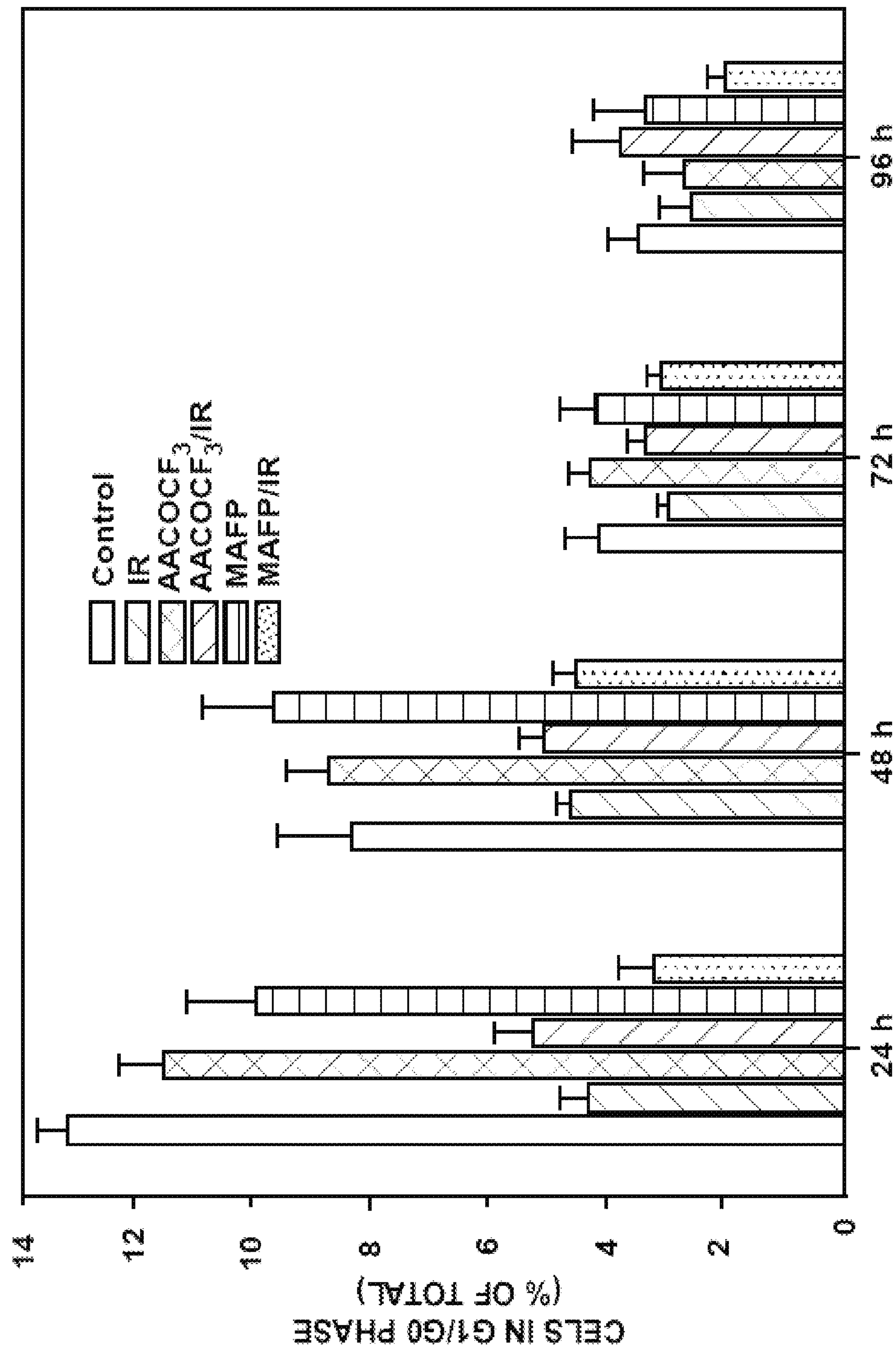

To study $cPLA_2$ contribution to the survival of irradiated endothelial cells, specific $cPLA_2$ inhibitors were employed in a number of cell survival assays. Clonogenic survival analysis showed that each inhibitor produced a statistically significant decrease in viability of HUVEC as compared to irradiation alone (see FIG. 3A). To determine the molecular mechanisms of this enhanced cell death, the effect of $cPLA_2$ inhibition on cell cycle regulation in irradiated endothelial cells was first tested. As expected (Hwang & Muschel, 1998), radiation alone caused a significant increase in G1/G0 phase concurrent with the decrease in S-phase at 24-48 hours (see FIG. 6). Similar results were observed in irradiated cells pretreated with $cPLA_2$ inhibitors (see FIG. 6). Although, did detect slight potentiation of the radiation effect was observed, it was not statistically significant.

Figure 3B:
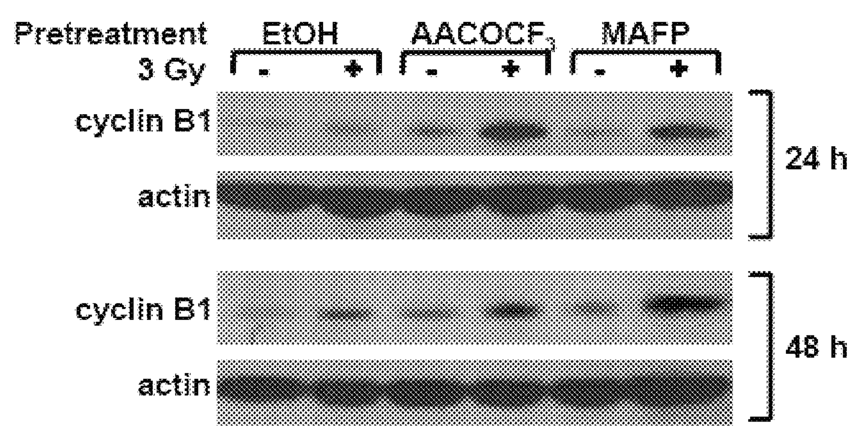

Levels of cyclin B1, which regulates activity of Cdkl and transition through cell cycle (Castedo et al., 2002; Kramer et al., 2004), were next examined. After 24-48 hours of treatment, cyclin B1 was dramatically increased in the cells treated with $cPLA_2$ inhibitors and radiation, while cells subjected to radiation alone showed a significant delay in cyclin B1 expression (see FIG. 3B). Since no significant differences in cell cycle between irradiated cells and cells treated with $cPLA_2$ inhibitors and radiation were detected, the observed cyclin B1 accumulation was cell cycle-independent, which might be associated with mitotic catastrophe (Castedo et al., 2002; Castedo et al., 2004; Ianzini et al., 2006).

Figure 3C:
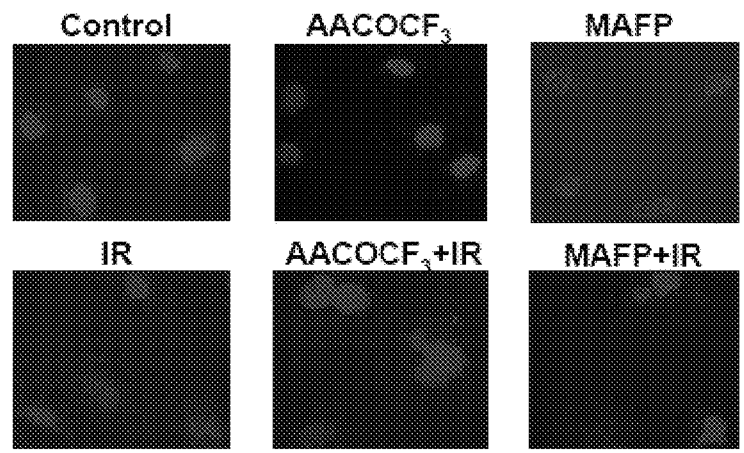
Figure 3D:
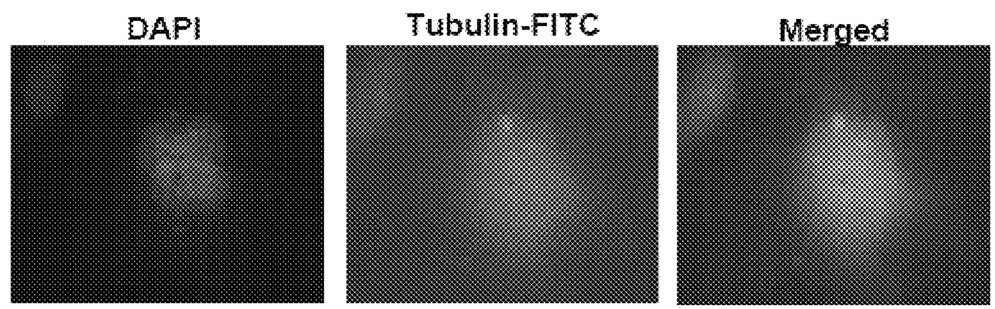
Figure 3E:
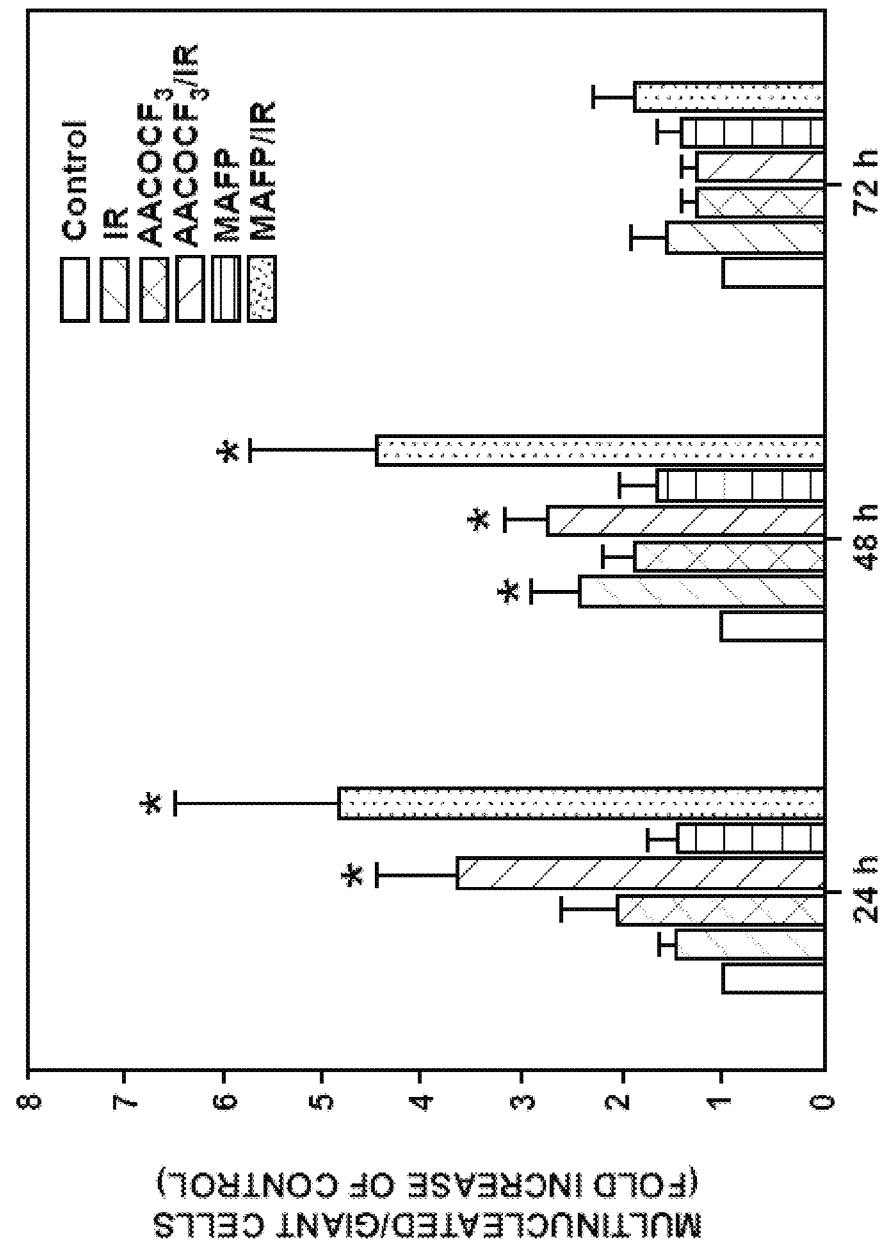

Next, the effect of $cPLA_2$ inhibition on the morphology of irradiated endothelial cells after 24-96 hours of treatment was determined. At 24-48 hours after combined treatment, a substantial increase in multinucleated giant cells up to 6-fold as compared to control cells was observed (see FIGS. 3C-3E). This effect was also detected in cells treated with radiation alone, but it was delayed and significantly less pronounced (see FIG. 3E). While the instant co-inventors do not wish to be bound by any particular theory of operation, the formation of giant multinucleated cells concurrent with cell cycle-independent accumulation of cyclin B1 implicated mitotic catastrophe occurring during the inhibition of $cPLA_2$-dependent pro-survival signaling in irradiated endothelial cells.

Example 6

Apoptosis in Irradiated Cells Treated with $cPLA_2$ Inhibitors

Generally, mitotic catastrophe progresses to cell death though apoptosis (Castedo et al., 2002; Castedo et al., 2004).

Figure 4A:
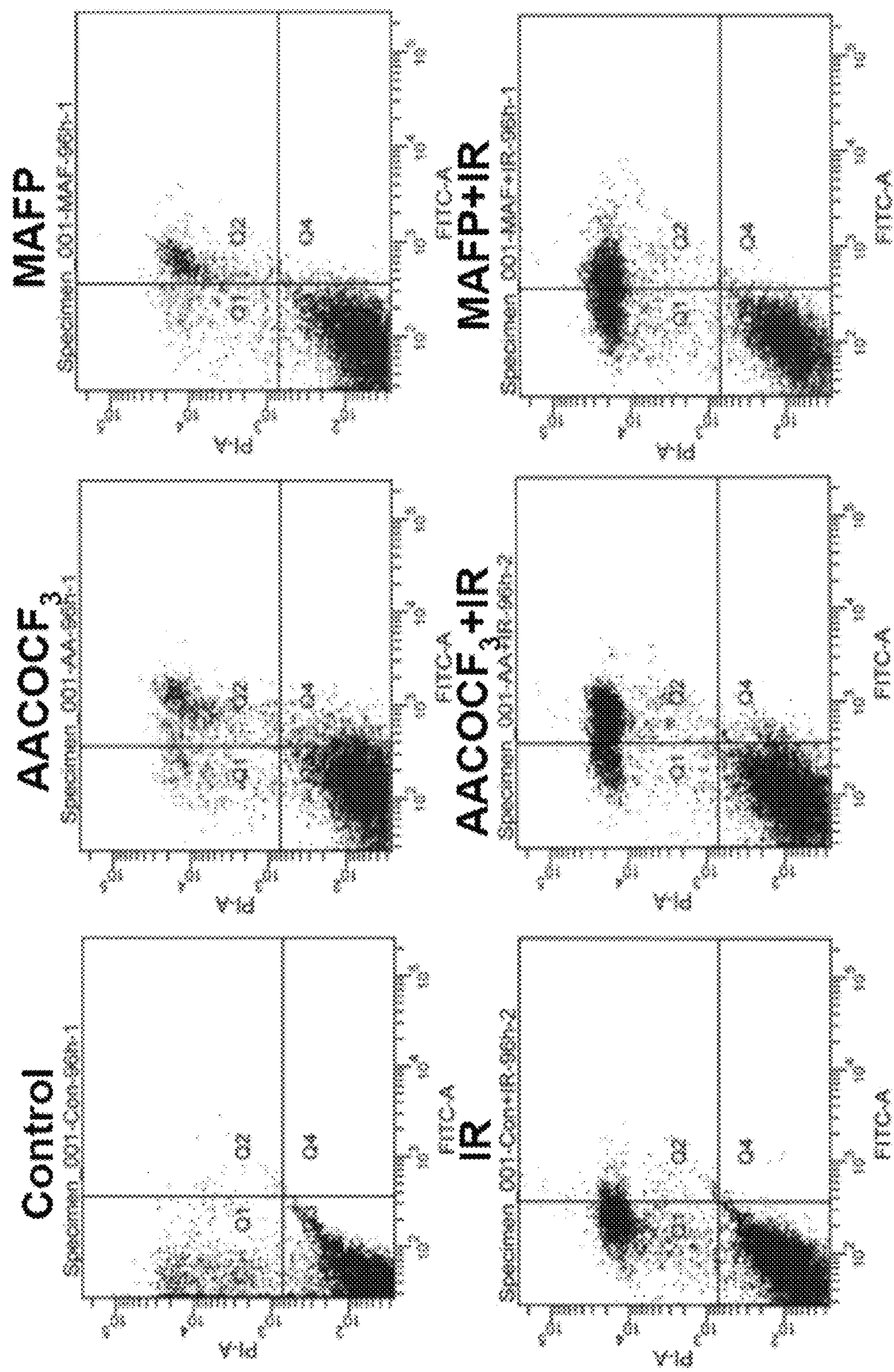
FIGS. 4A-4C present a series of FACS diagrams and a series of bar graphs demonstrating the results of inhibition of $cPLA_2$ results in a delayed program cell death.
Figure 4B:
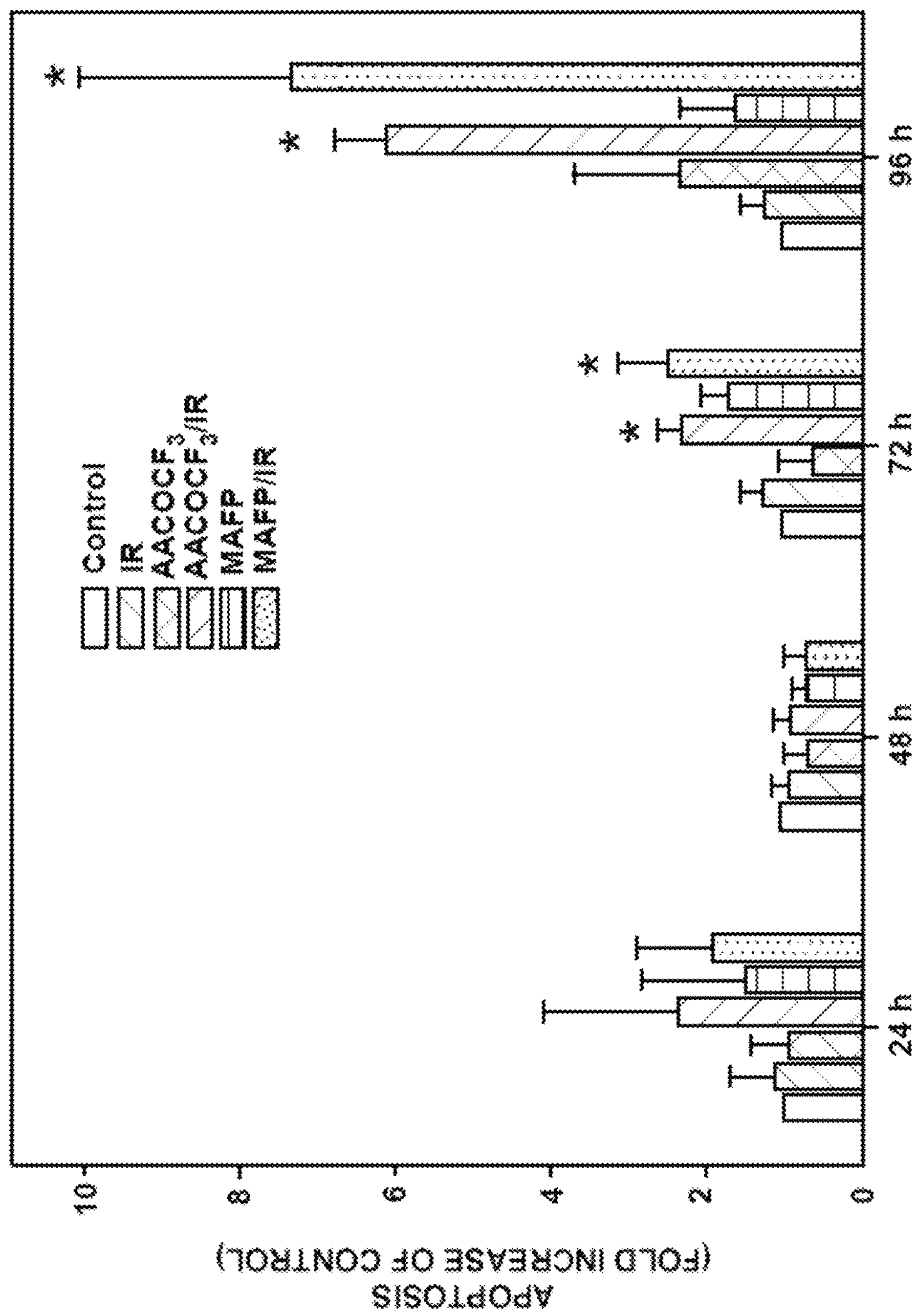
Figure 4C:
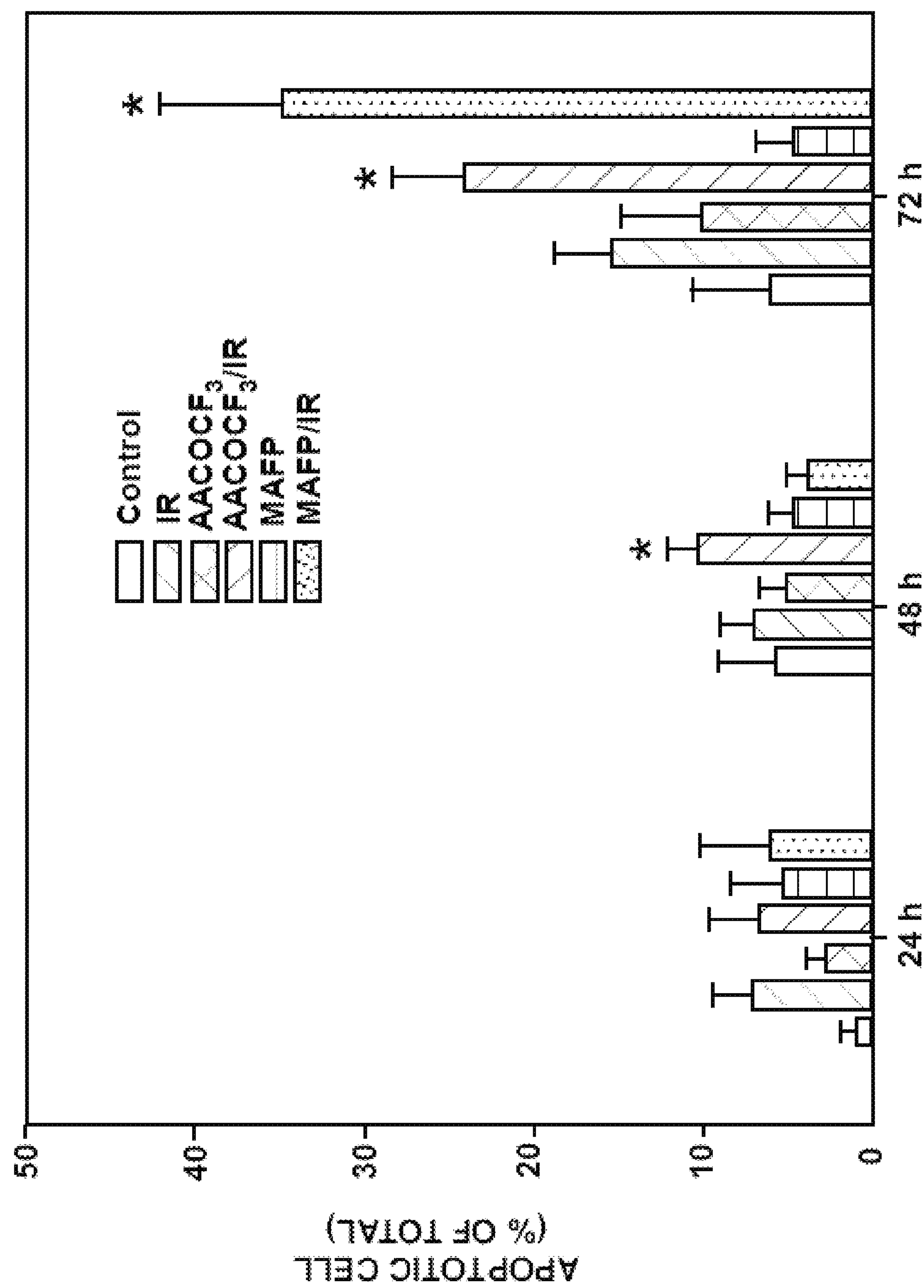

To determine whether apoptosis occurs in irradiated cells pretreated with $cPLA_2$ inhibitors, Annexin V levels and propidium iodide staining as well as nuclear morphology using DAPI staining were investigated. In both assays, an increase in programmed cell death at 24-48 hours after treatment was not detected (see FIG. 4). However, when cells were pretreated with $cPLA_2$ inhibitors prior to irradiation, a marked increase in Annexin V-positive cells by 2-3 fold was observed at 72 hours and 7-11 fold at 96 hours, as compared to control cells (see FIGS. 4A and 4B). Moreover, DAPI-staining showed a 30-40% increase at 72 hours after treatment (see FIG. 4C).

Example 7

Effects of $cPLA_2$ on Endothelial Functions in Irradiated HUVEC

Figure 8A:
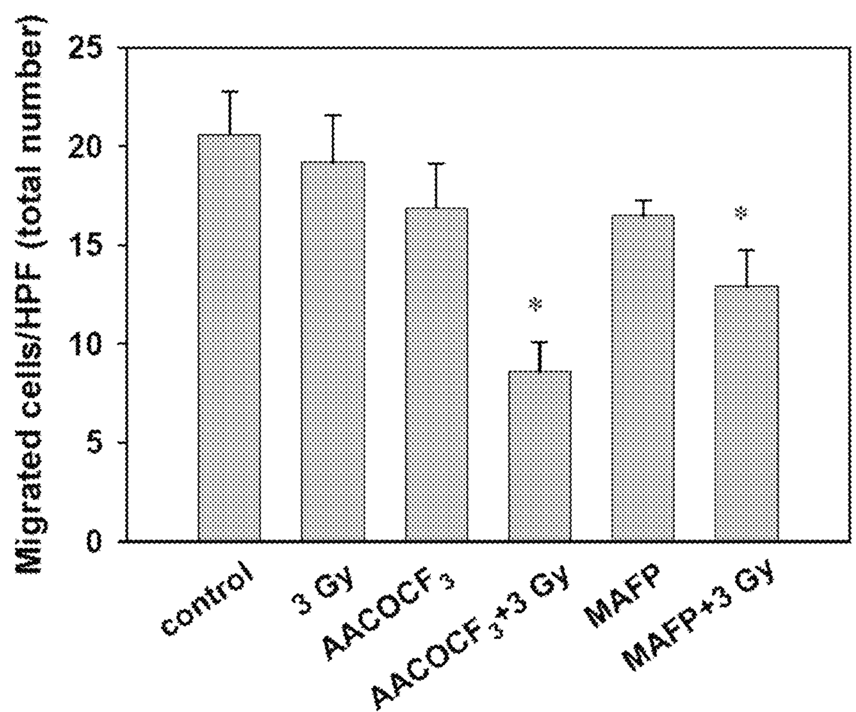
FIGS. 8A-8E depict the results of experiments showing that $cPLA_2$ inhibition decreased migration and tubule formation in irradiated HUVEC.
Figure 8B:
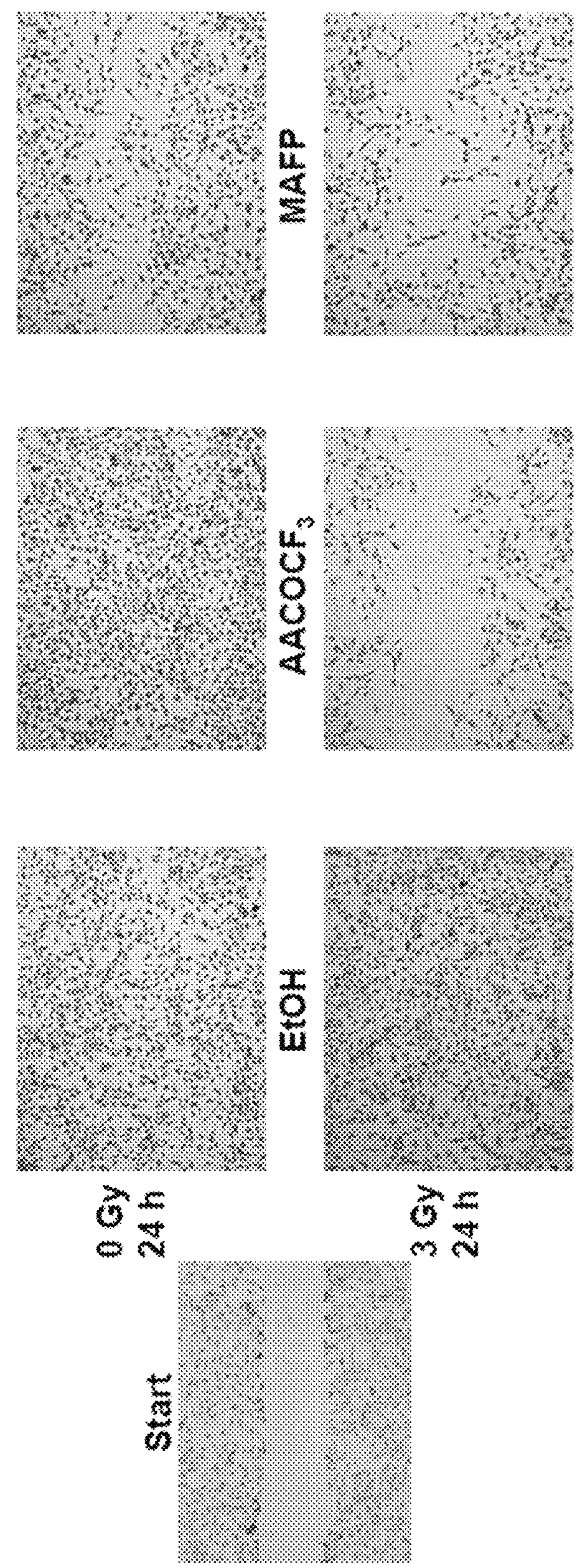
Figure 8C:
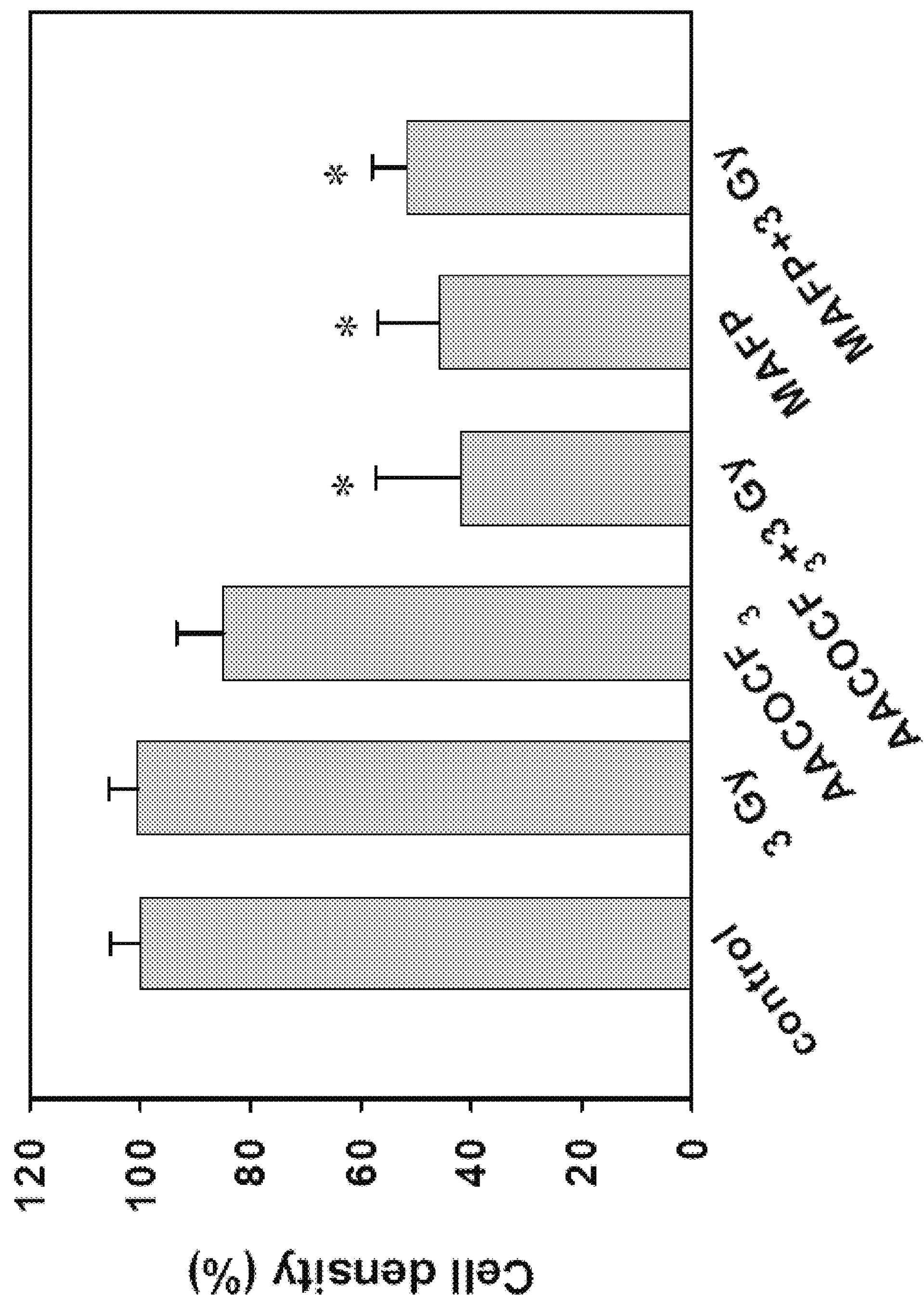

The role of $cPLA_2$ in HUVEC migration was investigating using two approaches: endothelial cell migration through the filter and endothelial cell gash closure (see FIGS. 8A-8C). In both assays, radiation alone or inhibition of $cPLA_2$ with $AACOCF_3$ alone resulted in a 15% decrease in HUVEC migration, which was not statistically significant (see FIGS. 8A-8C). Inhibition of $cPLA_2$ with MAFP alone demonstrated a greater decrease in gash closure than in migration through the filter (see FIGS. 8A-8C; 50% vs. 20%), possibly suggesting different mechanisms of $cPLA_2$ inhibition involved in each type of migration. However, inhibition of $cPLA_2$ with either $AACOCF_3$ or MAFP followed by irradiation maximally abolished HUVEC migration in both assays leaving only 40% of cells capable of migration (see FIGS. 8A-8C).

Figure 8D:
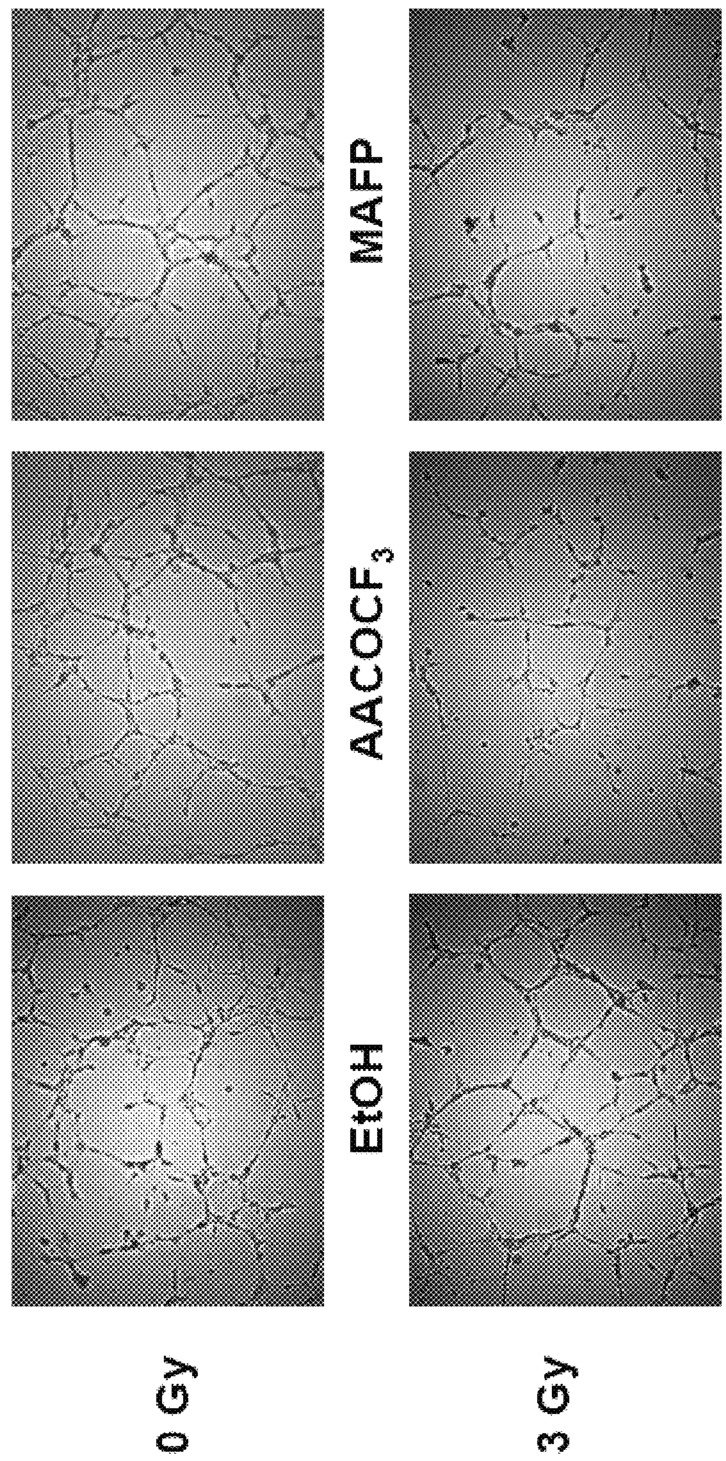
Figure 8E:
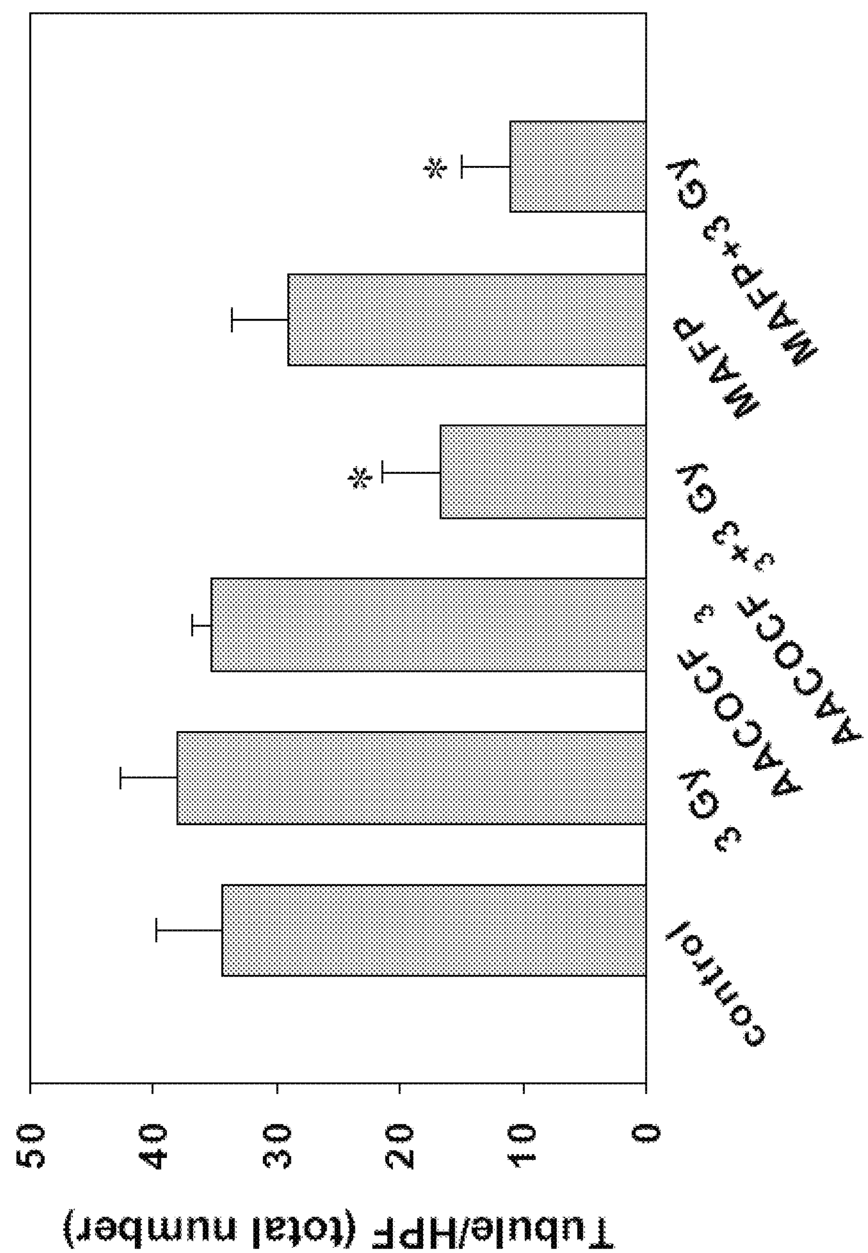

Inhibition $cPLA_2$ activity was also determined to affect endothelial tubule formation in irradiated HUVEC. Untreated cells attached to MATRIGEL™ (BD Biosciences, San Jose, Calif., USA) when plated and formed capillary-like structures within 24 hours following irradiation. Irradiated cells or cells treated with $cPLA_2$ inhibitors alone did not show significant difference in the number of capillary-like tubules as compared to that of untreated cells (see FIGS. 8D and 8E). However, irradiation combined with $cPLA_2$ inhibition caused a pronounced decrease of 3-fold (30% of control) in the number of formed tubules (see FIGS. 8D and 8E).

Example 8

Figure 9A:
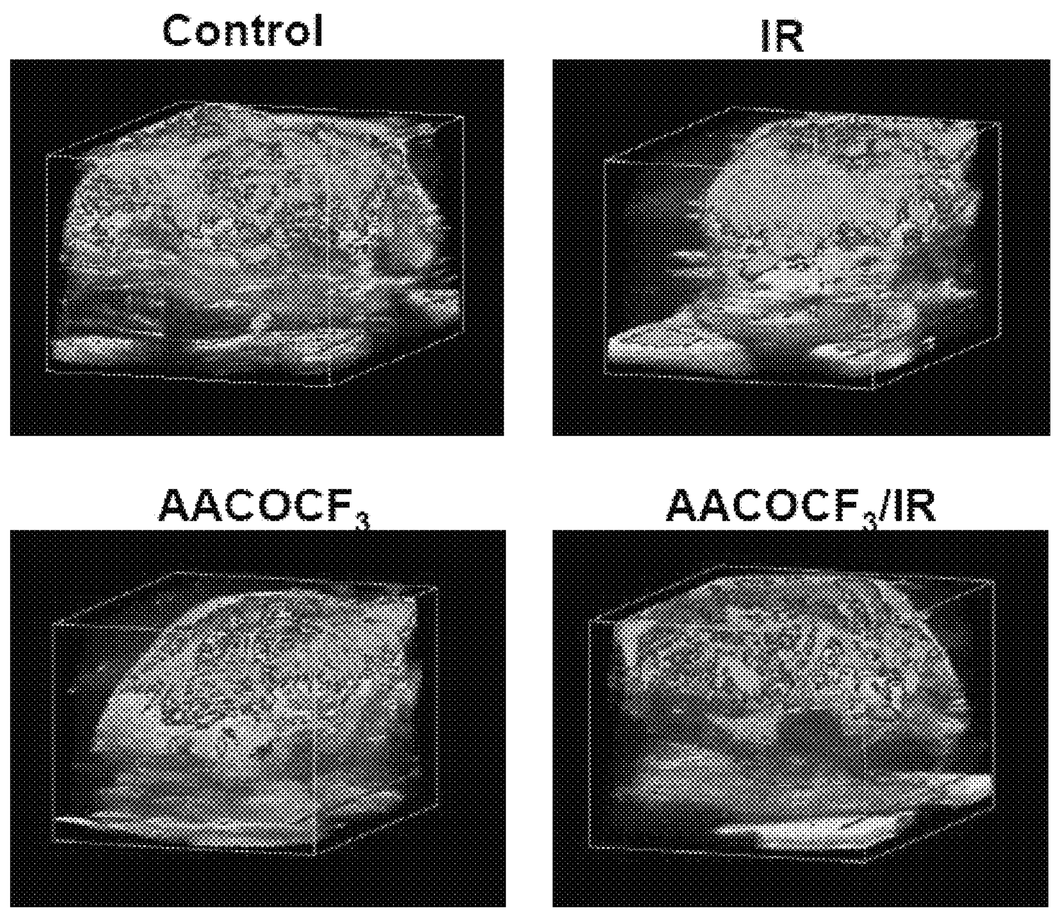
FIGS. 9A-9F depict the results of experiments showing that $cPLA_2$ inhibition led to decreased tumor vascularity and tumor size in irradiated mouse models.
Figure 9B:
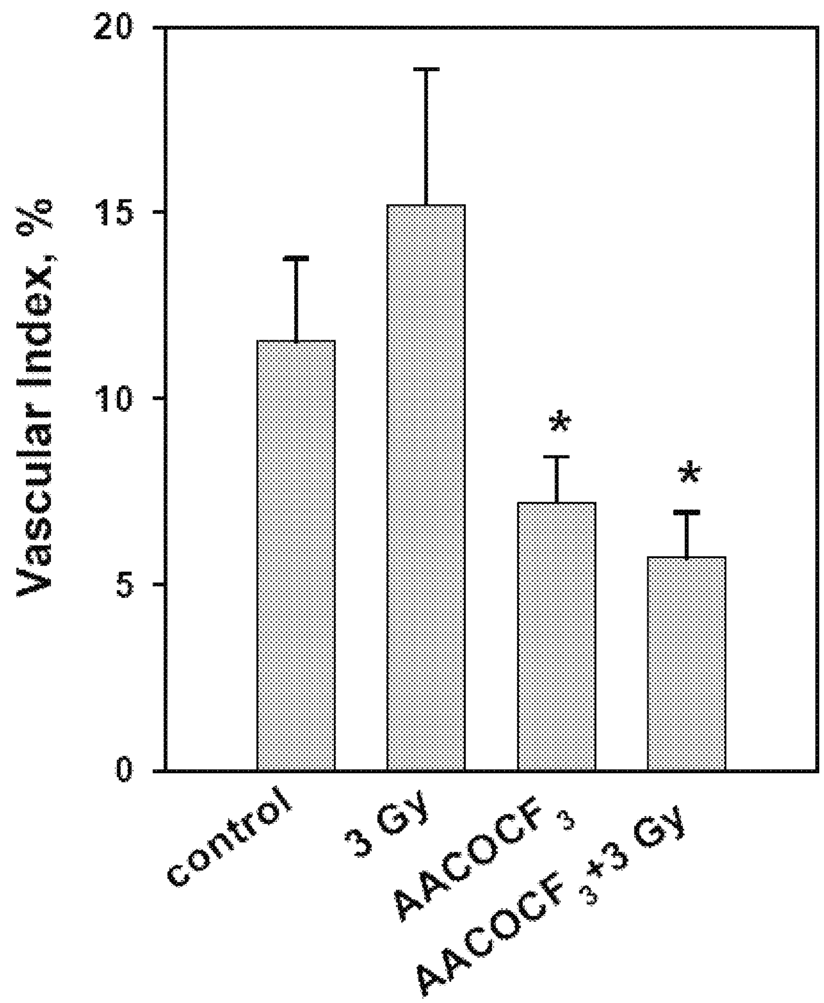

$cPLA_2$ Role in Tumor Vascularity and Tumor Size in an Irradiated Mouse Tumor Model The assessment of $cPLA_2$ inhibition for in vivo vascularity was performed in a heterotopic tumor model of C57BL/6 mice with Lewis Lung Carcinoma in the hind limb using Power Doppler sonography and vessel counts in tumor sections. After Power Doppler sonography, Vascular Index was calculated as the ratio of color coded pixels representing blood flow to the total pixel volume of the tumor (see FIGS. 9A and 9B). The average Vascular Indices were 12% and 15% for untreated and irradiated tumors, respectively. Treatment with $AACOCF_3$ resulted in a 1.6-fold decrease in tumor Vascular Index as compared to untreated mice (see FIGS. 9A and 9B; 7.5% vs. 12%). This decrease was further potentiated in mice that received a combined treatment of $AACOCF_3$ and radiation (see FIGS. 9A and 9B; 2-fold, 6% vs. 12%).

Figure 9C:
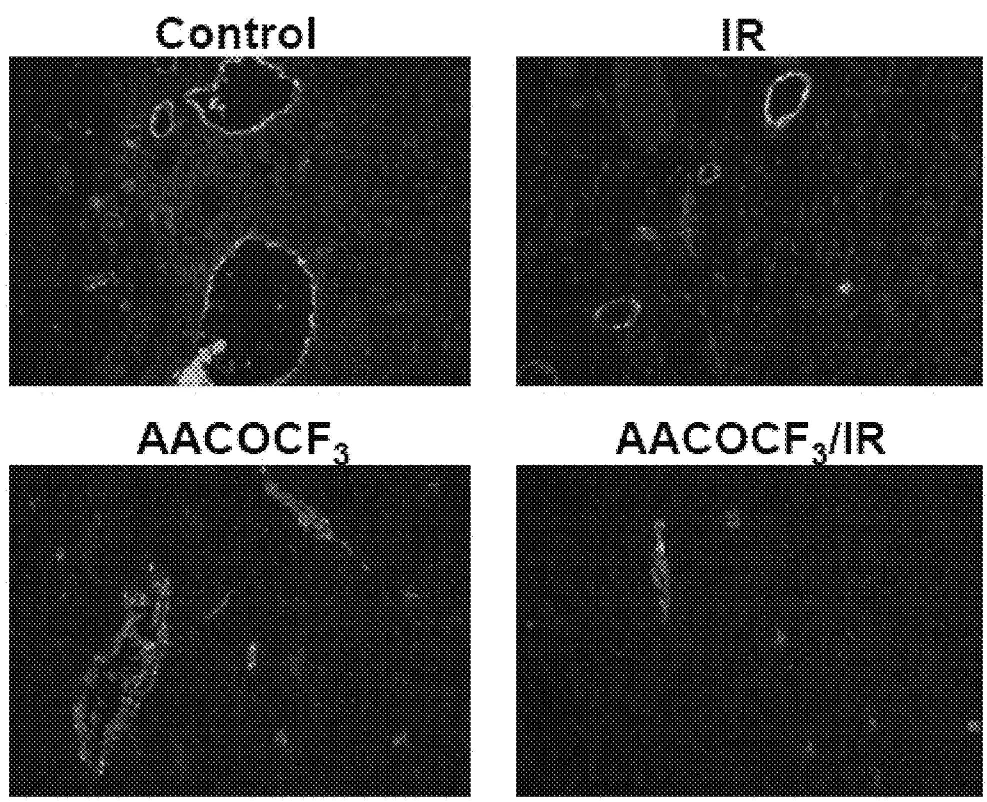
Figure 9D:
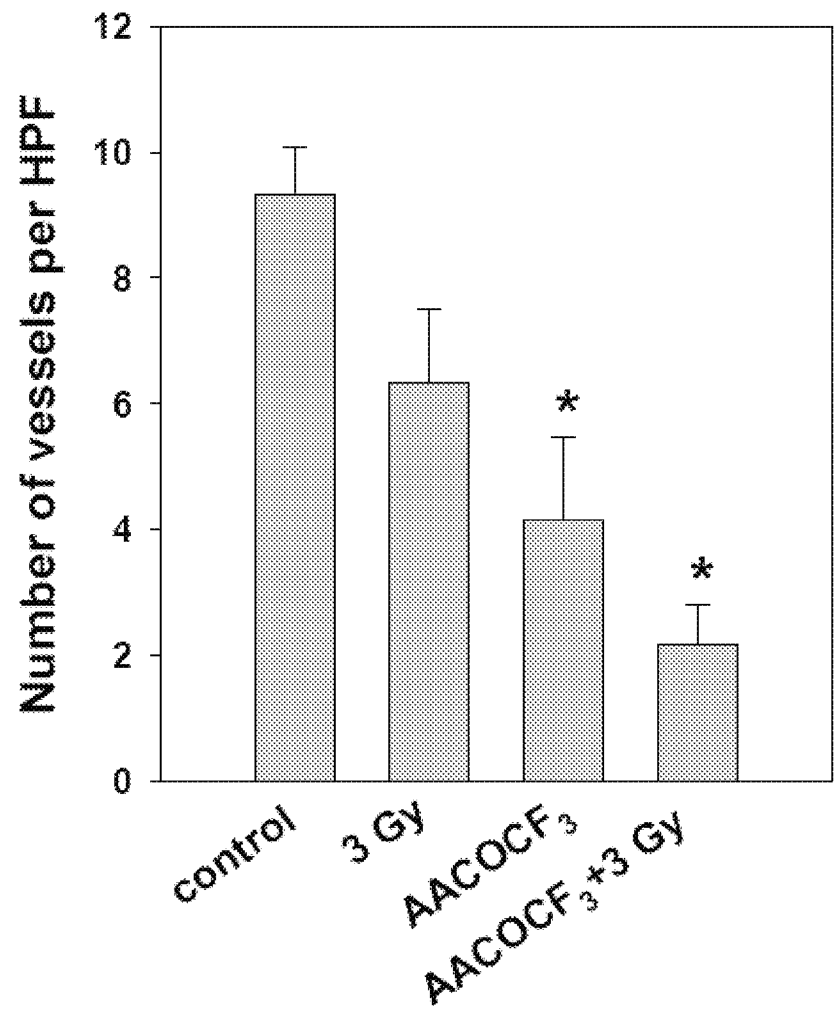

A similar trend in tumor vascularity was observed when tumor sections from treated mice were stained with anti-vWF antibody and examined for microvascular density (see FIGS. 9C and 9D). In comparison to vessel number in untreated mice (see FIGS. 9C and 9D; 10%), microscopic analysis revealed a significant decrease in vessel number in mice treated with $AACOCF_3$ followed by radiation (see FIGS. 9C and 9D; 2%).

Figure 9E:
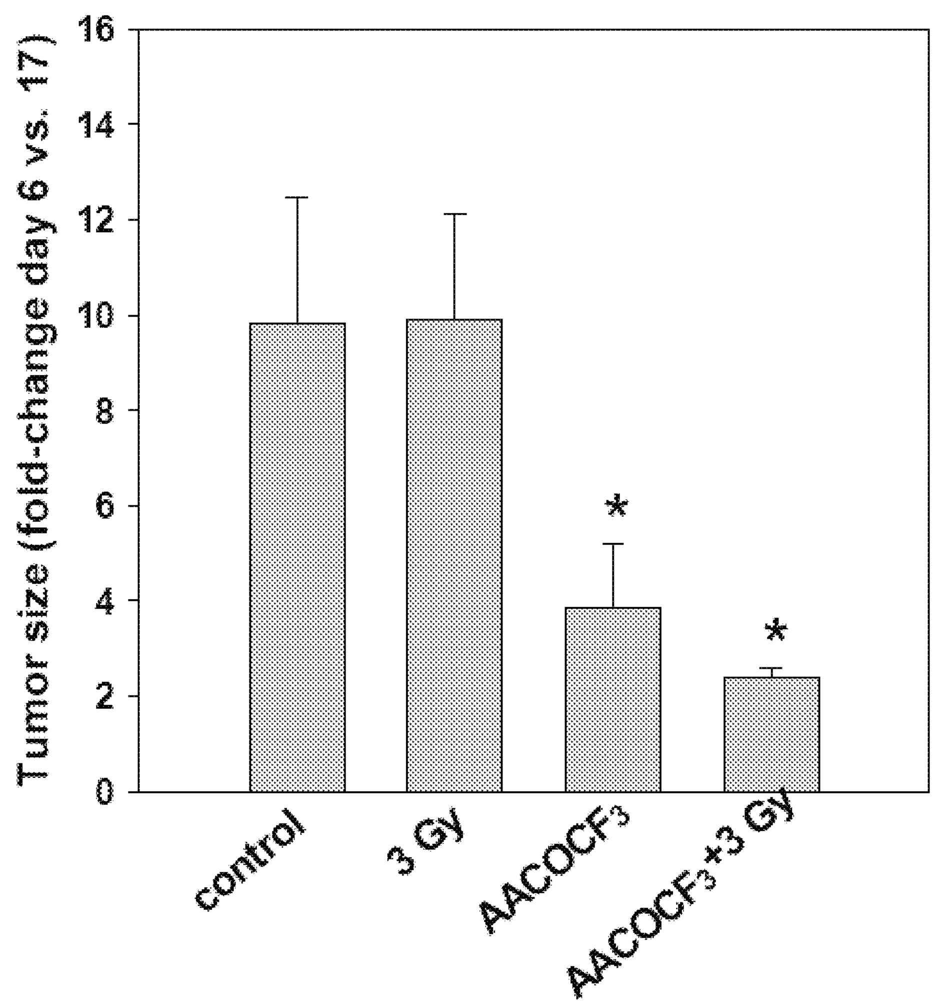
Figure 9F:
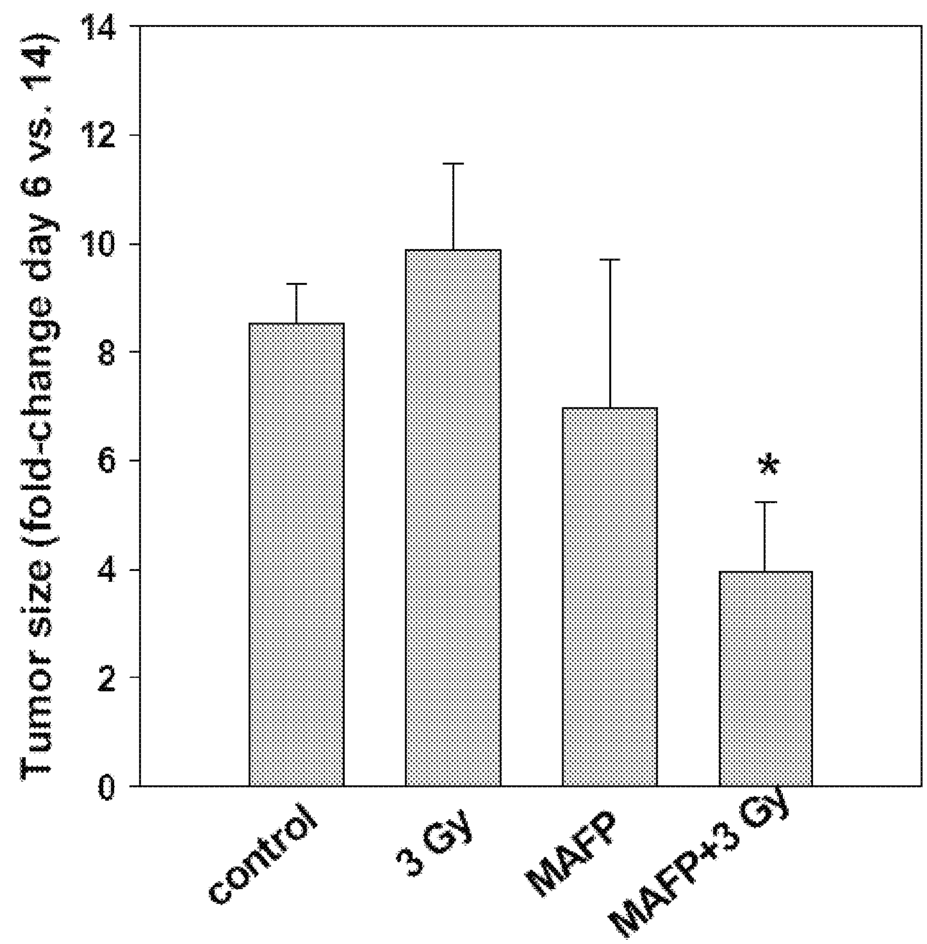

Power Doppler sonography was also used to estimate effects of $cPLA_2$ inhibition on tumor size. The same mouse tumor model and irradiation with the addition of a second $cPLA_2$ inhibitor, MAFP, was studied. Tumor size was measured over the course of the experiment. Treatment with radiation alone or inhibitors alone (10 mg/kg $AACOCF_3$ or 2 mg/kg for MAFP) led to a persistent decrease in the average tumor size which was not statistically significant. However, combined treatment resulted in statistically significant reduction of the average tumor size. This difference was especially pronounced when fold-changes in tumor size comparing first and last measurements were calculated (see FIG. 9E: 2-fold for $AACOCF_3$+3 Gy vs. 10-fold for control and 10-fold for 3 Gy; FIG. 9F: 4-fold for MAFP+3 Gy vs. 8.5-fold for control and 10-fold for 3 Gy). Interestingly, treatment with $AACOCF_3$ alone also resulted in statistically significant decrease in fold-change of tumor size, though it was less than for combined treatment (see FIG. 9E; 4-fold for $AACOCF_3$+3 Gy vs. 10-fold for control and 10-fold for 3 Gy), while treatment with MAFP alone produced results similar to control or irradiated groups (see FIG. 9F; 7-fold for MAFP vs. 8.5-fold for control and 10-fold for 3 Gy).

Discussion of the EXAMPLES

Clinically relevant doses of ionizing radiation trigger the activation of pro-survival signaling pathways in tumor vascular endothelium resulting in decreased therapeutic ratio of ionizing radiation. Disclosed herein is the discovery that activation of cytosolic phospholipase $A_2$ ($cPLA_2$) and production of the lipid second messenger lysophosphatidylcholine (LPC) are triggering events for radiation-induced activation of pro-survival kinases Akt and ERK1/2 in endothelial cells. This effect was confirmed using embryonic fibroblasts isolated from $CPLA_2^{-/-}$ and wild-type mice. Moreover, inhibition of $cPLA_2$ significantly enhanced radiation-induced cell death. This cell death was characterized by an increased number of multinucleated giant cells accompanied by accumulation of cyclin B1 within 24-48 hours of treatment and a delayed program cell death after 72-96 hours. These findings identify $cPLA_2$-dependent signaling pathway as a novel molecular target for development of cancer therapeutic agents.

Also disclosed herein are investigations into biological activities of lipid-derived second messengers that are immediately mobilized following irradiation. One such signaling pathway involves phospholipase A2 (PLA2), which consists of 3 main subtypes: cytosolic ($cPLA_2$), secretory (sPLA2) and intracellular Ca2+-independent (iPLA2). The family of PLA2s hydrolyze phospholipids at the sn-2-acyl ester bond, generating free fatty acids and lysophospholipids (Chakraborti, 2003). In mammalian cells, the sn-2-position of phospholipids is enriched with arachidonic acid (AA). On the other hand, the most abundant phospholipid in mammalian cell membranes is phosphatidylcholine.

Therefore, in addition to the release of free AA, the activation of $cPLA_2$ could lead to the increased production of lysophosphatidylcholine (LPC; Prokazova et al., 1998; Chakraborti, 2003; Hirabayashi et al., 2004). This biologically active lipid functions as the second messenger in signal transduction pathways, that regulate vascular proliferation, migration, expression of adhesion molecules and inflammation (Prokazova et al., 1998; Sugiyama et al., 1998; Murugesan et al., 2003; Fujita et al., 2006).

The studies disclosed herein thus suggest a sequence of molecular events in irradiated endothelial cells constituting an immediate signaling pathway activated by ionizing radiation. Activation of $cPLA_2$ results in production of LPC and subsequent phosphorylation of Akt and ERK1/2. Inhibition of this pathway enhanced radiation-induced cell death with an increased number of multinucleated giant cells accompanied by the accumulation of cyclin B1 and a delayed program cell death. By regulating endothelial cell survival, $cPLA_2$-dependent signaling pathway contributes to endothelial cell viability and presents a new set of potential molecular targets for tumor sensitization to radiotherapy.

REFERENCES

Adelman et al. (1983) *DNA* 2:183-193.
Advani et al. (1998) *Gene Ther* 5:160-165.
Allam et al. (1993) *Intl J Radiat Oncol Biol Phys* 27:303-308.
Alon et al. (1995) *Nat Med* 1:1024-1028.
Antonakopoulos et al. (1994) *Histopathology* 25:447-454.
Arap et al. (1998) *Science* 279:377-380.
Ausubel (ed.) (1995) *Short Protocols in Molecular Biology,* 3rd ed. Wiley, N.Y., United States of America.
Ausubel et al. (eds.) (1992) *Current Protocols in Molecular Biology*. Wiley, New York, N.Y., United States of America.
Baher et al. (1999) *Anticancer Res* 19:2917-2924.
Baillie et al. (1995) *Br J Cancer* 72:257-267.
Bass (2001) *Nature* 411:428-429.
Batzer et al. (1991) *Nucleic Acids Res* 19:5081.
Baumann et al. (1992) *Intl J Radiat Oncol Biol Phys* 23:803-809.
Bauminger & Wilchek (1980) *Methods Enzymol* 70:151-159.
Beaucage & Iyer (1993) *Tetrahedron* 49:1925-1963.
Becerril et al. (1999) *Biochem Biophys Res Commun* 255:386-393.
Beigelman et al. (1995) *J Biol Chem* 270:25702-25708.
Bell et al. (1999) *In Vitro Cell Dev Biol Anim* 35:533-542.
Bellon et al. (1997) *Bioconjugate Chem* 8:204-212.
Betageri et al. (eds.) (1993) *Liposome Drug Delivery Systems*. Technomic Publishing, Lancaster; Pa., United States of America.
Blanchard et al. (1992) *Mol Cell Biol* 12:5373-5385.
Bonventre (1999) *J Am Soc Nephrol* 10:404-412.
Brennan et al. (1998) *Biotechnol Bioeng* 61:33-45.
Brown & Attardi (2005) *Nat Rev Cancer* 5:231-237.
Burg et al. (1999) *Cancer Res* 59:2869-2874.
Burgin et al. (1996) *Biochemistry* 35:14090-14097.
Burlina et al. (1997) *Bioorg Med Chem* 5:1999-2010.
Canadian Patent Application No. 2,359,180
Cantley (2002) *Science* 296:1655-1657.
Caruthers et al. (1992) *Methods Enzymol* 211:3-19.
Castedo et al. (2002) *Cell Death Differ* 9:1287-1293.
Castedo et al. (2004) *Oncogene* 23:2825-2837.
Chakraborti et al. (2003) *Cell Signal* 15:637-665.
Cowan et al. (2006) *J Appl Physiol* 101:1127-35.
Cuneo et al. (2006) *Intl J Radiat Oncol Biol Phys* 64:1197-1203.
Datta et al. (1999) *Genes Dev* 13:2905-2927.
De Mesmaeker et al. (1994) in *Carbohydrate Modifications in Antisense Research*, American Chemical Society, Wash., D.C., Symposium Series No. 580:24-39.
Dent et al. (2003) *Oncogene* 22:5885-5896.
Dracopoli et al. (eds.) (1997) *Current Protocols in Human Genetics on CD-ROM*. John Wiley & Sons, New York, United States of America.
Dudek et al. (1997) *Science* 275:661-665.
Earnshaw & Gait (1998) *Biopolymers* 48:39-55.
Ebert & Bunn (1998) *Mol Cell Biol* 18:4089-4096.
Edwards et al. (2002) *Cancer Res* 62:4671-4677.
Elbashir et al. (2001a) *Nature* 411:494-498.
Elbashir et al. (2001 b) *Genes Dev* 15:188-200.
Elbashir et al. (2001c) *EMBO J* 20:6877-6888.
Ellerby et al. (1999) *Nat Med* 5:1032-1038.
European Patent No. 0 439 095.
Fang et al. (2000) *Biochem J* 352:135-143.
Fewell et al. (2001) *Mol Ther* 3:574-583.
Fire (1999) *Trends Genet* 15:358-363.
Fire et al. (1998) *Nature* 391:806-811.
Firth et al. (1995) *J Biol Chem* 270:21021-21027.
Freier et al. (1986) *Proc Natl Acad Sci USA* 83:9373-9377.
Fujita et al. (2006) *Endocrinology* 147:1377-1385.
Gao et al. (2002) *J Biol Chem* 277:31963-31971.
Garcia-Barros et al. (2003) *Science* 300:1155-1159.
GENBANK® Accession Nos. AAH56041; BC056041; CAH92005; CR859848; NM_001075864; NM_001081843; NM_001082072; NM_003706; NM_005090; NM_008869; NM_024420; NM_131295; NM_133551; NM_205423; NP_001069332; NP_001075312; NP_001075541; NP_003697; NP_005081; NP_005154; NP_032895; NP_077734; NP_571370; NP_598235; NP_990754; NT_004487.18; P27361; P28482; XM_537170; XP_537170.
Geng et al. (2001) *Cancer Res* 61:2413-2419.
Geng et al. (2004) *Cancer Res* 64:4893-4899.
Glover & Hames (1995) *DNA Cloning: A Practical Approach,* 2nd ed. IRL Press at Oxford University Press, Oxford/N.Y., United States of America.
Goldman et al. (1997) *Cancer Res* 57:1447-1451.
Gorski et al. (1999) *Cancer Res* 59:3374-3378.
Graeven et al. (1999) *J Cancer Res Clin Oncol* 125:621-629.
Greenberg et al. (1994) *Mol Endocrinol* 8:230-239.
Gregoriadis (ed) (1993) *Liposome Technology,* 2nd ed. CRC Press, Boca Raton, Fla., United States of America.
Grugel et al. (1995) *J Biol Chem* 270:25915-25919.
Haimovitz-Friedman et al. (1994) *J Exp Med* 180:525-535.
Hallahan & Virudachalam (1999) *Radiat Res* 152:6-13.
Hallahan et al. (1995) *Nat Med* 1:786-791.
Hallahan et al. (1996) *Cancer Res* 56:5150-5155.
Hallahan et al. (1998) *Cancer Res* 58:5216-5220.
Hallahan et al. (2001) *J Control Release* 74:183-191.
Hammond et al. (2000) *Nature* 404:293-296.
Harlow & Lane (1988) *Antibodies: A Laboratory Manual*. Cold Spring Harbor Laboratory Press, Cold Spring Harbor, N.Y., United States of America.
Hawiger & Timmons (1992) *Methods Enzymol* 215:228-243.
Hawiger et al. (1989) *Biochemistry* 28:2909-2914.
Hilmas & Gillette (1975) *Radiat Res* 61:128-143.
Hirabayashi et al. (2004) *Biol Pharm Bull* 27:1168-1173.
Hunziker & Leumann (1995) in *Modern Synthetic Methods*, VCH, Basel, Switzerland 331-417.
Hwang & Muschel (1998) *Radiat Res* 150:S52-59.
Ianzini et al. (2006) *Cancer Cell Intl* 6:11.
Ito et al. (1991) *Cancer Res* 51:255-260.
Janoff (ed) (1999) *Liposomes: Rational Design*. M. Dekker, New York, United States of America.
Johnson (1976) *Intl J Radiat Oncol Biol Phys* 1:659-670.
Kallman et al. (1972) *Cancer Res* 32:483-49.
Karpeisky et al. (1998) *Tetrahedron Lett* 39:1131-1134.
Katoh et al. (1995) *Cancer Res* 55:5687-5692.
Kauffmann-Zeh et al. (1997) *Nature* 385:544-548.
Kelley et al. (1999) *J Biol Chem* 274:26393-26398.

Kieser et al. (1994) *Oncogene* 9:963-969.
Kirpotin et al. (1997) *Biochemistry* 36:66-75.
Kolesnick & Fuks (2003) *Oncogene* 22:5897-5906.
Kramer et al. (2004) *Cell Cycle* 3:1390-1393.
Kufe & Weichselbaum (2003) *Cancer Biol Ther* 2:326-329.
Kurihara et al. (2000) *J Clin Invest* 106:763-771.
Kyte & Doolittle (1982) *J Mol Biol* 157:105-132.
Labat-Moleur et al. (1996) *Gene Ther* 3:1010-1017.
Lammering et al. (2004) *Clin Cancer Res* 10:6732-6743.
Lasic & Martin (eds.) (1995) *STEALTH® Liposomes*. CRC Press, Boca Raton, Fla., United States of America.
Lee et al. (2000) *Anticancer Res* 20:417-422.
Li et al. (1994) *Leuk Lymphoma* 13:65-70.
Li et al. (2005) *Am J Physiol Heart Circ Physiol* 289:H2592-601.
Limbach et al. (1994) *Nucleic Acids Res* 22:2183-2196.
Lio et al. (1996) *Biochim Biophys Acta* 1302:55-60.
Liu et al. (1995) *Biochem Biophys Res Commun* 217:721-727.
Loakes (2001) *Nucleic Acids Res* 29:2437-2447.
Manome et al. (1994) *Cancer Res* 54:5408-5413.
Marin et al. (1997) *Mol Med Today* 3:396-403.
Maruyama-Tabata et al. (2000)*Gene Ther* 7:53-60.
McMahon (2000) *Oncologist* 5:3-10.
Mesner et al. (1997) *Adv Pharmacol* 41:461-499.
Miyagishi & Taira (2002) *Nat Biotechnol* 20:497-500.
Murugesan et al. (2003) *J Mol Cell Cardiol* 35:1375-1384.
Neri et al. (1997) *Nat Biotechnol* 15:1271-1275.
Nykanen et al. (2001) *Cell* 107:309-321.
Ohtsuka et al. (1985) *J Biol Chem* 260:2605-2608.
Packer (1999) *Arch Neurol* 56:421-425.
Park et al. (1997) *Cancer Lett* 118:153-160.
Pasqualini & Ruoslahti (1996) *Nature* 380:364-366.
Pasqualini et al. (1997) *Nat Biotechnol* 15:542-546.
PCT International Patent Application Publication Nos. WO 91/03162; WO 92/07065; WO 92/07065; WO 92/07065; WO 93/15187; WO 93/15187; WO 93/15187; WO 93/23569; WO 97/26270; WO 98/10795; WO 98/13526; WO 99/07409; WO 99/32619; WO 99/32619; WO 99/54459; WO 00/01846; WO 00/44895; WO 00/44914; WO 00/44914; WO 00/63364; WO 01/04313; WO 01/29058; WO 01/36646; WO 01/36646; WO 01/68836; WO 01/75164; WO 01/92513; WO 02/44321.
Perrault et al. (1990) *Nature* 344:565.
Pieken et al. (1991) *Science* 253:314-317.
Prokazova et al. (1998) *Biochemistry* (*Mosc*), 63:31-37.
Radisavljevic et al. (2000) *J Biol Chem* 275:20770-20774.
Riendeau et al. (1994) *J Biol Chem* 269:15619-15624.
Rossolini et al. (1994) *Mol Cell Probes* 8:91-98.
Saltzman & Fung (1997) *Adv Drug Deliv Rev* 26:209-230.
Sambrook & Russell (eds.) (2001) *Molecular Cloning: A Laboratory Manual* (Third Edition), Cold Spring Harbor Laboratory Press, Cold Spring Harbor, N.Y., United States of America.
Scaringe et al. (1990) *Nucleic Acids Res* 18:5433-5441.
Schaefer et al. (2004) *Vascul Pharmacol* 41:67-73.
Scharfmann et al. (1991) *Proc Natl Acad Sci USA* 88:4626-4630.
Schmidt-Ullrich et al. (2000) *Radiat Res* 153:245-257.
Semenza & Wang (1992) *Mol Cell Biol* 12:5447-5454.
Shabarova et al. (1991) *Nature* 359:843-845.
Shintani et al. (2000) *Jpn J Cancer Res* 91:1051-1057.
Silhavy et al. (1984) *Experiments with Gene Fusions*. Cold Spring Harbor Laboratory, Cold Spring Harbor, New York, United States of America.
Somervaille et al. (2001) *Blood* 98:1374-1381.
Song et al. (1972) *Radiology* 104:693-697.
Staba et al. (1998) *Gene Ther* 5:293-300.
Sugiyama et al. (1998) *Arterioscler Thromb Vasc Biol* 18:568-576.
Taghian et al. (1993) *Intl J Radiat Oncol Biol Phys* 25:243-249.
Tam et al. (2000) *Gene Ther* 7:1867-1874.
Tan & Hallahan (2003) *Cancer Res* 63:7663-7667.
Tan et al. (2006) *Cancer Res* 66:2320-2327.
Tijssen (1993) *Laboratory Techniques in Biochemistry and Molecular Biology-Hybridization with Nucleic Acid Probes*, part I chapter 2, Elsevier, New York, N.Y., United States of America.
Ting et al. (1991) *Intl J Radiat Biol* 60:335-339.
Truman et al. (2005) *J Biol Chem* 280:23262-23272.
Tsutsumi et al. (2006) *Biol Pharm Bull* 29:907-910.
Turner et al. (1987) *Cold Spring Harb Symp Quant Biol* LII:123-133.
U.S. Patent Application Publication No. 20030175703.
U.S. Pat. Nos. 4,196,265; 4,235,871; 4,551,482; 4,551,482; 4,554,101; 4,946,778; 5,011,634; 5,091,513; 5,111,867; 5,132,405; 5,260,203; 5,270,163; 5,334,711; 5,334,711; 5,490,840; 5,510,103; 5,567,588; 5,574,172; 5,627,053; 5,632,991; 5,651,991; 5,667,988; 5,672,695; 5,677,427; 5,683,867; 5,688,931; 5,702,892; 5,714,166; 5,716,824; 5,780,225; 5,786,387; 5,840,479; 5,849,877; 5,854,027; 5,854,038; 5,855,900; 5,858,410; 5,892,019; 5,922,254; 5,922,356; 5,922,545; 5,948,647; 5,948,767; 5,985,279; 5,994,392; 5,998,203; 6,001,311; 6,054,561; 6,054,561; 6,056,938; 6,057,098; 6,071,890; 6,090,925; 6,106,866; 6,120,787; 6,127,339; 6,132,766; 6,174,708; 6,180,084; 6,190,700; 6,197,333; 6,200,598; 6,210,707; 6,217,886; 6,221,958; 6,238,704; 6,238,705; 6,245,740; 6,248,878; 6,262,127; 6,267,981; 6,287,587; 6,296,832; 6,296,842; 6,300,074; 6,312,713; 6,335,035; 6,500,853; 6,506,559; 6,635,771; 6,706,482; 6,797,708; 6,855,496; 6,924,391; 7,067,649; 7,176,295.
Uhiman & Peyman (1990) *Chem Rev* 90:543-549.
Usman & Cedergren (1992) *Trends Biochem Sci* 17:334-339.
Usman et al. (1987) *J Am Chem Soc* 109: 7845-7854.
Usman et al. (1994) *Nucleic Acids Symp Ser* 31:163-164.
Usman et al. (1996) *Curr Opin Struct Biol* 6:527-533.
Valter et al. (1999) *Cancer Res* 59:5608-5614.
Verma & Eckstein (1998) *Annu Rev Biochem* 67:99-134.
Walker et al. (1980) *N Engl J Med* 303:1323-1329.
Wallner et al. (1989) *Intl J Radiat Oncol Biol Phys* 16:1405-1409.
Wang et al. (1999) *Cancer Res* 59:1464-1472.
Weiner & Chun (1999) *Proc Natl Acad Sci USA* 96:5233-5238.
Wianny & Zernicka-Goetz (1999) *Nature Cell Biol* 2:70-75.
Williams et al. (1993) *J Clin Invest* 92:503-508.
Wincott & Usman (1997) *Methods Mol Bio* 74:59-68.
Wincott et al. (1995) *Nucleic Acids Res* 23:2677-2684.
Wymann & Pirola (1998) *Biochim Biophys Acta* 1436:127-150.
Yacoub et al. (2006) *Endocr Relat Cancer* 13 Suppl 1:S99-S114.
Yamaura et al. (1976) *Intl J Radiat Biol Relat Stud Phys Chem Med* 30:179-187.
Yao & Cooper (1995) *Science* 267:2003-2006.
Yu et al. (1999) *Cancer Res* 59:4200-4203.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for increasing the radiosensitivity of a target tissue in a subject, comprising administering a therapeutically effective amount of a cytosolic phospholipase A2 ($cPLA_2$) antagonist, a vector encoding a $cPLA_2$ antagonist, or a combination thereof, to the subject, wherein the target tissue is a tumor, vasculature supplying blood flow to a tumor, or a combination thereof, and the therapeutically effective amount of the $cPLA_2$ antagonist is an amount sufficient to increase the radiosensitivity of the target tissue.

2. The method of claim 1, wherein the target tissue is endothelial tissue.

3. The method of claim 2 wherein the endothelial tissue is vascular endothelium.

4. The method of claim 1, wherein the target tissue is a tumor.

5. The method of claim 4, wherein the tumor comprises a radiation resistant tumor.

6. The method of claim 1, wherein the target tissue comprises vasculature supplying blood flow to a tumor.

7. The method of claim 1, wherein the subject is a mammal.

8. The method of claim 1, wherein the administering a $cPLA_2$ antagonist comprises administering a minimally therapeutic dose of a $cPLA_2$ antagonist.

9. The method of claim 1, wherein the administering comprises administering a composition comprising:

(a) a $cPLA_2$ antagonist, a vector encoding a $cPLA_2$ antagonist, or a combination thereof; and (b) a pharmaceutically acceptable carrier.

10. The method of claim 1, wherein the $cPLA_2$ antagonist is selected from the group consisting of methyl arachidonyl fluorophosphonate (MAFP) and arachidonyl trifluoromethyl ketone ($AACOCF_3$).

11. The method of claim 10, wherein the MAFP is administered in an amount ranging from about 0.01 to about 10 mg/kg.

12. The method of claim 10, wherein the $AACOCF_3$ is administered in an amount ranging from 0.01 to about 50 mg/kg.

13. The method of claim 1, wherein the $cPLA_2$ antagonist comprises a small interfering RNA (siRNA) targeted to a $cPLA_2$ gene product.

14. A method for suppressing tumor growth in a subject, the method comprising:

(a) administering a $cPLA_2$ antagonist, a vector encoding a $cPLA_2$ antagonist, or a combination thereof to a subject bearing a tumor to increase the radiosensitivity of the tumor; and (b) treating the tumor with ionizing radiation, whereby tumor growth is suppressed.

15. The method of claim 14, wherein the subject is a mammal.

16. The method of claim 14, wherein the administering a cPLA2 antagonist comprises administering a minimally therapeutic dose of a $cPLA_2$ antagonist.

17. The method of claim 14, wherein the administering a $cPLA_2$ antagonist comprises administering a composition comprising:

(a) a $cPLA_2$ antagonist, a vector encoding a $cPLA_2$ antagonist, or a combination thereof; and (b) a pharmaceutically acceptable carrier.

18. The method of claim 14, wherein the $cPLA_2$ antagonist is a small interfering RNA (siRNA) targeted to a $cPLA_2$ gene product.

19. The method of claim 14, wherein the tumor comprises a radiation resistant tumor.

20. The method of claim 14, wherein the treating the tumor with ionizing radiation comprises treating the tumor with a subtherapeutic dose of ionizing radiation.

21. A method for suppressing tumor growth in a subject, the method comprising:

(a) administering a $cPLA_2$ antagonist to a subject bearing a tumor to increase the radiosensitivity of the tumor, wherein the $cPLA_2$ antagonist is selected from the group consisting of methyl arachidonyl fluorophosphonate (MAFP) and arachidonyl trifluoromethyl ketone ($AACOCF_3$); and (b) treating the tumor with ionizing radiation, whereby tumor growth is suppressed.

22. The method of claim 21, wherein the MAFP is administered in an amount ranging from 0.01 to about 10 mg/kg.

23. The method of claim 21, wherein the $AACOCF_3$ is administered in an amount ranging from 0.01 to about 50 mg/kg.

24. A method for inhibiting tumor blood vessel growth, the method comprising:

(a) administering a $cPLA_2$ antagonist, a vector encoding a $cPLA_2$ antagonist, or a combination thereof to a subject bearing a tumor to increase the radiosensitivity of tumor blood vessels; and (b) treating the tumor with ionizing radiation, whereby tumor blood vessel growth is inhibited.

25. The method of claim 24, wherein the administering a $cPLA_2$ antagonist comprises administering a minimally therapeutic dose of a $cPLA_2$ antagonist.

26. The method of claim 24, wherein the administering a $cPLA_2$ antagonist comprises administering a composition comprising:

(a) a $cPLA_2$ antagonist, a vector encoding a $cPLA_2$ antagonist, or a combination thereof; and (b) a pharmaceutically acceptable carrier.

27. The method of claim 24, wherein the $cPLA_2$ antagonist is a small interfering RNA (siRNA) targeted to a $cPLA_2$ gene product.

28. The method of claim 24, wherein the subject is a mammal.

29. The method of claim 24, wherein the tumor comprises a radiation resistant tumor.

30. The method of claim 24, wherein the treating the tumor with ionizing radiation comprises treating the tumor with a subtherapeutic dose of ionizing radiation.

31. The method of claim 24, further comprising reducing the vascular length density of the tumor blood vessels.

32. A method for inhibiting tumor blood vessel growth, the method comprising:

(a) administering a $cPLA_2$ antagonist to a subject bearing a tumor to increase the radiosensitivity of tumor blood vessels, wherein the $cPLA_2$ antagonist is selected from the group consisting of methyl arachidonyl fluorophosphonate (MAFP) and arachidonyl trifluoromethyl ketone ($AACOCF_3$); and (b) treating the tumor with ionizing radiation, whereby tumor blood vessel growth is inhibited.

33. The method of claim 32, wherein the MAFP is administered in an amount ranging from 0.01 to about 10 mg/kg.

34. The method of claim 32, wherein the $AACOCF_3$ is administered in an amount ranging from 0.01 to about 50 mg/kg.

* * * * *